United States Patent
Srivastava et al.

(10) Patent No.: US 9,828,585 B2
(45) Date of Patent: Nov. 28, 2017

(54) METHODS FOR GENERATING CARDIOMYOCYTES

(75) Inventors: Deepak Srivastava, San Francisco, CA (US); Jidong Fu, Albany, CA (US)

(73) Assignee: The J. David Gladstone Instututes, San Francisco, CA (US), A Testamentary Trust Established Under The Will Of J. David Gladstone ( * ) Notice: Subject to any disclaimer, the term of this patent is extended or adjusted under 35 U.S.C. 154(b) by 0 days.

(21) Appl. No.: 14/240,285

(22) PCT Filed: Aug. 29, 2012

(86) PCT No.: PCT/US2012/052862
§ 371 (c)(1),
(2), (4) Date: May 5, 2014

(87) PCT Pub. No.: WO2013/033213
PCT Pub. Date: Mar. 7, 2013

(65) Prior Publication Data
US 2014/0301991 A1    Oct. 9, 2014

Related U.S. Application Data

(60) Provisional application No. 61/529,042, filed on Aug. 30, 2011.

(51) Int. Cl.
| | |
|---|---|
| A01N 63/00 | (2006.01) |
| C12N 5/00 | (2006.01) |
| C12N 5/071 | (2010.01) |
| C12N 15/00 | (2006.01) |
| A61K 38/00 | (2006.01) |
| C12N 5/077 | (2010.01) |
| A61K 35/34 | (2015.01) |
| C12N 15/85 | (2006.01) |

(52) U.S. Cl.
CPC .......... *C12N 5/0657* (2013.01); *A61K 35/34* (2013.01); *C12N 15/85* (2013.01); *C12N 2501/115* (2013.01); *C12N 2501/155* (2013.01); *C12N 2501/16* (2013.01); *C12N 2501/38* (2013.01); *C12N 2501/60* (2013.01); *C12N 2506/02* (2013.01); *C12N 2506/1307* (2013.01); *C12N 2510/00* (2013.01); *C12N 2533/90* (2013.01)

(58) Field of Classification Search
CPC .............. C12N 15/85; C12N 15/0657; C12N 2501/115; C12N 2501/155; C12N 2501/16; C12N 2501/38; C12N 2501/60; C12N 2506/02; C12N 2506/1307; C12N 2510/00; C12N 2533/90; C12N 5/0657; A61K 35/34
See application file for complete search history.

(56) References Cited

U.S. PATENT DOCUMENTS

| | | |
|---|---|---|
| 7,682,828 B2 | 3/2010 | Jaenisch et al. |
| 2005/0043260 A1 | 2/2005 | Schneider et al. |
| 2009/0081170 A1 | 3/2009 | Riley et al. |
| 2009/0163994 A1 | 6/2009 | Quigley et al. |
| 2009/0208465 A1 | 8/2009 | Okano et al. |
| 2009/0253203 A1 | 10/2009 | Eilertsen et al. |
| 2009/0275032 A1 | 11/2009 | Eilertsen et al. |
| 2010/0075421 A1 | 3/2010 | Yamanaka et al. |
| 2010/0135970 A1 | 6/2010 | Kishore et al. |
| 2010/0330044 A1 | 12/2010 | Blanpain et al. |
| 2011/0165570 A1 | 7/2011 | Feng et al. |
| 2013/0216503 A1 | 8/2013 | Srivastava et al. |
| 2014/0235526 A1 | 8/2014 | Srivastava et al. |

FOREIGN PATENT DOCUMENTS

| | | |
|---|---|---|
| EP | 1876233 | 1/2008 |
| WO | 03006950 | 1/2003 |
| WO | 03010303 | 2/2003 |
| WO | 2004081205 | 9/2004 |
| WO | 2006078034 | 7/2006 |
| WO | 2008088882 | 7/2008 |
| WO | WO/2008/088882 * | 7/2008 |
| WO | 2008151387 | 12/2008 |
| WO | 2009/152484 A2 | 12/2009 |
| WO | 2009/152485 A2 | 12/2009 |
| WO | 2010/124143 A1 | 10/2010 |
| WO | WO 2011/109695 A1 | 9/2011 |
| WO | 2011/139688 A3 | 11/2011 |
| WO | 2011/163531 | 12/2011 |

OTHER PUBLICATIONS

Alaynick et al 2007, Cell Metabolism 6:13-24.*
Feng et al 2009, Nature Cell Biol. 11:197-203.*
USPTO STIC Sequence search of Dec. 14, 2015; pp. 1-7.*
Ieda et al., "Direct reprogramming of fibroblasts into functional cardiomyocytes by defined factors", Cell, 2010, 142 (3):375-386.
Takahashi et al., "Induction of pluripotent stem cells from mouse embryonic and adult fibroblast cultures by defined factors", Cell, 2006, 126:663-676.
Alaynick, "Phenotypic characterization of estrogen-related receptor gamma mutant mice" Jan. 1, 2006, pp. 123, para 3, Fig 4.9, 168 pages total [retrieved from http://escholarship.org/uc/item/6w80b6st on Oct. 7, 2012].
Choi; et al. "MyoD converts primary dermal fibroblasts, chondroblasts, smooth muscle, and retinal pigmented epithelial cells into striated mononucleated myoblasts and multinucleated myotubes", Proc Natl Acad Sci U S A (Oct. 1990), 87(20): 7988-7992.

(Continued)

*Primary Examiner* — Christopher M Babic
*Assistant Examiner* — Kelaginamane T Hiriyanna
(74) *Attorney, Agent, or Firm* — Convergent Law Group LLP

(57) ABSTRACT

The present disclosure provides method of generating cardiomyocytes from post-natal fibroblasts. The present disclosure further provides cells and compositions for use in generating cardiomyocytes.

13 Claims, 35 Drawing Sheets

(56) References Cited

OTHER PUBLICATIONS

Min; et al. "Significant improvement of heart function by cotransplantation of human mesenchymal stem cells and fetal cardiomyocytes in postinfarcted pigs", Ann Thorac Surg (Nov. 2002), Abstract.
Potthoff; et al. "MEF2: a central regulator of diverse developmental programs", Development (Dec. 2007), 134(23):4131-4140.
Qian; et al. "In vivo reprogramming of murine cardiac fibroblasts into induced cardiomyocytes", Nature (May 2012), 485(7400):593-598.
Takeuchi; et al. Directed transdifferentiation of mouse mesoderm to heart tissue by defined factors, Nature (Jun. 2009), 459(7247):708-711.
Teng; et al. "A Role for Tbx2 in the Regulation of the alpha2(1) Collagen Gene in Human Fibroblasts", J Cell Biochem (Oct. 2007), 102(3):618-625.
Zhou; et al. "Generation of induced pluripotent stem cells using recombinant proteins", Cell Stem Cell (May 2009), 4(5):381-384.
Shiojima, Ichiro and Komuro Issei; "The heart development and regeneration"; (2005); The Medical Frontline 60, 8; pp. 1781-178.
Vierbuchen, et al.; "Direct conversion of fibroblasts to functional neurons by defined factors"; Nature; vol. 463; (Feb. 25, 2010); pp. 1035-1041.
Yamada et al.; "Single-Cell-Derived Mesenchymal Stem Cells Overexpressing Csx/Nkx2.5 and GATA4 Undergo the Stochastic Cardiomyogenic Fate and Behave like Transient Amplifying Cells"; Experimental Cell Research, Academic Press, US 313(4); (2007); pp. 698-706.
Xu, Meifeng et al; "GATA-4 Plays an Important Role in Bone Marrow Stem Cell Transdifferentiation into Myocytes"; Supplement III Circulation vol. 110, No. 17; Oct. 26, 2004; pp. 1341.
Zeng, Junyi et al; "Co-culture with cardiomyocytes induces mesenchymal stem cells to differentiate into cardiomyocyte-like cells and express heart development-associated genes"; Cell Research (2008) 18:s62; 1 page.
Ji-Dong Fu et al: "Direct Reprogramming of Human Fibroblasts toward a Cardiomyocyte-like State", Stem Cell Reports, vol. 1, No. 3, Sep. 1, 2013 (Sep. 1, 2013), pp. 235-247, ISSN: 2213-6711, DOI: 10.1016/j.stemcr.2013.07.005.

* cited by examiner

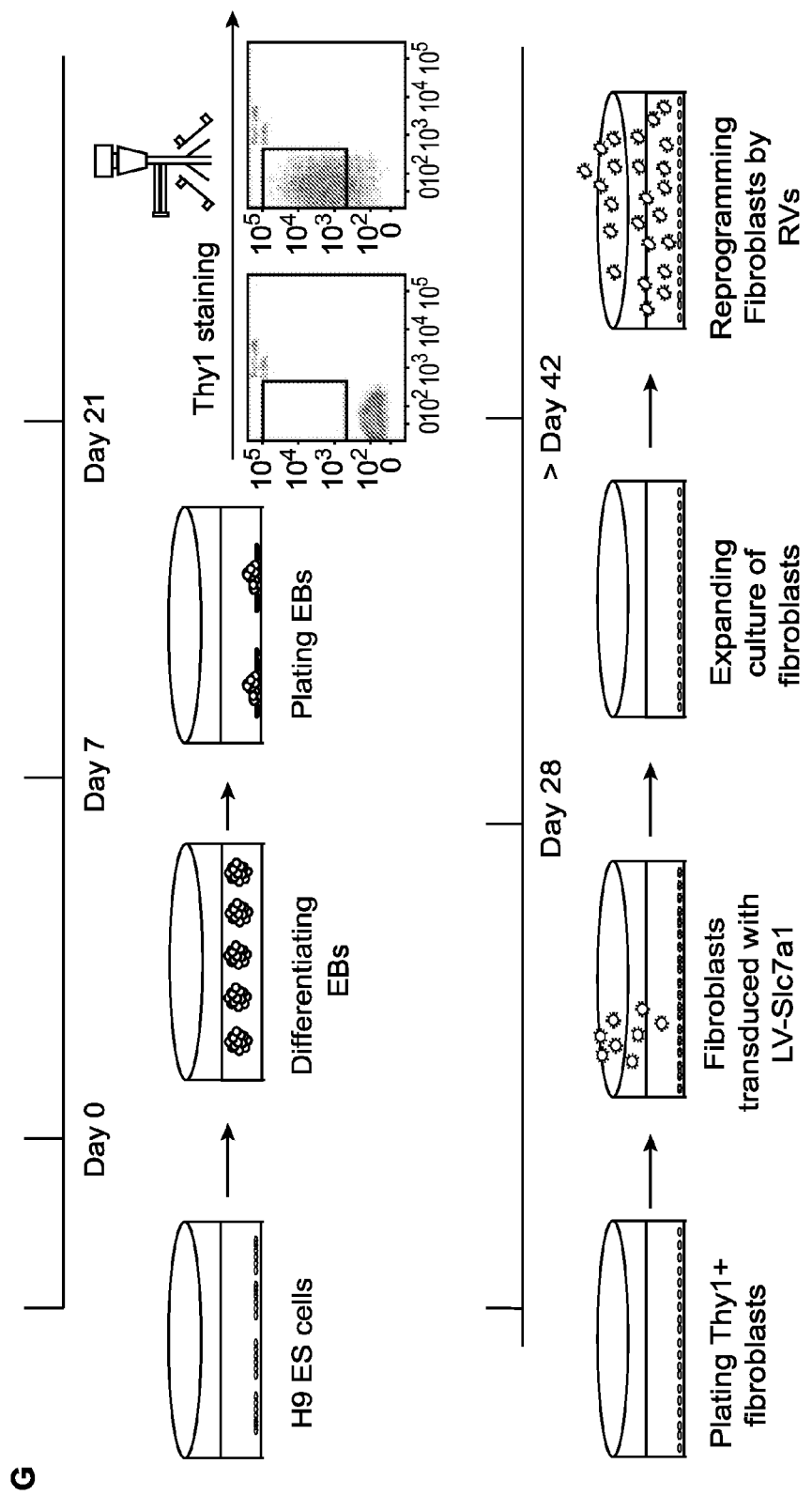
FIG. 1 (Cont. 1)

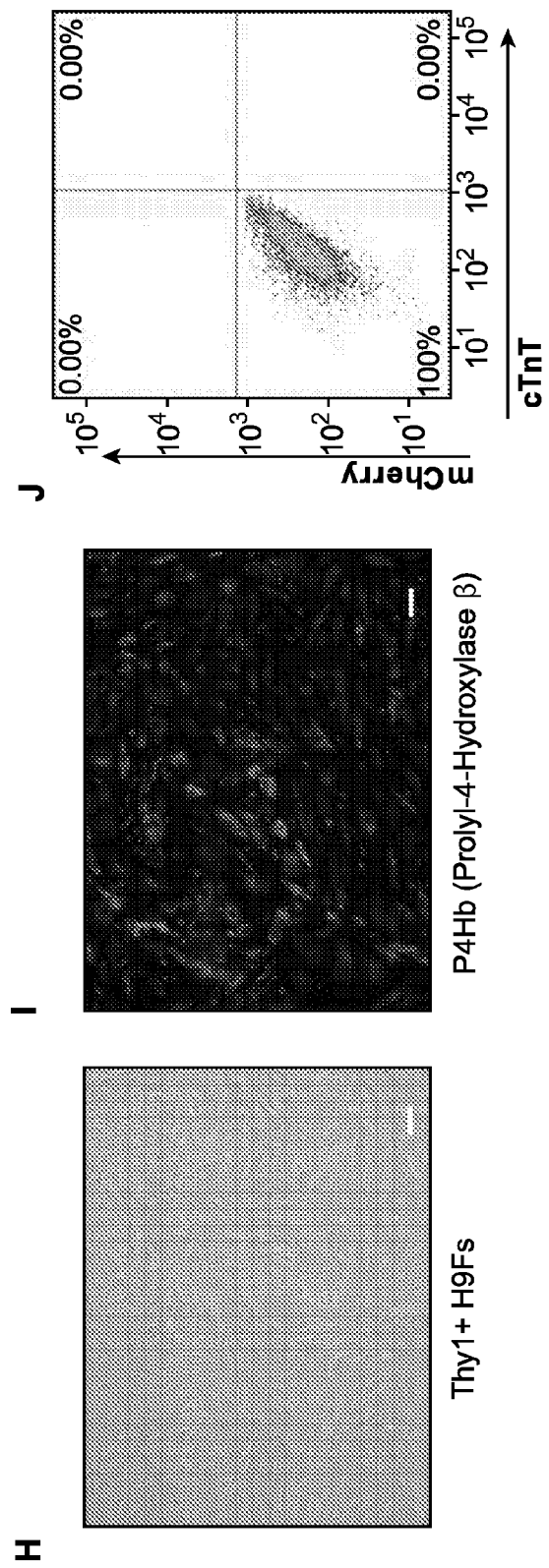
FIG. 1 (Cont. 2)

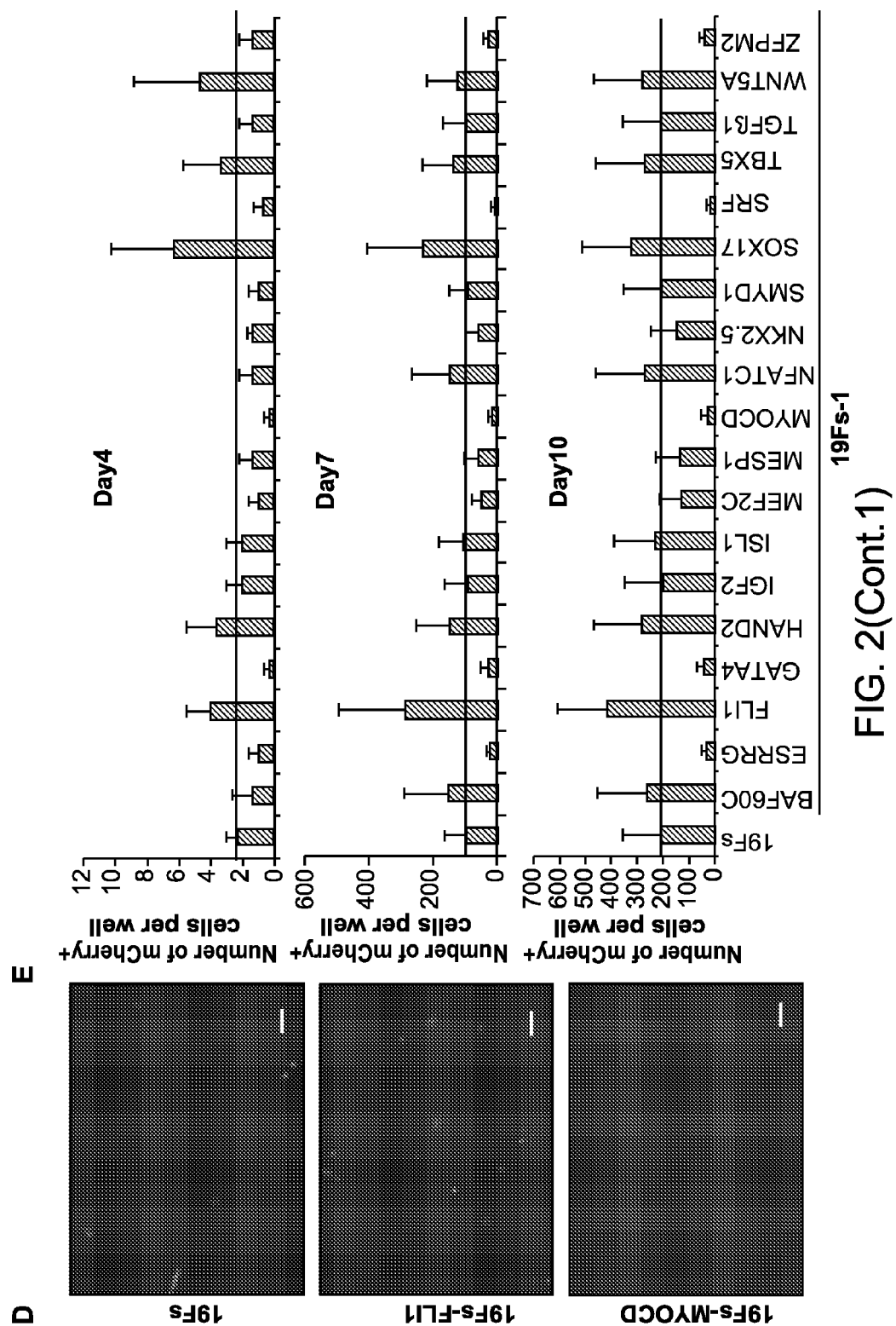
FIG. 2(Cont.1)

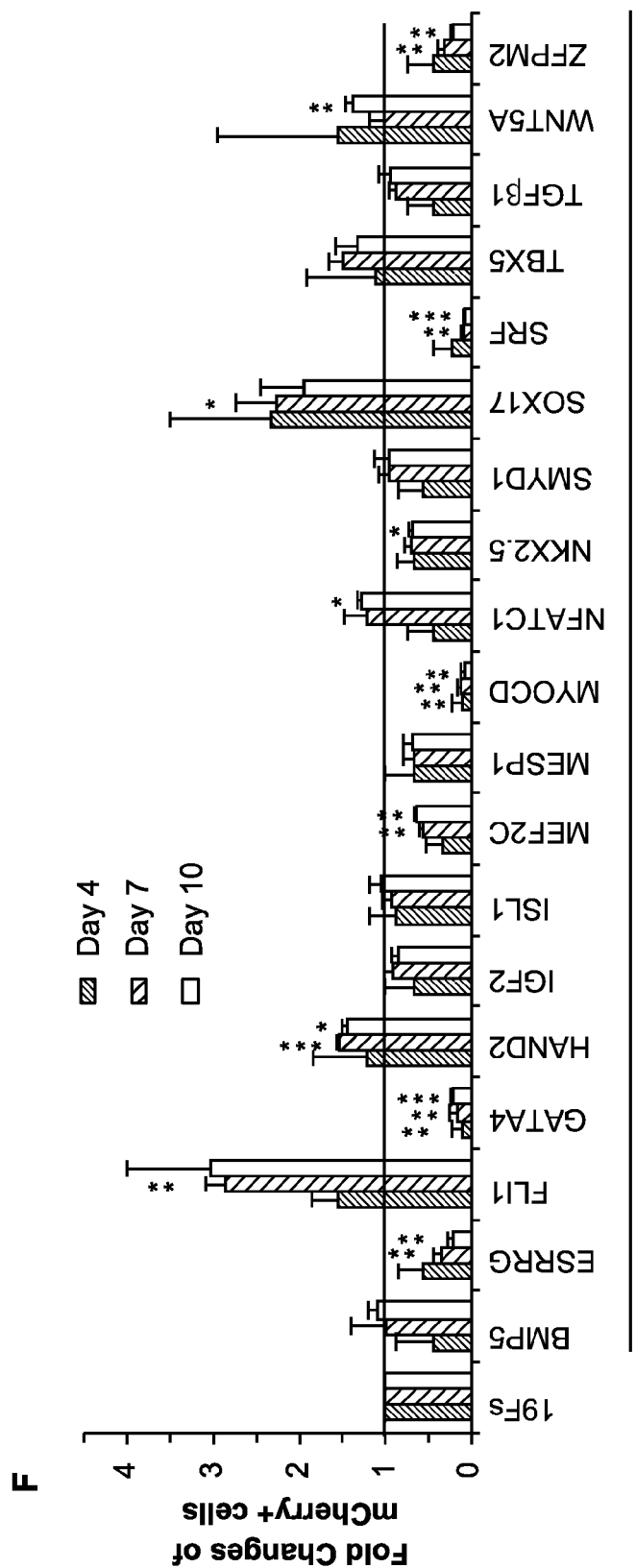
FIG. 2(Cont. 2)

D
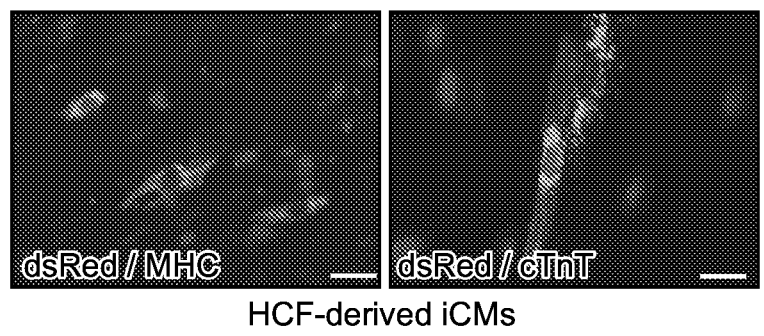
HCF-derived iCMs
E
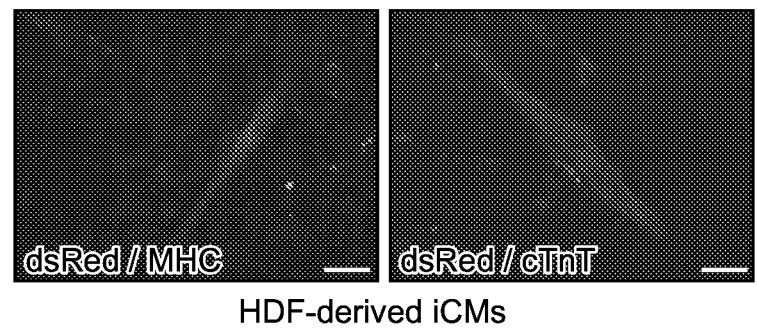
HDF-derived iCMs
FIG. 4 (Cont. 1)

F
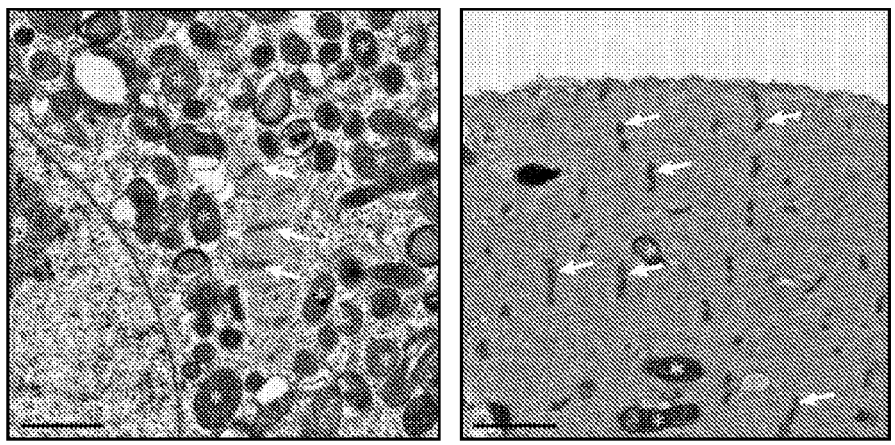
G
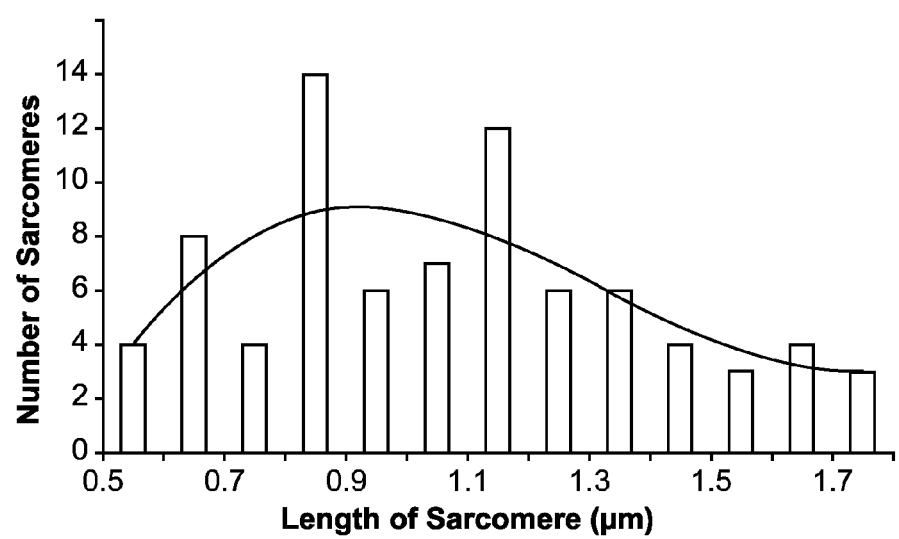
FIG. 4 (Cont. 2)

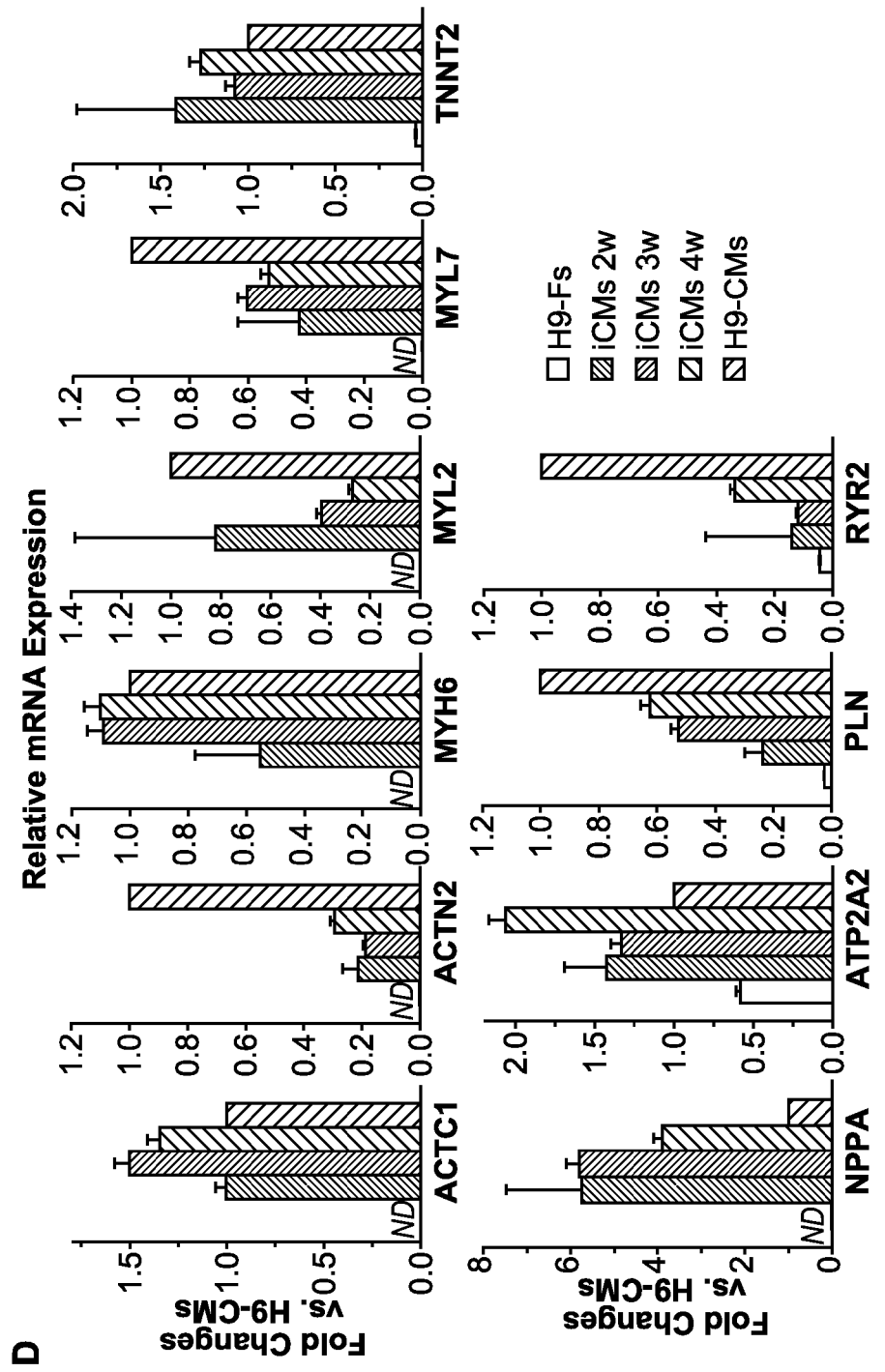
FIG. 5(Cont. 1)

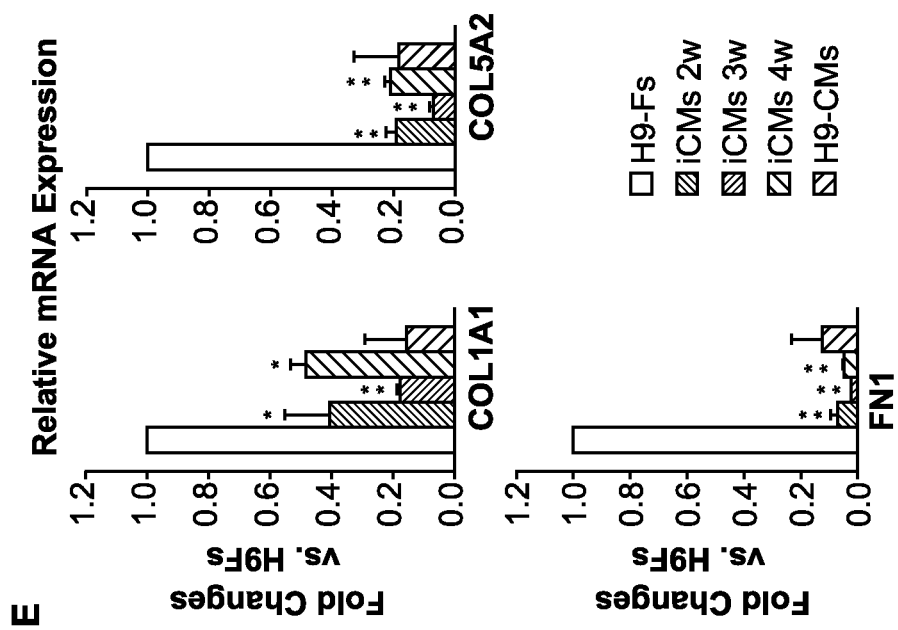
FIG. 5(Cont. 2)

GenBank NP_001127757.1
*Homo sapiens* Esrrg
435 aa

```
  1 msnkdrhids scssfiktep sspasltdsv nhhspggssd asgsysstmn ghqngldspp
 61 lypsapilgg sgpvrklydd csstivedpq tkceymlnsm pkrlclvcgd iasgyhygva
121 sceackaffk rtiqgnieys cpatneceit krrrkscqac rfmkclkvgm lkegvrldrv
181 rggrqkykrr idaenspyln pqlvqpakkp ynkivshllv aepekiyamp dptvpdsdik
241 alttlcdlad relvviigwa khipgfstls ladqmsllqs awmeililgv vyrslsfede
301 lvyaddyimd edqsklagll dlnnailqlv kkyksmklek eefvtlkaia lansdsmhie
361 dveavqklqd vlhealqdye agqhmedprr agkmlmtlpl lrqtstkavq hfyniklegk
421 vpmhklflem leakv (SEQ ID NO:1)
```

FIG. 9

GenBank NM_001134285
*Homo sapiens* Esrrg
1308 nt

```
  1 atgtcaaaca aagatcgaca cattgattcc agctgttcgt ccttcatcaa gacggaacct
 61 tccagcccag cctccctgac ggacagcgtc aaccaccaca gccctggtgg ctcttcagac
121 gccagtggga gctacagttc aaccatgaat ggccatcaga acggacttga ctcgccacct
181 ctctacccctt ctgctcctat cctggggagt agtgggcctg tcaggaaact gtatgatgac
241 tgctccagca ccattgttga agatcccccag accaagtgtg aatacatgct caactcgatg
301 cccaagagac tgtgtttagt gtgtggtgac atcgcttctg ggtaccacta tgggtagca
361 tcatgtgaag cctgcaaggc attcttcaag aggacaattc aaggcaatat agaatacagc
421 tgccctgcca cgaatgaatg tgaaatcaca aagcgcagac gtaaatcctg ccaggcttgc
481 cgcttcatga agtgtttaaa agtgggcatg aggtgcgtct tgacagagta
541 cgtggaggtc ggcagaagta caagcgcagg ctgaaagaag ataagatgcgg ataccagaga
601 cctcagctgg ttcagccagc caaaaagcca gaacctactg tatacaagag tttgttggtg
661 gctgaaccgg agaagatcta tgccatgcct gaccctactg gcagcag tgacatcaaa
721 gcccctcacta cactgtgtga cttggccgac cgagagttgg tggttatcat tggatgggcg
781 aagcatattc caggcttctc cacgctgtcc ctggcggacc agatgagcct tctgcagagt
841 gcttggatgg aaatttttgat ccttggtgtc gtataccggt ctctttcgtt tgaggatgaa
901 cttgtctatg cagacgatta tataatggac gaagaccagt ccaaattagc aggccttctt
961 gatctaaata atgctatcct gcagctggta aagaaataca agagcatgaa gctgaaaaaa
```

FIG. 10A

```
1021  gaagaatttg tcaccctcaa agctatagct cttgctaatt cagactccat gcacatagaa
1081  gatgttgaag ccgttcagaa gcttcaggat gtcttacatg aagcgctgca ggattatgaa
1141  gctggccagc acatggaaga ccctcgtcga gctggcaaga tgctgatgac actgccactc
1201  ctgaggcaga cctctaccaa ggccgtgcag catttctaca acatcaaaact agaaggcaaa
1261  gtcccaatgc acaaactttt tttggaaatg ttggaggcca aggtctga (SEQ ID NO:2)
```

FIG. 10B

Esrrg sequence alignment

```
Seq1 = AB307715   (436 aa)
Seq2 = NP_001127757 (435 aa)
Seq3 = NP_001429  (458 aa)
Seq4 = CAH70619   (442 aa)
Seq5 = AAH08218   (343 aa)

seq2    ------------------------------------MSNKDRHIDSSCCSSFIKTEPSSPASLTDSVNHHSPGG  37
seq4    ------------------------------------MSNKDRHIDSSCCSSFIKTEPSSPASLTDSVNHHSPGG  37
seq1    ------------------------------------MSNKDRHIDSSCCSSFIKTEPSSPASLTDSVNHHSPGG  37
seq3    MDSVELCLPESFSLHYEEELLCRMSNKDRHIDSSCCSSFIKTEPSSPASLTDSVNHHSPGG              60
seq5    ------------------------------------MSNKDRHIDSSCCSSFIKTEPSSPASLTDSVNHHSPGG  37
                                            ************************************ seq2    SSDASGSYSSTMNGHQNGLDSPPLYPSAPILGGSGPVRKLYDDCSSTIVEDPQTKCEYML  97
seq4    SSDASGSYSSTMNGHQNGLDSPPLYPSAPILGGSGPVRKLYDDCSSTIVEDPQTKCEYML  97
seq1    SSDASGSYSSTMNGHQNGLDSPPLYPSAPILGGSGPVRKLYDDCSSTIVEDPQTKCEYML  97
seq3    SSDASGSYSSTMNGHQNGLDSPPLYPSAPILGGSGPVRKLYDDCSSTIVEDPQTKCEYML  120
seq5    SSDASGSYSSTMNGHQNGLDSPPLYPSAPILGGSGPVRKLYDDCSSTIVEDPQTKCEYML  97
        ************************************************************ seq2    NSMPKRLCLVCGDIASGYHYGVASCEACKAFFKRTIQGNIEYSCPATNECEITKRRRKSC  157
seq4    NSMPKRLCLVCGDIASGYHYGVASCEACKAFFKRTIQGNIEYSCPATNECEITKRRRKSC  157
seq1    NSMPKRLCLVCGDIASGYHYGVASCEACKAFFKRTIQGNIEYSCPATNECEITKRRRKSC  157
seq3    NSMPKRLCLVCGDIASGYHYGVASCEACKAFFKRTIQGNIEYSCPATNECEITKRRRKSC  180
seq5    NSMPKRLCLVCGDIASGYHYGVASCEACKAFFKRTIQGNIEYSCPATNECEITKRRRKSC  157
        ************************************************************ seq2    QACRFMKCLKVGMLKEGVRLDRVRGGRQKYKRRIDAENSPYLNPQLVQPAKKP-------  210
seq4    QACRFMKCLKVGMLKEGVRLDRVRGGRQKYKRRIDAENSPYLNPQLVQPAKKPLLWSDPA  217
seq1    QACRFMKCLKVGMLKEGVRLDRVRGGRQKYKRRIDAENSPYLNPQLVQPAKKP-------  210
seq3    QACRFMKCLKVGMLKEGVRLDRVRGGRQKYKRRIDAENSPYLNPQLVQPAKKP-------  233
seq5    QACRFMKCLKVGMLKEGVRLDRVRGGRQKYKRRIDAENSPYLNPQLVQPAKKP-------  210
        ****************************************************
```

FIG. 11A

```
seq2  YNKIVSHLLVAEPEKIYAMPDPTVPDSDIKALTTLCDLADRELVVIIGWAKHIPGFSTLS  270
seq4  DNKIVSHLLVAEPEKIYAMPDPTVPDSDIKALTTLCDLADRELVVIIGWAKHIPGFSTLS  277
seq1  YTKIVSHLLVAEPEKIYAMPDPTVPDSDIKALTTLCDLADRELVVIIGWAKHIPGFSTLS  270
seq3  YNKIVSHLLVAEPEKIYAMPDPTVPDSDIKALTTLCDLADRELVVIIGWAKHIPGFSTLS  293
seq5  YNKIVSHLLVAEPEKIYAMPDPTVPDSDIKALTTLCDLADRELVVIIGWAKHIPGFSTLS  270
      .************************************************************* seq2  LADQMSLLQSAWMEILILGVVYRSLSFEDELVYADDYIMDEDQSKLAGLLDLNNAILQLV  330
seq4  LADQMSLLQSAWMEILILGVVYRSLSFEDELVYADDYIMDEDQSKLAGLLDLNNAILQLV  337
seq1  LADQMSLLQSAWMEILILGVVYRSLSFEDELVYADDYIMDEDQSKLAGLLDLNNAILQLV  330
seq3  LADQMSLLQSAWMEILILGVVYRSLSFEDELVYADDYIMDEDQSKLAGLLDLNNAILQLV  353
seq5  LADQMSLLQSAWMEILILGVVYRSLSFEDELVYADDYIMDEDQSKLAGLLDLNNAILQLV  330
      ************************************************************* seq2  KKYKSMKLEKEEFVTLKAIALANSDSMHIEDVEAVQKLQDVLHEALQDYEAGQHMEDPRR  390
seq4  KKYKSMKLEKEEFVTLKAIALANSDSMHIEDVEAVQKLQDVLHEALQDYEAGQHMEDPRR  397
seq1  KKYKSMKLEKEEFVTLKAIALANSDSMHIEDVEAVQKLQDVLHEALQDYEAGQHMEDPRR  390
seq3  KKYKSMKLEKEEFVTLKAIALANSDSMHIEDVEAVQKLQDVLHEALQDYEAGQHMEDPRR  413
seq5  KKYKSMKLEKKKK------------------------------------------------  343
      **********::                                       (SEQ ID NO:7)

seq2  AGKMLMTLPLLRQTSTKAVQHFYNIKLEGKVPMHKLFLEMLEAKV-    (SEQ ID NO:3)  435
seq4  AGKMLMTLPLLRQTSTKAVQHFYNIKLEGKVPMHKLFLEMLEAKV-    (SEQ ID NO:4)  442
seq1  AGKMLMTLPLLRQTSTKAVQHFYNIKLEGKVPMHKLFLEMLEAKVC    (SEQ ID NO:5)  436
seq3  AGKMLMTLPLLRQTSTKAVQHFYNIKLEGKVPMHKLFLEMLEAK--    (SEQ ID NO:6)  457
seq5  ---------------------------------------------
```

FIG. 11B

GATA4
*Homo sapiens*
442 aa
GenBank NP_002043.2

```
  1 myqslamaan hgpppgayea ggpgafmhga gaasspvyvp tprvpssvlg lsylqgggag
 61 sasggasggs sggaasgagp gtqqgspgws qagadgaayt pppvsprfsf pgttgslaaa
121 aaaaaareaa ayssgggaag aglagreqyg ragfagsyss pypaymadvg aswaaaaaas
181 agpfdspvlh slpgranpaa rhpnldmfdd fsegrecvnc gamstplwrr dgtghylcna
241 cglyhkmngi nrplikpqrr lsasrrvgls cancqttttt lwrrnaegep vcnacglymk
301 lhgvprplam rkegiqtrkr kpknlnkskt paapsgsesl ppasgassns snattsssee
361 mrpiktepgl sshyghsssv sqtfsvsams ghgpsihpvl salklspqgy aspvsqspqt
421 sskqdswnsl vladshgdii ta (SEQ ID NO:8)
```

FIG. 12

GATA4
*Homo sapiens*
1329 nt
GenBank NM_002052

```
   1 atgtatcaga gcttggccat ggccgccaac cacgggccgc cccccggtgc ctacgaggcg
  61 ggcggcccg gcgccttcat gcacgccgcg ggcgccgcgt cctcgccagt ctacgtgccc
 121 acaccgcggg tgcccctcct cgtgctgggc ctgtcctacc tccaggggcgg aggcgcgggc
 181 tctgcgtccg gaggcgctc gggcagccc gggatggagc ccgcgtctgg tgcggggccc
 241 gggacccagc agggcagcc gggatggagc cttctccttc caggcgggag cgcttacacc
 301 ccgccgccgg tgtcgccgcg cttctccttc ccggggacca ccggtccct ggcggccgc
 361 gccgccgctg ccgcgccccg ggaagctgcg gcctacagca gcctacagca gtgcggcg agcgcgggt
 421 gcgggcctgg cgggccgcga gcagtgggg cgcgccgct tcgcggctc ctactccagc
 481 ccctaccgg cttacatggc cgacgtgggc gcgtcctggg ccgcagccgc cgccgcctcc
 541 gccggccct tcgacagccc ggtcctgcac agcctgcccg gcagagagtg tgtcaactgt
 601 cgacacccca atctcgatat gtttgacgac ttctcagaag gcagagagtg tgtcaactgt
 661 gggctatgt ccaccccgct ctggaggcga gatgggacgg gtcactatct gtgcaacgcc
 721 tgcggcctct accacaagat gaaccggcat ggccatcc tgtgccaact gccagaccac
 781 ctgtccgcct ccgcgcgagt gggcgagct gggcgagcct gtgtgcaatg cggaaagagg
 841 ctgtggcgcc gcaatgcgga tctgaagat tctgccaatg cggaaagagg ggatccaaac
 901 ctccacgggg tcccaggcc tctttgcaatg cggaaagagg cttcaggcag ccaccagcag
 961 aagcccaaga acctgaataa atctaagaca cagcaacgcca ccaccagcag cagcgaggag
1021 cctccgcca gcggtgcttc cagcaactcc agcaacgcca tcatctcact acgggcacag cagctccgtg
1081 atgcgtccca tcaagacgga gctgccctg tcatctcact acgggcacag cagctccgtg
1141 tcccagacgt tctcagtcag tgcgatgtct ggccatgggc cctccatcca ccctgtcctc
1201 tcggccctga agctctcccc acaaggctat gcgtctcccg tcagccagtc tccacagacc
1261 agctccaagc aggactcttg gaaacgcctg gtcttggccg acagtcacgg ggacataatc
1321 actgcgtaa (SEQ ID NO:9)
```

FIG. 13

MEF2c
*Homo sapiens*
Isoform 2; 463 aa
GenBank NP_001124477

```
  1 mgrkkiqitr imdernrqvt ftkrkfglmk kayelsvlcd ceialiifns tnklfqyast
 61 dmdkvllkyt eynephesrt nsdivealnk kenkgcespd pdssyaltpr teekykkine
121 efdnmikshk ipavpppnfe mpvsipvssh nslvysnpvs slgnpnlipl ahpslqrnsm
181 spgvthrpps agntgglmgg dltsgagtsa gngygnprns pgllvspgnl nknmqakspp
241 pmnlgmnnrk pdlrvlippg skntmpsvnq rinnsqsaqs latpvvsvat ptlpqgmgg
301 ypsaisttyg teyslssadl sslsgfntas alhlgsvtgw qqqhlhnmpp salsqlgact
361 sthlsqssnl slpstqslni ksepvspprd rtttpsrypq htrheagrsp vdslsscsss
421 ydgsdredhr nefhspiglt rpspderesp svkrmrlseg wat (SEQ ID NO:10)
```

FIG. 14

MEF2c
*Homo sapiens*
Isoform 2; 1392 nt
GenBank NM_001131005

```
   1 atgggagaa aaaagattca gattacgagg attatggatg aacgtaacag acaggtgaca
  61 tttacaaaga ggaaatttgg gttgatgaag aaggcttatg agctgagcgt gctgtgtgac
 121 tgtgagattg cgctgatcat cttcaacagc accacaagc tgtttccagta tgccagcacc
 181 gacatggaca aagtgcttct caagtacacg gagtacaacg agcccgatga gagccggaca
 241 aactcagaca tcgtggaggc attgaacaag aaagaaaaca aggctgtga aagcccgat
 301 cccgactcct cttatgcact cacccacgc actgaagaaa attcctgctg ttccacctcc caacttcgag
 361 gaatttgata atatgatcaa gagtcataaa gtccagcac aacagtttgg tgtacagcaa ccctgtcagc
 421 atgccagtct ccatcccaac attgccactg gctcaccctt ctctgcagag gaatagtatg
 481 tcactgggaa accccaacct acctccaagt gcaggtaaca caggtggtct gatgggtgga
 541 tctcctggtg taacacatcg caccagtgca gggaacgggt atgcaatcc ccgaaactca
 601 gacctcacgt ctggtgcagg ctggtctcac tggtaacttg aacaagaata tgcaagcaaa atctcctccc
 661 ccaggtctgc tggtctcacc tggtaacttg aacaagaata ccagatctcc gagttctttat tccaccaggc
 721 ccaatgaatt taggaatgaa taaccgtaaa ccagatctcc aggataaata actcccagtc ggctcagtca
 781 agcaagaata cgatgccatc agtgacaaact cctactttac caggacaagg aatgggagga
 841 ttggctaccc cagtggtttc cgtagcaact cctactttac accgagtact ctctgagtag tgcagacctg
 901 tatccatcag ccatttcaac aacatatggt accgagtact gtcttcacc ttggttcagt aactggctgg
 961 tcatcctgt ctgggtttaa caccgccagc gtcttcacc tctgccctca gtcagttggg agcttgcact
1021 caacagcaac acctacataa catgccacca ttcaaatctc tcctgccctt ctactcaaag cctcaacatc
1081 agcactcatt tatctcagag ttcaaatctc tcctagagac cgtaccacca cccttcgag ataccacaa
1141 aagtcagaaac ctgttctcc tcctagagac gagatctcct gttgacagct tgagcagctg tagcagttcg
1201 cacacgcgcc acgaggcggg ggaccgaga gtccaccgg ggatcaccgg aacgaattcc actccccat tggactcacc
1261 tacgacggga gcgaccgaga ggaacgaaag tcagtcaagc tcagtcaagc gcatgcgact ttctgaagga
1321 agaccttcgc cggacgaaag ggaaagtccc
1381 tgggcaacat ga (SEQ ID NO:11)
```

FIG. 15

MEF2c
*Homo sapiens*
Isoform 1; 473 aa
GenBank NP_002388

```
  1 mgrkkiqitr imdernrqvt ftkrkfglmk kayelsvlcd ceialiifns tnklfqyast
 61 dmdkvllkyt eynephesrt nsdivetlrk kglngcdspd pdaddsvghs pesedkyrki
121 nedidlmisr qrlcavpppn fempvsipvs shnslvysnp vsslgnpnll plahpslqrn
181 smspgvthrp psagntgglm ggdltsgagt sagngygnpr nspgllvspg nlnknmqaks
241 pppmnlgmnn rkpdlrvlip pgskntmpsv sedvdlilng rinnsqsaqs latpvvsvat
301 ptlpgqmgg ypsaisttyg teyslssadl sslsgfntas alhlgsvtgw qqqhlhnmpp
361 salsqlgact sthlsqssnl slpstqslni ksepvspprd rtttpsrypq htrheagrsp
421 vdslsscsss ydgsdredhr nefhspiglt rpspderesp svkrmrlseg wat (SEQ ID NO:12)
```

FIG. 16

MEF2c
*Homo sapiens*
Isoform 1; 1422 nt
GenBank NM_002397

```
   1 atggggagaa aaaagattca gattacgagg attatggatg aacgtaacag acaggtgaca
  61 tttacaaaga ggaaatttgg gttgatgaag aaggcttatg agctgagcgt gctgtgtgac
 121 tgtgagattg cgctgatcat cttcaacagc accaacaagc tgttccagta tgccagcacc
 181 gacatggaca aagtgcttct caagtacacg gagtacaacg agccgcatga gagcggaca
 241 aactcagaca tcgtggagac gttgagaaag aagggcctta agcctgtgta cagcccagac
 301 cccgatgcgg acgattccgt aggtcacagc cctgagtctg aggacaagta caggaaaatt
 361 aacgaagata ttgatctaat gatcagcagg caaagattgt gtgctgttcc acctcccaac
 421 ttcgagatgc cagtctccat cccagtgtcc agccacacaa gtttggtgta cagcaaccct
 481 gtcagctcac tgggaaaccc caacctattg cccctgctc accctctct gcagaggaat
 541 agtatgtctc ctgtgtaac acatcgacct ccaagtgcag gtaacacagg tggtctgatg
 601 ggtggagacc tcacgtctgg tgcaggcacc agtgcaggga acgggtatgg caatcccga
 661 aactcaccag gtctgctggt ctcacctggt aacttgaaca agaatatgca agcaaaatct
 721 cctccccaa tgaatttagg aatgaataac cgtaaaccag atctccgagt tcttattcca
 781 ccaggcagca agaatacgat gccatcagtg tctgaggatg tcgacctgct tttgaatcaa
 841 aggataaata actcccagtc ggctcagtca ttggctaccc cagtggtttc cgtagcaact
 901 cctacttttac caggacaagg aatggggagga tatccatcag ccatttcaac aacatatgtt
 961 accgagtact ctctgttcag tgcagacctg aactggctgg caacagcaac acctacataa caccgccagc
1021 gctcttcacc ttgcccatca aactggctggg caacagcaac agcactcatt tatctcagag ttcaaatctc
1081 tctgccctca gtcagttggg agcttgcact cctcaacatc aagtcagaac cacacgcgcc tgtttctcc tcctagagac
1141 tccctgcctt ctactcaaag ataccacaa cccttcgag ataccacaa cacacgcgcc acgagggccgg gagatctcct
1201 cgtaccacca cccttcgag ataccacaa acacgcgcc acgagggccgg gagatctcct
1261 gttgacagct tgagcagctg tagcagttcg tacgacggga gcgacgaga ggatcaccgg
1321 aacgaattcc actccccat tggactcacc agacccttcgc cggacgaaag ggaaagtccc
1381 tcagtcaagc gcatgcgact ttctgaagga tgggcaacat ga (SEQ ID NO:13)
```

FIG. 17

Tbx5
*Homo sapiens*
513 aa
GenBank CAA70592.1

```
  1 madadealag ahlwsltqkt clrfeprars gppasppgrp rsrlhpagme gikvflhere
 61 lwlkfhevte miitkagrrm fpsykvkvtg inpktkyill mdivpaddhr ykfadnkwcv
121 tgkaepamag rlyvhpdspa tgahwmrqlv sfqklkltnn hldpfghiil nsmhkyqprl
181 hivkadenng fgskntafct hvfpetafia vtsyqnhkit qlkiennpfa kgfrgsddme
241 lhrmsrmqsk eypvvprstv rqkvasnhsp fssesralst ssnlgsqyqc engvsgpsqd
301 llpppnpypl pqehsqiyhc tkrkeeecst tdhpykkpym etspseedsf yrssypqqqg
361 lgasyrtesa qrqacmyass appsepvpsl ediscntwps mpsyssctvt tvqpwtgypt
421 stspltsprg pwslgwlawq pwlptagrgn vpstrppvah qpvvssvgpq tglqspgtlq
481 ppeflyshgv qglyplistt lctelawcrv erq (SEQ ID NO:14)
```

FIG. 18

Tbx5
*Homo sapiens*
1542 nt
GenBank Y09445

```
   1 atggccgacg cagacgaggc tttggctggc gcacacctct ggagcctgac gcaaaagacc
  61 tgcctgcgat tcgaaccgag agcgcgctcg gggccccccag caagtccccc cggtcgtccc
 121 cgcagccgcc ttcacccagc aggcatggag ggaatcaaag tgtttctcca tgaaagagaa
 181 ctgtggctaa aattccacga agtcacggaa atgatcataa ccaaggctgg aaggcggatg
 241 tttcccagtt acaaagtgaa ggtgacgggc attaatccca aaacgaagta cattctttctc
 301 atggacattg tacctgcgga cgatcacaga tacaaattcg cagataataa atggtgtgtg
 361 acgggcaaag ctgagcccgc catggctggc cgcctgtacg tgcaccaga ctccccccgcc
 421 acgggggcgc attggatgag gcagctcgtc tccttccaga aactcaagct caccaacaac
 481 cacctggacc catttgggca tattattcta aattccatgc acaaatacca gcctagatta
 541 cacatcgtga aagcggatga aaataatgga tttgctcaa aaaatacagc gttctgcact
 601 cacgtctttc ctgagactgc gttatagca gtgacttcct accagaacca caagatcacg
 661 caattaaaga ttgagaataa tcccctttgcc aaaggatttc ggggcagtga tgacatggag
 721 ctgcacagaa tgtcaagaat gcaaagtaaa cagtcct ttcagcagcg agtctcgagc tctctccacc
 781 aggcaaaaag tggcctccaa ccaacagtgt gagaatggtg tttccggccc ctcccaggac
 841 tcatccaatt tggggtccca ataccactg ataccaaat atagccaaat ttaccattgt
 901 ctcctgcctc cacccaaccc atgttccacc acagaccatc cctataagaa gccctacatg
 961 accaagagga aagaggaaga agattccttc tacgctcta gctatccaca gcagcagggc
1021 gagacatcac ccagtgaaga agagtcggca cagcggcaag cttgcatgta tgccagctct
1081 ctgggtgcct cctacaggac agagtcggca gccagccta gaggacatca gctgcaacac gtggccaagc
1141 gcgcccccca gcgagcctgt gccagtcacc caccgtcacc accgtgcagc catgacagg ctaccctacc
1201 atgccttcct acagcagctg cacctcacttc acctcgggc cctggtccc tcggctggct ggcatggcaa
1261 agcacttctc cgctcacttc ccacagctgg gagaggaat gttcccagca ccagacctcc cgtggcccac
1321 ccatggctcc ccacagctgg tcagcagtgt gggcccccaa actgcctgc agtcccctgc caccctttcag
1381 cagcctgtgg tcagcagtgt tcctctactc tcatggccgtg caaggactct atcccctcat cagtaccact
1441 cccctgagt tcctctactc tcatggccatg gtcagagtg gagcgacaat ag (SEQ ID NO:15)
1501 ctgtgcacgg agttggcatg
```

FIG. 19

Tbx5
*Homo sapiens*
518 aa
GenBank NP_000183

```
  1 madadegfgl ahtplepdak dlpcdskpes algapsksps spqaaftqqg megikvflhe
 61 relwlkfhev gtemiitkag rrmfpsykvk vtglnpktky illmdivpad dhrykfadnk
121 wsvtgkaepa mpgrlyvhpd spatgahwmr qlvsfqklkl tnnhldpfgh iilnsmhkyq
181 prlhivkade nngfgsknta fcthvfpeta fiavtsyqnh kitqlkienn pfakgfrgsd
241 dmelhrmsrm qskeypvvpr stvrqkvasn hspfssesra lstssnlgsq yqcengvsgp
301 sqdllpppnp yplpqehsqi yhctkrkeee csttdhpykk pymetspsee dsfyrssypq
361 qqglgasyrt esaqrqacmy assappsepv plediscnt wpsmpsyssc tvttvqpmdr
421 lpyqhfsahf tsgplvprla gmanhgspql gegmfqhqts vahqpvvrqc gpqtglqspg
481 tlqppeflys hgvprtlsph qyhsvhgvgm vpewsdns (SEQ ID NO:16)
```

FIG. 20

Tbx5
*Homo sapiens*
1557 nt
GenBank NM_000192

```
   1 atggccgacg cagacgaggg ctttggcctg gcgcacacgc ctctggagcc tgacgcaaaa
  61 gacctgccct gcgattcgaa accgagagc acccagggc gcgctcgggg ccccagcaa gtccccgtcg
 121 tccccgcagg ccgcctttcac ccagcagggc atggagggaa tcaaagtgtt tctccatgaa
 181 agagaactgt ggctaaaatt ccacgaagtg ggcacggaaa tgatcataac caaggctgga
 241 aggcggatgt ttcccagtta caaagtgaag gtgacgggcc ttaatcccaa aacgaagtac
 301 attctttctca tggacattgt acctgccgac gatcacagat acaaattcgc agataataaa
 361 tggtctgtga cgggcaaagc tgagcccgcc atgcctggcc gcctgtacgt gcaccagac
 421 tcccccgcca ccggggcgca ttggatgagg cagctcgtct ccttccagaa actcaagctc
 481 accaacaacc acctggaccc atttgggcat attattctaa attccatgca caataccag
 541 cctagattac acatcgtgaa agcggatgaa aataatggat ttgctcaaa aaatacagcg
 601 ttctgcactc acgtctttcc tgagactgcg tttatagcag tgacttccta ccgaaccac
 661 aagatcacgc aattaaagat tgagaataat cccttttgcca aaggatttcg gggcagtgat
 721 gacatggagc tgcacagaat gtcaagaatg caaagtaaag aatatcccgt ggtcccagg
 781 agcaccgtga ggcaaaaagt ggcctccaac cacagtcctt tcagcagcga gtctcgagct
 841 ctctccacct catccaatt gggtccccaa taccagtgtg agaatggtgt ttccggcccc
 901 tcccaggacc tcctgcctcc acccaaccca taccactgc cccaggagca tagccaaatt
 961 taccattgta ccaagaggaa agaggaagaa tgttccacca cagaccatcc ctataagaag
1021 ccctacatgg agacatcacc cagtgaagaa gattccttct accgctctag ctatccacag
1081 cagcagggcc tgggtgcctc ctacagaca gagtcggcac agcggcaagc ttgcatgtat
1141 gccagctctg cgccccccag cgagcctgtg cccagcctag aggacatcag ctgcaacacg
1201 tggccaagca tgcccttccta cagcagtcc cgctcacttc ccgtgcagcc catggacagg
1261 ctaccctacc agcactttc cgctcactg acctcggggc ggagagggaa tgttccagca ccagacctcc
1321 ggcatggcca accatgtggt caggcagtgt ctgcgctcag ggctgctc ccagacctgc
1381 gtgccaccc agcctgtgt cctctactct caggcgtgc ctgcgtgca gtcccctgcc
1441 accccttcagc cccctgagtt ctgtgcatg catgcgtgc caaggactct atccctcat
1501 cagtaccact ctgtgcacgg agttggcatg gtgccagagt ggagcgacaa tagctaa      (SEQ ID NO:17)
```

FIG. 21

Mesoderm posterior protein 1 (Mesp1); 268 aa
*Homo sapiens*
GenBank NP_061140.1

```
  1 maqplcppls eswmlsaawg ptrrpppsdk dcgrslvssp dswgstpads pvasparpgt
 61 lrdprapsvg rrgarssrlg sgqrqsaser eklrmrtlar alhelrrflp psvapagqsl
121 tkietlrlai ryighlsavl lvsavragas wgsppacpga raapeprdpp alfaeaacpe gqamepspps
181 egqqqrglg lvsavragas wgsppacpga raapeprdpp alfaeaacpe gqamepspps
241 pllpgdvlal letwmplspl ewlpeepk (SEQ ID NO:18)
```

FIG. 22

Mesp1
*Homo sapiens*
GenBank NM_018670.3; 804 nt

```
  1 atgcccagc cctgtgccc gccgctctcc gagtcctgga tgctctctgc ggcctggggc
 61 ccaactcggc ggccgccgcc ctccgacaag gactgcgcc gctccctcgt ctcgtcccca
121 gactcatggg gcagcaccc agccgacagc cccgtggcga gccgcgcg gcaggcacc
181 ctccgggacc cccgcgccc ctccgtaggt aggcgcggcg cgcagcag ccgcctgggc
241 agcgggcaga ggcagagcgc cagtgagcgg gagaaactgc gcatgcgcac gctgcccgc
301 gccctgcacg agctgcgccg cttctaccg ccgtccgtgg cgcccgcggg ccagagcctg
361 accaagatcg agacgctgcg cctgctatc cgctatatcg gccacctgtc ggccgtgcta
421 ggcctcagcg aggagagtct ccagcgccgg tgccggcagc gcggtgacgc ggggtccct
481 cgggctgcc cgctgtgccc gccgcgcaga cccgcgcaga tgcagacacg gacgcaggct
541 gaggggcagg ggcaggggcg cggctgggc ctggtatccg ccgtccgcgc cggggcgtcc
601 tggggatccc cgcctgcctg ccccgagcc cgagctgcac ccgagccgcg cgacccgcct
661 gcgctgttcg ccgaggcggc gtgccctgaa gggcaggcga tggagccaag cccaccgtcc
721 ccgctccttc cgggcgacgt gctgctctg ttggagacct ggatgcccct ctcgcctctg
781 gagtggctgc ctgaggagcc caagtga (SEQ ID NO:19)
```

FIG. 23

SEQUENCE LISTING

<160> NUMBER OF SEQ ID NOS: 36

<210> SEQ ID NO 1
<211> LENGTH: 435
<212> TYPE: PRT

<213> ORGANISM: Homo sapiens

<400> SEQUENCE: 1

```
Met Ser Asn Lys Asp Arg His Ile Asp Ser Ser Cys Ser Ser Phe Ile
1               5                   10                  15

Lys Thr Glu Pro Ser Ser Pro Ala Ser Leu Thr Asp Ser Val Asn His
            20                  25                  30

His Ser Pro Gly Gly Ser Ser Asp Ala Ser Gly Ser Tyr Ser Ser Thr
        35                  40                  45

Met Asn Gly His Gln Asn Gly Leu Asp Ser Pro Pro Leu Tyr Pro Ser
    50                  55                  60

Ala Pro Ile Leu Gly Gly Ser Gly Pro Val Arg Lys Leu Tyr Asp Asp
65                  70                  75                  80

Cys Ser Ser Thr Ile Val Glu Asp Pro Gln Thr Lys Cys Glu Tyr Met
                85                  90                  95

Leu Asn Ser Met Pro Lys Arg Leu Cys Leu Val Cys Gly Asp Ile Ala
            100                 105                 110

Ser Gly Tyr His Tyr Gly Val Ala Ser Cys Glu Ala Cys Lys Ala Phe
        115                 120                 125

Phe Lys Arg Thr Ile Gln Gly Asn Ile Glu Tyr Ser Cys Pro Ala Thr
130                 135                 140

Asn Glu Cys Glu Ile Thr Lys Arg Arg Arg Lys Ser Cys Gln Ala Cys
145                 150                 155                 160

Arg Phe Met Lys Cys Leu Lys Val Gly Met Leu Lys Glu Gly Val Arg
                165                 170                 175

Leu Asp Arg Val Arg Gly Gly Arg Gln Lys Tyr Lys Arg Arg Ile Asp
            180                 185                 190

Ala Glu Asn Ser Pro Tyr Leu Asn Pro Gln Leu Val Gln Pro Ala Lys
        195                 200                 205

Lys Pro Tyr Asn Lys Ile Val Ser His Leu Leu Val Ala Glu Pro Glu
    210                 215                 220

Lys Ile Tyr Ala Met Pro Asp Pro Thr Val Pro Asp Ser Asp Ile Lys
225                 230                 235                 240

Ala Leu Thr Thr Leu Cys Asp Leu Ala Asp Arg Glu Leu Val Val Ile
                245                 250                 255

Ile Gly Trp Ala Lys His Ile Pro Gly Phe Ser Thr Leu Ser Leu Ala
            260                 265                 270

Asp Gln Met Ser Leu Leu Gln Ser Ala Trp Met Glu Ile Leu Ile Leu
        275                 280                 285

Gly Val Val Tyr Arg Ser Leu Ser Phe Glu Asp Glu Leu Val Tyr Ala
    290                 295                 300

Asp Asp Tyr Ile Met Asp Glu Asp Gln Ser Lys Leu Ala Gly Leu Leu
305                 310                 315                 320

Asp Leu Asn Asn Ala Ile Leu Gln Leu Val Lys Lys Tyr Lys Ser Met
                325                 330                 335

Lys Leu Glu Lys Glu Glu Phe Val Thr Leu Lys Ala Ile Ala Leu Ala
            340                 345                 350

Asn Ser Asp Ser Met His Ile Glu Asp Val Glu Ala Val Gln Lys Leu
        355                 360                 365

Gln Asp Val Leu His Glu Ala Leu Gln Asp Tyr Glu Ala Gly Gln His
    370                 375                 380

Met Glu Asp Pro Arg Arg Ala Gly Lys Met Leu Met Thr Leu Pro Leu
385                 390                 395                 400
```

```
Leu Arg Gln Thr Ser Thr Lys Ala Val Gln His Phe Tyr Asn Ile Lys
            405                 410                 415

Leu Glu Gly Lys Val Pro Met His Lys Leu Phe Leu Glu Met Leu Glu
        420                 425                 430

Ala Lys Val
        435

<210> SEQ ID NO 2
<211> LENGTH: 1308
<212> TYPE: DNA
<213> ORGANISM: Homo sapiens

<400> SEQUENCE: 2
atgtcaaaca aagatcgaca cattgattcc agctgttcgt ccttcatcaa gacggaacct      60
tccagcccag cctccctgac ggacagcgtc aaccaccaca gccctggtgg ctcttcagac     120
gccagtggga gctacagttc aaccatgaat ggccatcaga acggacttga ctcgccacct     180
ctctacccct tgctcctatc cctgggaggt agtgggcctg tcaggaaact gtatgatgac     240
tgctccagca ccattgttga agatccccag accaagtgtg aatacatgct caactcgatg     300
cccaagagac tgtgtttagt gtgtggtgac atcgcttctg gtaccactat ggggtagca     360 tcatgtgaag cctgcaaggc attcttcaag aggacaattc aaggcaatat agaatacagc     420
tgccctgcca cgaatgaatg tgaaatcaca agcgcagac gtaaatcctg ccaggcttgc      480
cgcttcatga agtgtttaaa agtgggcatg ctgaagaag gggtgcgtct tgacagagta      540
cgtggaggtc ggcagaagta caagcgcagg atagatgcgg agaacagccc atacctgaac     600
cctcagctgg ttcagccagc caaaaagcca tataacaaga ttgtctcaca tttgttggtg     660
gctgaaccgg agaagatcta tgccatgcct gaccctactg tccccgacag tgacatcaaa     720
gccctcacta cactgtgtga cttggccgac cgagagttgg tggttatcat ggatgggcg     780 aagcatattc caggcttctc cacgctgtcc ctggcggacc agatgagcct tctgcagagt     840
gcttggatgg aaattttgat ccttggtgtc gtataccggt ctctttcgtt tgaggatgaa     900
cttgtctatg cagacgatta tataatggac gaagaccagt ccaaattagc aggccttctt     960
gatctaaata atgctatcct gcagctggta aagaaataca gagcatgaa gctggaaaaa    1020 gaagaatttg tcaccctcaa agctatagct cttgctaatt cagactccat gcacatagaa    1080
gatgttgaag ccgttcagaa gcttcaggat gtcttacatg aagcgctgca ggattatgaa    1140
gctggccagc acatggaaga ccctcgtcga gctggcaaga tgctgatgac actgccactc    1200
ctgaggcaga cctctaccaa ggccgtgcag catttctaca acatcaaact agaaggcaaa    1260
gtcccaatgc acaaactttt tttggaaatg ttggaggcca aggtctga                 1308

<210> SEQ ID NO 3
<211> LENGTH: 435
<212> TYPE: PRT
<213> ORGANISM: Homo sapiens

<400> SEQUENCE: 3

Met Ser Asn Lys Asp Arg His Ile Asp Ser Ser Cys Ser Ser Phe Ile
1               5                   10                  15

Lys Thr Glu Pro Ser Ser Pro Ala Ser Leu Thr Asp Ser Val Asn His
            20                  25                  30

His Ser Pro Gly Gly Ser Ser Asp Ala Ser Gly Ser Tyr Ser Ser Thr
        35                  40                  45

Met Asn Gly His Gln Asn Gly Leu Asp Ser Pro Pro Leu Tyr Pro Ser
```

```
              50                  55                  60
Ala Pro Ile Leu Gly Gly Ser Gly Pro Val Arg Lys Leu Tyr Asp Asp
 65                  70                  75                  80

Cys Ser Ser Thr Ile Val Glu Asp Pro Gln Thr Lys Cys Glu Tyr Met
                     85                  90                  95

Leu Asn Ser Met Pro Lys Arg Leu Cys Leu Val Cys Gly Asp Ile Ala
                100                 105                 110

Ser Gly Tyr His Tyr Gly Val Ala Ser Cys Glu Ala Cys Lys Ala Phe
                115                 120                 125

Phe Lys Arg Thr Ile Gln Gly Asn Ile Glu Tyr Ser Cys Pro Ala Thr
130                 135                 140

Asn Glu Cys Glu Ile Thr Lys Arg Arg Arg Lys Ser Cys Gln Ala Cys
145                 150                 155                 160

Arg Phe Met Lys Cys Leu Lys Val Gly Met Leu Lys Glu Gly Val Arg
                165                 170                 175

Leu Asp Arg Val Arg Gly Gly Arg Gln Lys Tyr Lys Arg Arg Ile Asp
                180                 185                 190

Ala Glu Asn Ser Pro Tyr Leu Asn Pro Gln Leu Val Gln Pro Ala Lys
                195                 200                 205

Lys Pro Tyr Asn Lys Ile Val Ser His Leu Leu Val Ala Glu Pro Glu
210                 215                 220

Lys Ile Tyr Ala Met Pro Asp Pro Thr Val Pro Asp Ser Asp Ile Lys
225                 230                 235                 240

Ala Leu Thr Thr Leu Cys Asp Leu Ala Asp Arg Glu Leu Val Val Ile
                245                 250                 255

Ile Gly Trp Ala Lys His Ile Pro Gly Phe Ser Thr Leu Ser Leu Ala
                260                 265                 270

Asp Gln Met Ser Leu Leu Gln Ser Ala Trp Met Glu Ile Leu Ile Leu
                275                 280                 285

Gly Val Val Tyr Arg Ser Leu Ser Phe Glu Asp Glu Leu Val Tyr Ala
                290                 295                 300

Asp Asp Tyr Ile Met Asp Glu Asp Gln Ser Lys Leu Ala Gly Leu Leu
305                 310                 315                 320

Asp Leu Asn Asn Ala Ile Leu Gln Leu Val Lys Lys Tyr Lys Ser Met
                325                 330                 335

Lys Leu Glu Lys Glu Glu Phe Val Thr Leu Lys Ala Ile Ala Leu Ala
                340                 345                 350

Asn Ser Asp Ser Met His Ile Glu Asp Val Glu Ala Val Gln Lys Leu
                355                 360                 365

Gln Asp Val Leu His Glu Ala Leu Gln Asp Tyr Glu Ala Gly Gln His
                370                 375                 380

Met Glu Asp Pro Arg Arg Ala Gly Lys Met Leu Met Thr Leu Pro Leu
385                 390                 395                 400

Leu Arg Gln Thr Ser Thr Lys Ala Val Gln His Phe Tyr Asn Ile Lys
                405                 410                 415

Leu Glu Gly Lys Val Pro Met His Lys Leu Phe Leu Glu Met Leu Glu
                420                 425                 430

Ala Lys Val
            435

<210> SEQ ID NO 4
<211> LENGTH: 442
<212> TYPE: PRT
<213> ORGANISM: Homo sapiens
```

<400> SEQUENCE: 4

```
Met Ser Asn Lys Asp Arg His Ile Asp Ser Ser Cys Ser Ser Phe Ile
1               5                   10                  15

Lys Thr Glu Pro Ser Ser Pro Ala Ser Leu Thr Asp Ser Val Asn His
            20                  25                  30

His Ser Pro Gly Gly Ser Ser Asp Ala Ser Gly Ser Tyr Ser Ser Thr
        35                  40                  45

Met Asn Gly His Gln Asn Gly Leu Asp Ser Pro Pro Leu Tyr Pro Ser
    50                  55                  60

Ala Pro Ile Leu Gly Gly Ser Gly Pro Val Arg Lys Leu Tyr Asp Asp
65                  70                  75                  80

Cys Ser Ser Thr Ile Val Glu Asp Pro Gln Thr Lys Cys Glu Tyr Met
                85                  90                  95

Leu Asn Ser Met Pro Lys Arg Leu Cys Leu Val Cys Gly Asp Ile Ala
            100                 105                 110

Ser Gly Tyr His Tyr Gly Val Ala Ser Cys Glu Ala Cys Lys Ala Phe
        115                 120                 125

Phe Lys Arg Thr Ile Gln Gly Asn Ile Glu Tyr Ser Cys Pro Ala Thr
130                 135                 140

Asn Glu Cys Glu Ile Thr Lys Arg Arg Arg Lys Ser Cys Gln Ala Cys
145                 150                 155                 160

Arg Phe Met Lys Cys Leu Lys Val Gly Met Leu Lys Glu Gly Val Arg
                165                 170                 175

Leu Asp Arg Val Arg Gly Gly Arg Gln Lys Tyr Lys Arg Arg Ile Asp
            180                 185                 190

Ala Glu Asn Ser Pro Tyr Leu Asn Pro Gln Leu Val Gln Pro Ala Lys
        195                 200                 205

Lys Pro Leu Leu Trp Ser Asp Pro Ala Asp Asn Lys Ile Val Ser His
    210                 215                 220

Leu Leu Val Ala Glu Pro Glu Lys Ile Tyr Ala Met Pro Asp Pro Thr
225                 230                 235                 240

Val Pro Asp Ser Asp Ile Lys Ala Leu Thr Thr Leu Cys Asp Leu Ala
                245                 250                 255

Asp Arg Glu Leu Val Val Ile Ile Gly Trp Ala Lys His Ile Pro Gly
            260                 265                 270

Phe Ser Thr Leu Ser Leu Ala Asp Gln Met Ser Leu Leu Gln Ser Ala
        275                 280                 285

Trp Met Glu Ile Leu Ile Leu Gly Val Val Tyr Arg Ser Leu Ser Phe
290                 295                 300

Glu Asp Glu Leu Val Tyr Ala Asp Asp Tyr Ile Met Asp Glu Asp Gln
305                 310                 315                 320

Ser Lys Leu Ala Gly Leu Leu Asp Leu Asn Asn Ala Ile Leu Gln Leu
                325                 330                 335

Val Lys Lys Tyr Lys Ser Met Lys Leu Glu Lys Glu Glu Phe Val Thr
            340                 345                 350

Leu Lys Ala Ile Ala Leu Ala Asn Ser Asp Ser Met His Ile Glu Asp
        355                 360                 365

Val Glu Ala Val Gln Lys Leu Gln Asp Val Leu His Glu Ala Leu Gln
370                 375                 380

Asp Tyr Glu Ala Gly Gln His Met Glu Asp Pro Arg Arg Ala Gly Lys
385                 390                 395                 400

Met Leu Met Thr Leu Pro Leu Leu Arg Gln Thr Ser Thr Lys Ala Val
```

-continued

```
                405                 410                 415
Gln His Phe Tyr Asn Ile Lys Leu Glu Gly Lys Val Pro Met His Lys
            420                 425                 430

Leu Phe Leu Glu Met Leu Glu Ala Lys Val
            435                 440

<210> SEQ ID NO 5
<211> LENGTH: 436
<212> TYPE: PRT
<213> ORGANISM: Homo sapiens

<400> SEQUENCE: 5

Met Ser Asn Lys Asp Arg His Ile Asp Ser Ser Cys Ser Ser Phe Ile
1               5                   10                  15

Lys Thr Glu Pro Ser Ser Pro Ala Ser Leu Thr Asp Ser Val Asn His
            20                  25                  30

His Ser Pro Gly Gly Ser Ser Asp Ala Ser Gly Ser Tyr Ser Ser Thr
        35                  40                  45

Met Asn Gly His Gln Asn Gly Leu Asp Ser Pro Pro Leu Tyr Pro Ser
    50                  55                  60

Ala Pro Ile Leu Gly Gly Ser Gly Pro Val Arg Lys Leu Tyr Asp Asp
65                  70                  75                  80

Cys Ser Ser Thr Ile Val Glu Asp Pro Gln Thr Lys Cys Glu Tyr Met
                85                  90                  95

Leu Asn Ser Met Pro Lys Arg Leu Cys Leu Val Cys Gly Asp Ile Ala
            100                 105                 110

Ser Gly Tyr His Tyr Gly Val Ala Ser Cys Glu Ala Cys Lys Ala Phe
        115                 120                 125

Phe Lys Arg Thr Ile Gln Gly Asn Ile Glu Tyr Ser Cys Pro Ala Thr
    130                 135                 140

Asn Glu Cys Glu Ile Thr Lys Arg Arg Arg Lys Ser Cys Gln Ala Cys
145                 150                 155                 160

Arg Phe Met Lys Cys Leu Lys Val Gly Met Leu Lys Glu Gly Val Arg
                165                 170                 175

Leu Asp Arg Val Arg Gly Gly Arg Gln Lys Tyr Lys Arg Arg Ile Asp
            180                 185                 190

Ala Glu Asn Ser Pro Tyr Leu Asn Pro Gln Leu Val Gln Pro Ala Lys
        195                 200                 205

Lys Pro Tyr Thr Lys Ile Val Ser His Leu Leu Val Ala Glu Pro Glu
    210                 215                 220

Lys Ile Tyr Ala Met Pro Asp Pro Thr Val Pro Asp Ser Asp Ile Lys
225                 230                 235                 240

Ala Leu Thr Thr Leu Cys Asp Leu Ala Asp Arg Glu Leu Val Val Ile
                245                 250                 255

Ile Gly Trp Ala Lys His Ile Pro Gly Phe Ser Thr Leu Ser Leu Ala
            260                 265                 270

Asp Gln Met Ser Leu Leu Gln Ser Ala Trp Met Glu Ile Leu Ile Leu
        275                 280                 285

Gly Val Val Tyr Arg Ser Leu Ser Phe Glu Asp Glu Leu Val Tyr Ala
    290                 295                 300

Asp Asp Tyr Ile Met Asp Glu Asp Gln Ser Lys Leu Ala Gly Leu Leu
305                 310                 315                 320

Asp Leu Asn Asn Ala Ile Leu Gln Leu Val Lys Lys Tyr Lys Ser Met
                325                 330                 335
```

```
Lys Leu Glu Lys Glu Phe Val Thr Leu Lys Ala Ile Ala Leu Ala
                340                 345                 350

Asn Ser Asp Ser Met His Ile Glu Asp Val Glu Ala Val Gln Lys Leu
            355                 360                 365

Gln Asp Val Leu His Glu Ala Leu Gln Asp Tyr Glu Ala Gly Gln His
        370                 375                 380

Met Glu Asp Pro Arg Arg Ala Gly Lys Met Leu Met Thr Leu Pro Leu
385                 390                 395                 400

Leu Arg Gln Thr Ser Thr Lys Ala Val Gln His Phe Tyr Asn Ile Lys
                405                 410                 415

Leu Glu Gly Lys Val Pro Met His Lys Leu Phe Leu Glu Met Leu Glu
            420                 425                 430

Ala Lys Val Cys
        435

<210> SEQ ID NO 6
<211> LENGTH: 458
<212> TYPE: PRT
<213> ORGANISM: Homo sapiens

<400> SEQUENCE: 6

Met Asp Ser Val Glu Leu Cys Leu Pro Glu Ser Phe Ser Leu His Tyr
1               5                   10                  15

Glu Glu Glu Leu Leu Cys Arg Met Ser Asn Lys Asp Arg His Ile Asp
                20                  25                  30

Ser Ser Cys Ser Ser Phe Ile Lys Thr Glu Pro Ser Ser Pro Ala Ser
            35                  40                  45

Leu Thr Asp Ser Val Asn His His Ser Pro Gly Gly Ser Ser Asp Ala
    50                  55                  60

Ser Gly Ser Tyr Ser Ser Thr Met Asn Gly His Gln Asn Gly Leu Asp
65                  70                  75                  80

Ser Pro Pro Leu Tyr Pro Ser Ala Pro Ile Leu Gly Gly Ser Gly Pro
                85                  90                  95

Val Arg Lys Leu Tyr Asp Asp Cys Ser Ser Thr Ile Val Glu Asp Pro
                100                 105                 110

Gln Thr Lys Cys Glu Tyr Met Leu Asn Ser Met Pro Lys Arg Leu Cys
            115                 120                 125

Leu Val Cys Gly Asp Ile Ala Ser Gly Tyr His Tyr Gly Val Ala Ser
    130                 135                 140

Cys Glu Ala Cys Lys Ala Phe Phe Lys Arg Thr Ile Gln Gly Asn Ile
145                 150                 155                 160

Glu Tyr Ser Cys Pro Ala Thr Asn Glu Cys Glu Ile Thr Lys Arg Arg
                165                 170                 175

Arg Lys Ser Cys Gln Ala Cys Arg Phe Met Lys Cys Leu Lys Val Gly
            180                 185                 190

Met Leu Lys Glu Gly Val Arg Leu Asp Arg Val Arg Gly Gly Arg Gln
    195                 200                 205

Lys Tyr Lys Arg Arg Ile Asp Ala Glu Asn Ser Pro Tyr Leu Asn Pro
210                 215                 220

Gln Leu Val Gln Pro Ala Lys Lys Pro Tyr Asn Lys Ile Val Ser His
225                 230                 235                 240

Leu Leu Val Ala Glu Pro Glu Lys Ile Tyr Ala Met Pro Asp Pro Thr
                245                 250                 255

Val Pro Asp Ser Asp Ile Lys Ala Leu Thr Thr Leu Cys Asp Leu Ala
            260                 265                 270
```

```
Asp Arg Glu Leu Val Val Ile Ile Gly Trp Ala Lys His Ile Pro Gly
            275                 280                 285
Phe Ser Thr Leu Ser Leu Ala Asp Gln Met Ser Leu Leu Gln Ser Ala
        290                 295                 300
Trp Met Glu Ile Leu Ile Leu Gly Val Val Tyr Arg Ser Leu Ser Phe
305                 310                 315                 320
Glu Asp Glu Leu Val Tyr Ala Asp Asp Tyr Ile Met Asp Glu Asp Gln
                325                 330                 335
Ser Lys Leu Ala Gly Leu Leu Asp Leu Asn Asn Ala Ile Leu Gln Leu
            340                 345                 350
Val Lys Lys Tyr Lys Ser Met Lys Leu Glu Lys Glu Glu Phe Val Thr
        355                 360                 365
Leu Lys Ala Ile Ala Leu Ala Asn Ser Asp Ser Met His Ile Glu Asp
370                 375                 380
Val Glu Ala Val Gln Lys Leu Gln Asp Val Leu His Glu Ala Leu Gln
385                 390                 395                 400
Asp Tyr Glu Ala Gly Gln His Met Glu Asp Pro Arg Arg Ala Gly Lys
                405                 410                 415
Met Leu Met Thr Leu Pro Leu Leu Arg Gln Thr Ser Thr Lys Ala Val
            420                 425                 430
Gln His Phe Tyr Asn Ile Lys Leu Glu Gly Lys Val Pro Met His Lys
        435                 440                 445
Leu Phe Leu Glu Met Leu Glu Ala Lys Val
450                 455

<210> SEQ ID NO 7
<211> LENGTH: 343
<212> TYPE: PRT
<213> ORGANISM: Homo sapiens

<400> SEQUENCE: 7

Met Ser Asn Lys Asp Arg His Ile Asp Ser Ser Cys Ser Ser Phe Ile
1               5                   10                  15
Lys Thr Glu Pro Ser Ser Pro Ala Ser Leu Thr Asp Ser Val Asn His
            20                  25                  30
His Ser Pro Gly Gly Ser Ser Asp Ala Ser Gly Ser Tyr Ser Ser Thr
        35                  40                  45
Met Asn Gly His Gln Asn Gly Leu Asp Ser Pro Pro Leu Tyr Pro Ser
    50                  55                  60
Ala Pro Ile Leu Gly Gly Ser Gly Pro Val Arg Lys Leu Tyr Asp Asp
65                  70                  75                  80
Cys Ser Ser Thr Ile Val Glu Asp Pro Gln Thr Lys Cys Glu Tyr Met
                85                  90                  95
Leu Asn Ser Met Pro Lys Arg Leu Cys Leu Val Cys Gly Asp Ile Ala
            100                 105                 110
Ser Gly Tyr His Tyr Gly Val Ala Ser Cys Glu Ala Cys Lys Ala Phe
        115                 120                 125
Phe Lys Arg Thr Ile Gln Gly Asn Ile Glu Tyr Ser Cys Pro Ala Thr
    130                 135                 140
Asn Glu Cys Glu Ile Thr Lys Arg Arg Arg Lys Ser Cys Gln Ala Cys
145                 150                 155                 160
Arg Phe Met Lys Cys Leu Lys Val Gly Met Leu Lys Glu Gly Val Arg
                165                 170                 175
Leu Asp Arg Val Arg Gly Gly Arg Gln Lys Tyr Lys Arg Arg Ile Asp
```

```
                    180                 185                 190
Ala Glu Asn Ser Pro Tyr Leu Asn Pro Gln Leu Val Gln Pro Ala Lys
                195                 200                 205
Lys Pro Tyr Asn Lys Ile Val Ser His Leu Leu Val Ala Glu Pro Glu
            210                 215                 220
Lys Ile Tyr Ala Met Pro Asp Pro Thr Val Pro Asp Ser Asp Ile Lys
225                 230                 235                 240
Ala Leu Thr Thr Leu Cys Asp Leu Ala Asp Arg Glu Leu Val Val Ile
                245                 250                 255
Ile Gly Trp Ala Lys His Ile Pro Gly Phe Ser Thr Leu Ser Leu Ala
            260                 265                 270
Asp Gln Met Ser Leu Leu Gln Ser Ala Trp Met Glu Ile Leu Ile Leu
        275                 280                 285
Gly Val Val Tyr Arg Ser Leu Ser Phe Glu Asp Glu Leu Val Tyr Ala
        290                 295                 300
Asp Asp Tyr Ile Met Asp Glu Asp Gln Ser Lys Leu Ala Gly Leu Leu
305                 310                 315                 320
Asp Leu Asn Asn Ala Ile Leu Gln Leu Val Lys Lys Tyr Lys Ser Met
                325                 330                 335
Lys Leu Glu Lys Lys Lys Lys
            340

<210> SEQ ID NO 8
<211> LENGTH: 442
<212> TYPE: PRT
<213> ORGANISM: Homo sapiens

<400> SEQUENCE: 8

Met Tyr Gln Ser Leu Ala Met Ala Ala Asn His Gly Pro Pro Pro Gly
1               5                   10                  15
Ala Tyr Glu Ala Gly Gly Pro Gly Ala Phe Met His Gly Ala Gly Ala
            20                  25                  30
Ala Ser Ser Pro Val Tyr Val Pro Thr Pro Arg Val Pro Ser Ser Val
        35                  40                  45
Leu Gly Leu Ser Tyr Leu Gln Gly Gly Ala Gly Ser Ala Ser Gly
    50                  55                  60
Gly Ala Ser Gly Gly Ser Ser Gly Gly Ala Ser Gly Ala Gly Pro
65                  70                  75                  80
Gly Thr Gln Gln Gly Ser Pro Gly Trp Ser Gln Ala Gly Ala Asp Gly
                85                  90                  95
Ala Ala Tyr Thr Pro Pro Pro Val Ser Pro Arg Phe Ser Phe Pro Gly
            100                 105                 110
Thr Thr Gly Ser Leu Ala Ala Ala Ala Ala Ala Ala Ala Ala Arg Glu
        115                 120                 125
Ala Ala Ala Tyr Ser Ser Gly Gly Gly Ala Ala Gly Ala Gly Leu Ala
    130                 135                 140
Gly Arg Glu Gln Tyr Gly Arg Ala Gly Phe Ala Gly Ser Tyr Ser Ser
145                 150                 155                 160
Pro Tyr Pro Ala Tyr Met Ala Asp Val Gly Ala Ser Trp Ala Ala Ala
                165                 170                 175
Ala Ala Ala Ser Ala Gly Pro Phe Asp Ser Pro Val Leu His Ser Leu
            180                 185                 190
Pro Gly Arg Ala Asn Pro Ala Ala Arg His Pro Asn Leu Asp Met Phe
        195                 200                 205
```

```
Asp Asp Phe Ser Glu Gly Arg Glu Cys Val Asn Cys Gly Ala Met Ser
            210                 215                 220

Thr Pro Leu Trp Arg Arg Asp Gly Thr Gly His Tyr Leu Cys Asn Ala
225                 230                 235                 240

Cys Gly Leu Tyr His Lys Met Asn Gly Ile Asn Arg Pro Leu Ile Lys
                245                 250                 255

Pro Gln Arg Arg Leu Ser Ala Ser Arg Arg Val Gly Leu Ser Cys Ala
            260                 265                 270

Asn Cys Gln Thr Thr Thr Thr Leu Trp Arg Arg Asn Ala Glu Gly
                275                 280                 285

Glu Pro Val Cys Asn Ala Cys Gly Leu Tyr Met Lys Leu His Gly Val
290                 295                 300

Pro Arg Pro Leu Ala Met Arg Lys Glu Gly Ile Gln Thr Arg Lys Arg
305                 310                 315                 320

Lys Pro Lys Asn Leu Asn Lys Ser Lys Thr Pro Ala Ala Pro Ser Gly
                325                 330                 335

Ser Glu Ser Leu Pro Pro Ala Ser Gly Ala Ser Ser Asn Ser Ser Asn
            340                 345                 350

Ala Thr Thr Ser Ser Ser Glu Glu Met Arg Pro Ile Lys Thr Glu Pro
            355                 360                 365

Gly Leu Ser Ser His Tyr Gly His Ser Ser Val Ser Gln Thr Phe
370                 375                 380

Ser Val Ser Ala Met Ser Gly His Gly Pro Ser Ile His Pro Val Leu
385                 390                 395                 400

Ser Ala Leu Lys Leu Ser Pro Gln Gly Tyr Ala Ser Pro Val Ser Gln
                405                 410                 415

Ser Pro Gln Thr Ser Ser Lys Gln Asp Ser Trp Asn Ser Leu Val Leu
            420                 425                 430

Ala Ser Ser His Gly Asp Ile Ile Thr Ala
            435                 440

<210> SEQ ID NO 9
<211> LENGTH: 1329
<212> TYPE: PRT
<213> ORGANISM: Homo sapiens

<400> SEQUENCE: 9

Ala Thr Gly Thr Ala Thr Cys Ala Gly Ala Gly Cys Thr Thr Gly Gly
1               5                   10                  15

Cys Cys Ala Thr Gly Gly Cys Cys Gly Cys Ala Ala Cys Cys Ala
            20                  25                  30

Cys Gly Gly Gly Cys Cys Gly Cys Cys Cys Cys Cys Gly Gly Thr
        35                  40                  45

Gly Cys Cys Thr Ala Cys Ala Gly Gly Cys Gly Gly Gly Cys Gly
    50                  55                  60

Gly Cys Cys Cys Gly Gly Cys Gly Cys Cys Thr Thr Cys Ala Thr
65                  70                  75                  80

Gly Cys Ala Cys Gly Gly Cys Gly Gly Gly Gly Cys Cys Cys
        85                  90                  95

Gly Cys Gly Thr Cys Cys Thr Cys Gly Cys Cys Ala Gly Thr Cys Thr
        100                 105                 110

Ala Cys Gly Thr Gly Cys Cys Ala Cys Ala Cys Cys Gly Cys Gly
            115                 120                 125

Gly Gly Thr Gly Cys Cys Cys Thr Cys Cys Thr Cys Cys Gly Thr Gly
        130                 135                 140
```

-continued

Cys Thr Gly Gly Gly Cys Cys Thr Gly Thr Cys Cys Thr Ala Cys Cys
145                 150                 155                 160

Thr Cys Cys Ala Gly Gly Cys Gly Gly Ala Gly Cys Gly Gly Cys
            165                 170                 175

Gly Gly Gly Cys Thr Cys Thr Gly Cys Gly Thr Cys Cys Gly Gly Ala
            180                 185                 190

Gly Gly Cys Gly Cys Cys Thr Cys Gly Gly Cys Gly Gly Cys Ala
            195                 200                 205

Gly Cys Thr Cys Cys Gly Gly Thr Gly Gly Gly Cys Cys Gly Cys
        210                 215                 220

Gly Thr Cys Thr Gly Gly Thr Gly Cys Gly Gly Gly Cys Cys Cys
225                 230                 235                 240

Gly Gly Gly Ala Cys Cys Cys Ala Gly Cys Ala Gly Gly Cys Ala
                245                 250                 255

Gly Cys Cys Cys Gly Gly Ala Thr Gly Ala Gly Cys Cys Ala
            260                 265                 270

Gly Gly Cys Gly Gly Gly Ala Gly Cys Cys Gly Ala Cys Gly Gly Ala
            275                 280                 285

Gly Cys Cys Gly Cys Thr Thr Ala Cys Ala Cys Cys Cys Gly Cys
        290                 295                 300

Cys Gly Cys Cys Gly Gly Thr Gly Thr Cys Gly Cys Cys Gly Cys Gly
305                 310                 315                 320

Cys Thr Thr Cys Thr Cys Cys Thr Thr Cys Cys Cys Gly Gly Gly Gly
                325                 330                 335

Ala Cys Cys Ala Cys Cys Gly Gly Gly Thr Cys Cys Cys Thr Gly Gly
            340                 345                 350

Cys Gly Gly Cys Cys Gly Cys Cys Gly Cys Cys Gly Cys Cys Gly Cys
        355                 360                 365

Thr Gly Cys Cys Gly Cys Gly Gly Cys Cys Gly Gly Gly Ala Ala
        370                 375                 380

Gly Cys Thr Gly Cys Gly Gly Cys Cys Thr Ala Cys Ala Gly Cys Ala
385                 390                 395                 400

Gly Thr Gly Gly Cys Gly Gly Cys Gly Gly Ala Gly Cys Gly Gly Cys
            405                 410                 415

Gly Gly Gly Thr Gly Cys Gly Gly Gly Cys Cys Thr Gly Gly Cys Gly
            420                 425                 430

Gly Gly Cys Cys Gly Cys Gly Ala Gly Cys Ala Gly Thr Ala Cys Gly
        435                 440                 445

Gly Gly Gly Cys Gly Cys Gly Cys Gly Gly Cys Thr Thr Cys Gly Cys
        450                 455                 460

Gly Gly Gly Cys Thr Cys Cys Thr Ala Cys Thr Cys Ala Gly Cys
465                 470                 475                 480

Cys Cys Cys Thr Ala Cys Cys Cys Gly Gly Cys Thr Thr Ala Cys Ala
            485                 490                 495

Thr Gly Gly Cys Cys Gly Ala Cys Gly Thr Gly Gly Cys Gly Cys
        500                 505                 510

Gly Thr Cys Cys Thr Gly Gly Gly Cys Cys Gly Cys Ala Gly Cys Cys
        515                 520                 525

Gly Cys Cys Gly Cys Cys Gly Cys Thr Cys Cys Gly Cys Cys Gly
        530                 535                 540

Gly Cys Cys Cys Cys Thr Thr Cys Gly Ala Cys Ala Gly Cys Cys Cys
545                 550                 555                 560

-continued

Gly Gly Thr Cys Cys Thr Gly Cys Ala Cys Ala Gly Cys Cys Thr Gly
            565                 570                 575

Cys Cys Cys Gly Gly Cys Cys Gly Gly Gly Cys Cys Ala Ala Cys Cys
            580                 585                 590

Cys Gly Gly Cys Cys Gly Cys Cys Gly Ala Cys Ala Cys Cys Cys
            595                 600                 605

Cys Ala Ala Thr Cys Thr Cys Gly Ala Thr Ala Gly Thr Thr Thr
    610                 615                 620

Gly Ala Cys Gly Ala Cys Thr Thr Thr Cys Ala Gly Ala Ala Gly
625                 630                 635                 640

Gly Cys Ala Gly Ala Gly Ala Gly Thr Gly Thr Gly Thr Cys Ala Ala
                645                 650                 655

Cys Thr Gly Thr Gly Gly Gly Cys Thr Ala Thr Gly Thr Cys Cys
            660                 665                 670

Ala Cys Cys Cys Gly Cys Thr Cys Thr Gly Gly Ala Gly Gly Cys
    675                 680                 685

Gly Ala Gly Ala Thr Gly Gly Ala Cys Gly Gly Thr Cys Ala
    690                 695                 700

Cys Thr Ala Thr Cys Thr Gly Thr Gly Cys Ala Ala Cys Gly Cys Cys
705                 710                 715                 720

Thr Gly Cys Gly Gly Cys Cys Thr Cys Thr Ala Cys Ala Cys Ala
            725                 730                 735

Ala Gly Ala Thr Gly Ala Ala Cys Gly Gly Cys Ala Thr Cys Ala Ala
                740                 745                 750

Cys Cys Gly Gly Cys Cys Gly Cys Thr Cys Ala Thr Cys Ala Ala Gly
            755                 760                 765

Cys Cys Thr Cys Ala Gly Cys Gly Cys Cys Gly Gly Cys Thr Gly Thr
            770                 775                 780

Cys Cys Gly Gly Cys Thr Cys Cys Cys Gly Cys Gly Ala Gly Thr
785                 790                 795                 800

Gly Gly Gly Cys Cys Thr Cys Thr Cys Thr Gly Thr Gly Cys Cys
                805                 810                 815

Ala Ala Cys Thr Gly Cys Cys Ala Gly Ala Cys Cys Ala Cys Cys Ala
            820                 825                 830

Cys Cys Ala Cys Cys Ala Cys Gly Cys Thr Gly Thr Gly Gly Cys Gly
            835                 840                 845

Cys Cys Gly Cys Ala Ala Thr Gly Cys Gly Gly Ala Gly Gly Gly Cys
    850                 855                 860

Gly Ala Gly Cys Cys Thr Gly Thr Gly Thr Cys Ala Ala Thr Gly
865                 870                 875                 880

Cys Cys Thr Gly Cys Gly Gly Cys Cys Thr Cys Thr Ala Cys Ala Thr
            885                 890                 895

Gly Ala Ala Gly Cys Thr Cys Ala Cys Gly Gly Gly Thr Cys
    900                 905                 910

Cys Cys Cys Ala Gly Gly Cys Cys Thr Cys Thr Thr Gly Cys Ala Ala
            915                 920                 925

Thr Gly Cys Gly Gly Ala Ala Ala Gly Ala Gly Gly Gly Ala Thr
    930                 935                 940

Cys Cys Ala Ala Ala Cys Cys Ala Gly Ala Ala Ala Cys Gly Gly
945                 950                 955                 960

Ala Ala Gly Cys Cys Ala Ala Gly Ala Ala Cys Cys Thr Gly Ala
                965                 970                 975

Ala Thr Ala Ala Ala Thr Cys Thr Ala Ala Gly Ala Cys Ala Cys Cys

```
                  980             985             990
Ala Gly Cys Ala Gly Cys Thr Cys  Cys Thr Thr Cys Ala Gly Gly Cys
            995             1000            1005

Ala Gly Thr Gly Ala Gly Ala  Gly Cys Cys Thr Thr  Cys Cys Thr
    1010            1015            1020

Cys Cys Cys Gly Cys Cys Ala  Gly Cys Gly Gly Thr  Gly Cys Thr
    1025            1030            1035

Thr Cys Cys Ala Gly Cys Ala  Ala Cys Thr Cys Cys  Ala Gly Cys
    1040            1045            1050

Ala Ala Cys Gly Cys Cys Ala  Cys Cys Ala Cys Cys  Ala Gly Cys
    1055            1060            1065

Ala Gly Cys Ala Gly Cys Gly  Ala Gly Gly Ala Gly  Ala Thr Gly
    1070            1075            1080

Cys Gly Thr Cys Cys Cys Ala  Thr Cys Ala Ala Gly  Ala Cys Gly
    1085            1090            1095

Gly Ala Gly Cys Cys Thr Gly  Gly Cys Cys Thr Gly  Thr Cys Ala
    1100            1105            1110

Thr Cys Thr Cys Ala Cys Thr  Ala Cys Gly Gly Gly  Cys Ala Cys
    1115            1120            1125

Ala Gly Cys Ala Gly Cys Thr  Cys Cys Gly Thr Gly  Thr Cys Cys
    1130            1135            1140

Cys Ala Gly Ala Cys Gly Thr  Thr Cys Thr Cys Ala  Gly Thr Cys
    1145            1150            1155

Ala Gly Thr Gly Cys Gly Ala  Thr Gly Thr Cys Thr  Gly Gly Cys
    1160            1165            1170

Cys Ala Thr Gly Gly Gly Cys  Cys Cys Thr Cys Cys  Ala Thr Cys
    1175            1180            1185

Cys Ala Cys Cys Cys Thr Gly  Thr Cys Cys Thr Cys  Thr Cys Gly
    1190            1195            1200

Gly Cys Cys Cys Thr Gly Ala  Ala Gly Cys Thr Cys  Thr Cys Cys
    1205            1210            1215

Cys Cys Ala Cys Ala Ala Gly  Gly Cys Thr Ala Thr  Gly Cys Gly
    1220            1225            1230

Thr Cys Thr Cys Cys Cys Gly  Thr Cys Ala Gly Cys  Cys Ala Gly
    1235            1240            1245

Thr Cys Thr Cys Cys Ala Cys  Ala Gly Ala Cys Cys  Ala Gly Cys
    1250            1255            1260

Thr Cys Cys Ala Ala Gly Cys  Ala Gly Gly Ala Cys  Thr Cys Thr
    1265            1270            1275

Thr Gly Gly Ala Ala Cys Ala  Gly Cys Cys Thr Gly  Gly Thr Cys
    1280            1285            1290

Thr Thr Gly Gly Cys Cys Gly  Ala Cys Ala Gly Thr  Cys Ala Cys
    1295            1300            1305

Gly Gly Gly Gly Ala Cys Ala  Thr Ala Ala Thr Cys  Ala Cys Thr
    1310            1315            1320

Gly Cys Gly Thr Ala Ala
    1325

<210> SEQ ID NO 10
<211> LENGTH: 463
<212> TYPE: PRT
<213> ORGANISM: Homo sapiens

<400> SEQUENCE: 10
```

```
Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
            35                  40                  45

Asn Ser Thr Asn Lys Leu Phe Gln Tyr Ala Ser Thr Asp Met Asp Lys
            50                  55                  60

Val Leu Leu Lys Tyr Thr Glu Tyr Asn Glu Pro His Glu Ser Arg Thr
65                  70                  75                  80

Asn Ser Asp Ile Val Glu Ala Leu Asn Lys Lys Glu Asn Lys Gly Cys
                85                  90                  95

Glu Ser Pro Asp Pro Asp Ser Ser Tyr Ala Leu Thr Pro Arg Thr Glu
            100                 105                 110

Glu Lys Tyr Lys Lys Ile Asn Glu Glu Phe Asp Asn Met Ile Lys Ser
            115                 120                 125

His Lys Ile Pro Ala Val Pro Pro Asn Phe Glu Met Pro Val Ser
            130                 135                 140

Ile Pro Val Ser Ser His Asn Ser Leu Val Tyr Ser Asn Pro Val Ser
145                 150                 155                 160

Ser Leu Gly Asn Pro Asn Leu Leu Pro Leu Ala His Pro Ser Leu Gln
                165                 170                 175

Arg Asn Ser Met Ser Pro Gly Val Thr His Arg Pro Pro Ser Ala Gly
            180                 185                 190

Asn Thr Gly Gly Leu Met Gly Gly Asp Leu Thr Ser Gly Ala Gly Thr
            195                 200                 205

Ser Ala Gly Asn Gly Tyr Gly Asn Pro Arg Asn Ser Pro Gly Leu Leu
            210                 215                 220

Val Ser Pro Gly Asn Leu Asn Lys Asn Met Gln Ala Lys Ser Pro Pro
225                 230                 235                 240

Pro Met Asn Leu Gly Met Asn Asn Arg Lys Pro Asp Leu Arg Val Leu
            245                 250                 255

Ile Pro Pro Gly Ser Lys Asn Thr Met Pro Ser Val Asn Gln Arg Ile
            260                 265                 270

Asn Asn Ser Gln Ser Ala Gln Ser Leu Ala Thr Pro Val Val Ser Val
            275                 280                 285

Ala Thr Pro Thr Leu Pro Gly Gln Gly Met Gly Gly Tyr Pro Ser Ala
            290                 295                 300

Ile Ser Thr Thr Tyr Gly Thr Glu Tyr Ser Leu Ser Ser Ala Asp Leu
305                 310                 315                 320

Ser Ser Leu Ser Gly Phe Asn Thr Ala Ser Ala Leu His Leu Gly Ser
            325                 330                 335

Val Thr Gly Trp Gln Gln Gln His Leu His Asn Met Pro Pro Ser Ala
            340                 345                 350

Leu Ser Gln Leu Gly Ala Cys Thr Ser Thr His Leu Ser Gln Ser Ser
            355                 360                 365

Asn Leu Ser Leu Pro Ser Thr Gln Ser Leu Asn Ile Lys Ser Glu Pro
            370                 375                 380

Val Ser Pro Pro Arg Asp Arg Thr Thr Thr Pro Ser Arg Tyr Pro Gln
385                 390                 395                 400

His Thr Arg His Glu Ala Gly Arg Ser Pro Val Asp Ser Leu Ser Ser
                405                 410                 415

Cys Ser Ser Ser Tyr Asp Gly Ser Asp Arg Glu Asp His Arg Asn Glu
```

```
                    420                 425                 430
Phe His Ser Pro Ile Gly Leu Thr Arg Pro Ser Pro Asp Glu Arg Glu
            435                 440                 445

Ser Pro Ser Val Lys Arg Met Arg Leu Ser Glu Gly Trp Ala Thr
    450                 455                 460

<210> SEQ ID NO 11
<211> LENGTH: 1392
<212> TYPE: PRT
<213> ORGANISM: Homo sapiens

<400> SEQUENCE: 11

Ala Thr Gly Gly Gly Ala Gly Ala Ala Ala Ala Ala Gly Ala
1               5                   10                  15

Thr Thr Cys Ala Gly Ala Thr Thr Ala Cys Gly Ala Gly Ala Thr
                20                  25                  30

Thr Ala Thr Gly Gly Ala Thr Gly Ala Ala Cys Gly Thr Ala Ala Cys
            35                  40                  45

Ala Gly Ala Cys Ala Gly Gly Thr Gly Ala Cys Ala Thr Thr Ala
        50                  55                  60

Cys Ala Ala Gly Ala Gly Ala Ala Thr Thr Thr Gly Gly
65                  70                  75                  80

Gly Thr Thr Gly Ala Thr Gly Ala Ala Gly Ala Gly Gly Cys Thr
                85                  90                  95

Thr Ala Thr Gly Ala Gly Cys Thr Gly Ala Gly Cys Gly Thr Gly Cys
            100                 105                 110

Thr Gly Thr Gly Thr Gly Ala Cys Thr Gly Thr Gly Ala Gly Ala Thr
        115                 120                 125

Thr Gly Cys Gly Cys Thr Gly Ala Thr Cys Ala Thr Cys Thr Thr Cys
    130                 135                 140

Ala Ala Cys Ala Gly Cys Ala Cys Cys Ala Ala Cys Ala Ala Gly Cys
145                 150                 155                 160

Thr Gly Thr Thr Cys Cys Ala Gly Thr Ala Thr Gly Cys Cys Ala Gly
                165                 170                 175

Cys Ala Cys Cys Gly Ala Cys Ala Thr Gly Gly Ala Cys Ala Ala Ala
            180                 185                 190

Gly Thr Gly Cys Thr Thr Cys Thr Cys Ala Ala Gly Thr Ala Cys Ala
        195                 200                 205

Cys Gly Gly Ala Gly Thr Ala Cys Ala Ala Cys Gly Ala Gly Cys Cys
    210                 215                 220

Gly Cys Ala Thr Gly Ala Gly Ala Cys Cys Gly Gly Ala Cys Ala
225                 230                 235                 240

Ala Ala Cys Thr Cys Ala Gly Ala Cys Ala Thr Cys Gly Thr Gly Gly
                245                 250                 255

Ala Gly Gly Cys Ala Thr Thr Gly Ala Ala Cys Ala Ala Gly Ala Ala
            260                 265                 270

Ala Gly Ala Ala Ala Cys Ala Ala Ala Gly Gly Cys Thr Gly Thr
        275                 280                 285

Gly Ala Ala Ala Gly Cys Cys Cys Gly Ala Thr Cys Cys Cys Gly
    290                 295                 300

Ala Cys Thr Cys Cys Thr Cys Thr Ala Thr Gly Cys Ala Cys Thr
305                 310                 315                 320

Cys Ala Cys Cys Cys Ala Cys Gly Cys Ala Cys Thr Gly Ala Ala
                325                 330                 335
```

```
Gly Ala Ala Ala Ala Thr Ala Cys Ala Ala Ala Ala Ala
            340                 345                 350
Thr Thr Ala Ala Thr Gly Ala Ala Gly Ala Ala Thr Thr Gly Ala
            355                 360                 365
Thr Ala Ala Thr Ala Thr Gly Ala Thr Cys Ala Ala Gly Ala Gly Thr
    370                 375                 380
Cys Ala Thr Ala Ala Ala Thr Thr Cys Cys Thr Gly Cys Thr Gly
385                 390                 395                 400
Thr Thr Cys Cys Ala Cys Cys Thr Cys Cys Ala Ala Cys Thr Thr
                405                 410                 415
Cys Gly Ala Gly Ala Thr Gly Cys Cys Ala Gly Thr Cys Thr Cys Cys
            420                 425                 430
Ala Thr Cys Cys Cys Ala Gly Thr Gly Thr Cys Cys Ala Gly Cys Cys
        435                 440                 445
Ala Cys Ala Ala Cys Ala Gly Thr Thr Thr Gly Gly Thr Gly Thr Ala
        450                 455                 460
Cys Ala Gly Cys Ala Ala Cys Cys Thr Gly Thr Cys Ala Gly Cys
465                 470                 475                 480
Thr Cys Ala Cys Thr Gly Gly Ala Ala Cys Cys Cys Ala
            485                 490                 495
Ala Cys Cys Thr Ala Thr Thr Gly Cys Cys Ala Cys Thr Gly Gly Cys
        500                 505                 510
Thr Cys Ala Cys Cys Thr Thr Cys Thr Cys Thr Gly Cys Ala Gly
            515                 520                 525
Ala Gly Gly Ala Ala Thr Ala Gly Thr Ala Thr Gly Thr Cys Thr Cys
    530                 535                 540
Cys Thr Gly Gly Thr Gly Thr Ala Ala Cys Ala Cys Ala Thr Cys Gly
545                 550                 555                 560
Ala Cys Cys Thr Cys Ala Ala Gly Thr Gly Cys Ala Gly Gly Thr
            565                 570                 575
Ala Ala Cys Ala Cys Ala Gly Gly Thr Gly Thr Cys Thr Gly Ala
            580                 585                 590
Thr Gly Gly Gly Thr Gly Gly Ala Gly Ala Cys Cys Thr Cys Ala Cys
    595                 600                 605
Gly Thr Cys Thr Gly Gly Thr Gly Cys Ala Gly Cys Ala Cys Cys
    610                 615                 620
Ala Gly Thr Gly Cys Ala Gly Gly Gly Ala Ala Cys Gly Gly Gly Thr
625                 630                 635                 640
Ala Thr Gly Gly Cys Ala Ala Thr Cys Cys Cys Gly Ala Ala Ala
            645                 650                 655
Cys Thr Cys Ala Cys Cys Ala Gly Gly Thr Thr Gly Cys Thr Gly
            660                 665                 670
Gly Thr Cys Thr Cys Ala Cys Cys Thr Gly Gly Thr Ala Ala Cys Thr
        675                 680                 685
Thr Gly Ala Ala Cys Ala Ala Gly Ala Ala Thr Ala Thr Gly Cys Ala
    690                 695                 700
Ala Gly Cys Ala Ala Ala Thr Cys Thr Cys Cys Thr Cys Cys
705                 710                 715                 720
Cys Cys Ala Ala Thr Gly Ala Ala Thr Thr Ala Gly Gly Ala Ala
            725                 730                 735
Thr Gly Ala Ala Thr Ala Cys Cys Gly Thr Ala Ala Ala Cys Cys
            740                 745                 750
Ala Gly Ala Thr Cys Thr Cys Cys Gly Ala Gly Thr Thr Cys Thr Thr
```

-continued

```
              755                 760                 765
Ala Thr Thr Cys Cys Ala Cys Cys Ala Gly Cys Ala Gly Cys Ala
              770                 775                 780
Ala Gly Ala Ala Thr Ala Cys Gly Ala Thr Gly Cys Cys Ala Thr Cys
785                 790                 795                 800
Ala Gly Thr Gly Ala Ala Thr Cys Ala Ala Gly Gly Ala Thr Ala
                  805                 810                 815
Ala Ala Thr Ala Ala Cys Thr Cys Cys Ala Gly Thr Cys Gly Gly
              820                 825                 830
Cys Thr Cys Ala Gly Thr Cys Ala Thr Thr Gly Gly Cys Thr Ala Cys
                  835                 840                 845
Cys Cys Cys Ala Gly Thr Gly Gly Thr Thr Thr Cys Cys Gly Thr Ala
850                 855                 860
Gly Cys Ala Ala Cys Thr Cys Cys Thr Ala Cys Thr Thr Ala Cys
865                 870                 875                 880
Cys Ala Gly Gly Ala Cys Ala Ala Gly Gly Ala Ala Thr Gly Gly Gly
                  885                 890                 895
Ala Gly Gly Ala Thr Ala Thr Cys Cys Ala Thr Cys Ala Gly Cys Cys
                  900                 905                 910
Ala Thr Thr Thr Cys Ala Ala Cys Ala Ala Cys Ala Thr Ala Thr Gly
                  915                 920                 925
Gly Thr Ala Cys Cys Gly Ala Gly Thr Ala Cys Thr Cys Thr Cys Thr
              930                 935                 940
Gly Ala Gly Thr Ala Gly Thr Gly Cys Ala Gly Ala Cys Cys Thr Gly
945                 950                 955                 960
Thr Cys Ala Thr Cys Thr Cys Thr Gly Thr Cys Thr Gly Gly Thr
                  965                 970                 975
Thr Thr Ala Ala Cys Ala Cys Cys Gly Cys Cys Ala Gly Cys Gly Cys
                  980                 985                 990
Thr Cys Thr Thr Cys Ala Cys Cys  Thr Thr Gly Gly Thr  Thr Cys Ala
                  995                 1000                1005
Gly Thr  Ala Ala Cys Thr Gly  Gly Cys Thr Gly  Gly Cys Ala Ala
              1010                1015                1020
Cys Ala  Gly Cys Ala Ala Cys  Ala Cys Cys Thr Ala  Cys Ala Thr
              1025                1030                1035
Ala Ala  Cys Ala Thr Gly Cys  Cys Ala Cys Cys Ala  Thr Cys Thr
              1040                1045                1050
Gly Cys  Cys Cys Thr Cys Ala  Gly Thr Cys Ala Gly  Thr Thr Gly
              1055                1060                1065
Gly Gly Ala Gly Cys Thr Thr  Gly Cys Ala Cys Thr  Ala Gly Cys
              1070                1075                1080
Ala Cys  Thr Cys Ala Thr Thr  Thr Ala Thr Cys Thr  Cys Ala Gly
              1085                1090                1095
Ala Gly  Thr Thr Cys Ala Ala  Ala Thr Cys Thr Cys  Thr Cys Cys
              1100                1105                1110
Cys Thr  Gly Cys Cys Thr Cys  Thr Cys Ala Cys Thr  Cys Ala Ala
              1115                1120                1125
Ala Gly  Cys Cys Thr Cys Ala  Ala Cys Ala Thr Cys  Ala Ala Gly
              1130                1135                1140
Thr Cys  Ala Gly Ala Ala Cys  Cys Thr Gly Thr Thr  Thr Cys Thr
              1145                1150                1155
Cys Cys  Thr Cys Cys Thr Ala  Gly Ala Gly Ala Cys  Cys Gly Thr
              1160                1165                1170
```

Ala Cys Cys Ala Cys Cys Ala Cys Cys Cys Cys Thr Thr Cys Gly
    1175                1180                1185

Ala Gly Ala Thr Ala Cys Cys Ala Cys Ala Ala Cys Ala Cys
    1190                1195                1200

Ala Cys Gly Cys Gly Cys Cys Ala Cys Gly Ala Gly Gly Cys Gly
    1205                1210                1215

Gly Gly Gly Ala Gly Ala Thr Cys Thr Cys Cys Thr Gly Thr Thr
    1220                1225                1230

Gly Ala Cys Ala Gly Cys Thr Thr Gly Ala Gly Cys Ala Gly Cys
    1235                1240                1245

Thr Gly Thr Ala Gly Cys Ala Gly Thr Thr Cys Gly Thr Ala Cys
    1250                1255                1260

Gly Ala Cys Gly Gly Gly Ala Gly Cys Gly Ala Cys Cys Gly Ala
    1265                1270                1275

Gly Ala Gly Gly Ala Thr Cys Ala Cys Cys Gly Gly Ala Ala Cys
    1280                1285                1290

Gly Ala Ala Thr Thr Cys Cys Ala Cys Thr Cys Cys Cys Cys Cys
    1295                1300                1305

Ala Thr Thr Gly Gly Ala Cys Thr Cys Ala Cys Cys Ala Gly Ala
    1310                1315                1320

Cys Cys Thr Thr Cys Gly Cys Cys Gly Gly Ala Cys Gly Ala Ala
    1325                1330                1335

Ala Gly Gly Gly Ala Ala Ala Gly Thr Cys Cys Cys Thr Cys Ala
    1340                1345                1350

Gly Thr Cys Ala Ala Gly Cys Gly Cys Ala Thr Gly Cys Gly Ala
    1355                1360                1365

Cys Thr Thr Thr Cys Thr Gly Ala Ala Gly Gly Ala Thr Gly Gly
    1370                1375                1380

Gly Cys Ala Ala Cys Ala Gly Ala
    1385                1390

<210> SEQ ID NO 12
<211> LENGTH: 473
<212> TYPE: PRT
<213> ORGANISM: Homo sapiens

<400> SEQUENCE: 12

Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn Ser Thr Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ser Asp Ile Val Glu Thr Leu Arg Lys Lys Gly Leu Asn Gly Cys
                85                  90                  95

Asp Ser Pro Asp Pro Asp Ala Asp Ser Val Gly His Ser Pro Glu
            100                 105                 110

Ser Glu Asp Lys Tyr Arg Lys Ile Asn Glu Asp Ile Asp Leu Met Ile
        115                 120                 125

Ser Arg Gln Arg Leu Cys Ala Val Pro Pro Pro Asn Phe Glu Met Pro

```
            130                 135                 140
Val Ser Ile Pro Val Ser Ser His Asn Ser Leu Val Tyr Ser Asn Pro
145                 150                 155                 160

Val Ser Ser Leu Gly Asn Pro Asn Leu Leu Pro Leu Ala His Pro Ser
                165                 170                 175

Leu Gln Arg Asn Ser Met Ser Pro Gly Val Thr His Arg Pro Pro Ser
            180                 185                 190

Ala Gly Asn Thr Gly Gly Leu Met Gly Gly Asp Leu Thr Ser Gly Ala
        195                 200                 205

Gly Thr Ser Ala Gly Asn Gly Tyr Gly Asn Pro Arg Asn Ser Pro Gly
    210                 215                 220

Leu Leu Val Ser Pro Gly Asn Leu Asn Lys Asn Met Gln Ala Lys Ser
225                 230                 235                 240

Pro Pro Pro Met Asn Leu Gly Met Asn Asn Arg Lys Pro Asp Leu Arg
                245                 250                 255

Val Leu Ile Pro Pro Gly Ser Lys Asn Thr Met Pro Ser Val Ser Glu
            260                 265                 270

Asp Val Asp Leu Leu Leu Asn Gln Arg Ile Asn Asn Ser Gln Ser Ala
        275                 280                 285

Gln Ser Leu Ala Thr Pro Val Val Ser Val Ala Thr Pro Thr Leu Pro
    290                 295                 300

Gly Gln Gly Met Gly Gly Tyr Pro Ser Ala Ile Ser Thr Thr Tyr Gly
305                 310                 315                 320

Thr Glu Tyr Ser Leu Ser Ser Ala Asp Leu Ser Ser Leu Ser Gly Phe
                325                 330                 335

Asn Thr Ala Ser Ala Leu His Leu Gly Ser Val Thr Gly Trp Gln Gln
            340                 345                 350

Gln His Leu His Asn Met Pro Pro Ser Ala Leu Ser Gln Leu Gly Ala
        355                 360                 365

Cys Thr Ser Thr His Leu Ser Gln Ser Ser Asn Leu Ser Leu Pro Ser
    370                 375                 380

Thr Gln Ser Leu Asn Ile Lys Ser Glu Pro Val Ser Pro Pro Arg Asp
385                 390                 395                 400

Arg Thr Thr Thr Pro Ser Arg Tyr Pro Gln His Thr Arg His Glu Ala
                405                 410                 415

Gly Arg Ser Pro Val Asp Ser Leu Ser Ser Cys Ser Ser Ser Tyr Asp
            420                 425                 430

Gly Ser Asp Arg Glu Asp His Arg Asn Glu Phe His Ser Pro Ile Gly
        435                 440                 445

Leu Thr Arg Pro Ser Pro Asp Glu Arg Glu Ser Pro Ser Val Lys Arg
    450                 455                 460

Met Arg Leu Ser Glu Gly Trp Ala Thr
465                 470

<210> SEQ ID NO 13
<211> LENGTH: 1422
<212> TYPE: PRT
<213> ORGANISM: Homo sapiens

<400> SEQUENCE: 13

Ala Thr Gly Gly Gly Ala Gly Ala Ala Ala Ala Gly Ala
1               5                   10                  15

Thr Thr Cys Ala Gly Ala Thr Thr Ala Cys Gly Ala Gly Gly Ala Thr
                20                  25                  30
```

-continued

```
Thr Ala Thr Gly Gly Ala Thr Gly Ala Ala Cys Gly Thr Ala Ala Cys
        35                  40                  45

Ala Gly Ala Cys Ala Gly Gly Thr Gly Ala Cys Ala Thr Thr Thr Ala
    50                  55                  60

Cys Ala Ala Ala Gly Ala Gly Gly Ala Ala Ala Thr Thr Thr Gly Gly
65                  70                  75                  80

Gly Thr Thr Gly Ala Thr Gly Ala Ala Gly Ala Ala Gly Gly Cys Thr
                85                  90                  95

Thr Ala Thr Gly Ala Gly Cys Thr Gly Ala Gly Cys Gly Thr Gly Cys
            100                 105                 110

Thr Gly Thr Gly Thr Gly Ala Cys Thr Gly Thr Gly Ala Gly Ala Thr
        115                 120                 125

Thr Gly Cys Gly Cys Thr Gly Ala Thr Cys Ala Thr Cys Thr Thr Cys
    130                 135                 140

Ala Ala Cys Ala Gly Cys Ala Cys Cys Ala Ala Cys Ala Ala Gly Cys
145                 150                 155                 160

Thr Gly Thr Thr Cys Cys Ala Gly Thr Ala Thr Gly Cys Cys Ala Gly
                165                 170                 175

Cys Ala Cys Cys Gly Ala Cys Ala Thr Gly Gly Ala Cys Ala Ala Ala
            180                 185                 190

Gly Thr Gly Cys Thr Thr Cys Thr Cys Ala Ala Gly Thr Ala Cys Ala
        195                 200                 205

Cys Gly Gly Ala Gly Thr Ala Cys Ala Ala Cys Gly Ala Gly Cys Cys
    210                 215                 220

Gly Cys Ala Thr Gly Ala Gly Ala Gly Cys Cys Gly Gly Ala Cys Ala
225                 230                 235                 240

Ala Ala Cys Thr Cys Ala Gly Ala Cys Ala Thr Cys Gly Thr Gly Gly
                245                 250                 255

Ala Gly Ala Cys Gly Thr Thr Gly Ala Gly Ala Ala Ala Gly Ala Ala
            260                 265                 270

Gly Gly Gly Cys Cys Thr Thr Ala Ala Thr Gly Gly Cys Thr Gly Thr
        275                 280                 285

Gly Ala Cys Ala Gly Cys Cys Cys Ala Gly Ala Cys Cys Cys Cys Gly
    290                 295                 300

Ala Thr Gly Cys Gly Gly Ala Cys Gly Ala Thr Thr Cys Cys Gly Thr
305                 310                 315                 320

Ala Gly Gly Thr Cys Ala Cys Ala Gly Cys Cys Cys Thr Gly Ala Gly
                325                 330                 335

Thr Cys Thr Gly Ala Gly Gly Ala Cys Ala Ala Gly Thr Ala Cys Ala
            340                 345                 350

Gly Gly Ala Ala Ala Ala Thr Thr Ala Ala Cys Gly Ala Ala Gly Ala
        355                 360                 365

Thr Ala Thr Thr Gly Ala Thr Cys Thr Ala Ala Thr Gly Ala Thr Cys
    370                 375                 380

Ala Gly Cys Ala Gly Gly Cys Ala Ala Ala Gly Ala Thr Thr Gly Thr
385                 390                 395                 400

Gly Thr Gly Cys Thr Gly Thr Thr Cys Cys Ala Cys Cys Thr Cys Cys
                405                 410                 415

Cys Ala Ala Cys Thr Thr Cys Gly Ala Gly Ala Thr Gly Cys Cys Ala
            420                 425                 430

Gly Thr Cys Thr Cys Cys Ala Thr Cys Cys Cys Ala Gly Thr Gly Thr
        435                 440                 445

Cys Cys Ala Gly Cys Cys Ala Cys Ala Ala Cys Ala Gly Thr Thr Thr
```

```
            450                 455                 460
Gly Gly Thr Gly Thr Ala Cys Ala Gly Cys Ala Ala Cys Cys Cys Thr
465                 470                 475                 480

Gly Thr Cys Ala Gly Cys Thr Cys Ala Cys Thr Gly Gly Gly Ala Ala
                485                 490                 495

Ala Cys Cys Cys Cys Ala Ala Cys Cys Thr Ala Thr Thr Gly Cys Cys
                500                 505                 510

Ala Cys Thr Gly Gly Cys Thr Cys Ala Cys Cys Thr Thr Cys Thr
    515                 520                 525

Cys Thr Gly Cys Ala Gly Ala Gly Gly Ala Ala Thr Ala Gly Thr Ala
        530                 535                 540

Thr Gly Thr Cys Thr Cys Thr Gly Gly Thr Gly Thr Ala Ala Cys
545                 550                 555                 560

Ala Cys Ala Thr Cys Gly Ala Cys Cys Thr Cys Cys Ala Ala Gly Thr
                565                 570                 575

Gly Cys Ala Gly Gly Thr Ala Ala Cys Ala Cys Ala Gly Gly Thr Gly
                580                 585                 590

Gly Thr Cys Thr Gly Ala Thr Gly Gly Gly Thr Gly Gly Ala Gly Ala
                595                 600                 605

Cys Cys Thr Cys Ala Cys Gly Thr Cys Thr Gly Gly Thr Gly Cys Ala
        610                 615                 620

Gly Gly Cys Ala Cys Cys Ala Gly Thr Gly Cys Ala Gly Gly Gly Ala
625                 630                 635                 640

Ala Cys Gly Gly Gly Thr Ala Thr Gly Gly Cys Ala Ala Thr Cys Cys
                645                 650                 655

Cys Cys Gly Ala Ala Ala Cys Thr Cys Ala Cys Cys Ala Gly Gly Thr
                660                 665                 670

Cys Thr Gly Cys Thr Gly Gly Thr Cys Thr Cys Ala Cys Cys Thr Gly
        675                 680                 685

Gly Thr Ala Ala Cys Thr Thr Gly Ala Ala Cys Ala Ala Gly Ala Ala
                690                 695                 700

Thr Ala Thr Gly Cys Ala Ala Gly Cys Ala Ala Ala Thr Cys Thr
705                 710                 715                 720

Cys Cys Thr Cys Cys Cys Cys Ala Ala Thr Gly Ala Ala Thr Thr
                725                 730                 735

Thr Ala Gly Gly Ala Ala Thr Gly Ala Ala Thr Ala Ala Cys Cys Gly
                740                 745                 750

Thr Ala Ala Ala Cys Cys Ala Gly Ala Thr Cys Thr Cys Cys Gly Ala
                755                 760                 765

Gly Thr Thr Cys Thr Thr Ala Thr Thr Cys Ala Cys Ala Cys Ala Gly
        770                 775                 780

Gly Cys Ala Gly Cys Ala Ala Gly Ala Ala Thr Ala Cys Gly Ala Thr
785                 790                 795                 800

Gly Cys Cys Ala Thr Cys Ala Gly Thr Gly Thr Cys Thr Gly Ala Gly
                805                 810                 815

Gly Ala Thr Gly Thr Cys Gly Ala Cys Cys Thr Gly Cys Thr Thr Thr
                820                 825                 830

Thr Gly Ala Ala Thr Cys Ala Ala Ala Gly Gly Ala Thr Ala Ala Ala
        835                 840                 845

Thr Ala Ala Cys Thr Cys Cys Cys Ala Gly Thr Cys Gly Gly Cys Thr
        850                 855                 860

Cys Ala Gly Thr Cys Ala Thr Thr Gly Gly Cys Thr Ala Cys Cys Cys
865                 870                 875                 880
```

-continued

```
Cys Ala Gly Thr Gly Gly Thr Thr Thr Cys Cys Gly Thr Ala Gly Cys
                885                 890                 895

Ala Ala Cys Thr Cys Cys Thr Ala Cys Thr Thr Thr Ala Cys Cys Ala
            900                 905                 910

Gly Gly Ala Cys Ala Ala Gly Gly Ala Ala Thr Gly Gly Gly Ala Gly
        915                 920                 925

Gly Ala Thr Ala Thr Cys Cys Ala Thr Cys Ala Gly Cys Cys Ala Thr
    930                 935                 940

Thr Thr Cys Ala Ala Cys Ala Ala Cys Ala Thr Ala Thr Gly Gly Thr
945                 950                 955                 960

Ala Cys Cys Gly Ala Gly Thr Ala Cys Thr Cys Thr Cys Thr Gly Ala
                965                 970                 975

Gly Thr Ala Gly Thr Gly Cys Ala Gly Ala Cys Cys Thr Gly Thr Cys
            980                 985                 990

Ala Thr Cys Thr Cys Thr Gly Thr  Cys Thr Gly Gly Gly  Thr Thr Thr
        995                 1000                1005

Ala Ala  Cys Ala Cys Cys Gly  Cys Cys Ala Gly Cys  Gly Cys Thr
    1010                 1015                 1020

Cys Thr  Thr Cys Ala Cys Cys  Thr Thr Gly Gly Thr  Thr Cys Ala
    1025                 1030                 1035

Gly Thr  Ala Ala Cys Thr Gly  Gly Cys Thr Gly Gly  Cys Ala Ala
    1040                 1045                 1050

Cys Ala  Gly Cys Ala Ala Cys  Ala Cys Cys Thr Ala  Cys Ala Thr
    1055                 1060                 1065

Ala Ala  Cys Ala Thr Gly Cys  Cys Ala Cys Cys Ala  Thr Cys Thr
    1070                 1075                 1080

Gly Cys  Cys Cys Thr Cys Ala  Gly Thr Cys Ala Gly  Thr Thr Gly
    1085                 1090                 1095

Gly Gly  Ala Gly Cys Thr Thr  Gly Cys Ala Cys Thr  Ala Gly Cys
    1100                 1105                 1110

Ala Cys  Thr Cys Ala Thr Thr  Thr Ala Thr Cys Thr  Cys Ala Gly
    1115                 1120                 1125

Ala Gly  Thr Thr Cys Ala Ala  Ala Thr Cys Thr Cys  Thr Cys Cys
    1130                 1135                 1140

Cys Thr  Gly Cys Cys Thr Thr  Cys Thr Ala Cys Thr  Cys Ala Ala
    1145                 1150                 1155

Ala Gly  Cys Cys Thr Cys Ala  Ala Cys Ala Thr Cys  Ala Ala Gly
    1160                 1165                 1170

Thr Cys  Ala Gly Ala Ala Cys  Cys Thr Gly Thr Thr  Thr Cys Thr
    1175                 1180                 1185

Cys Cys  Thr Cys Cys Thr Ala  Gly Ala Gly Ala Cys  Cys Gly Thr
    1190                 1195                 1200

Ala Cys  Cys Ala Cys Cys Ala  Cys Cys Cys Cys Thr  Thr Cys Gly
    1205                 1210                 1215

Ala Gly  Ala Thr Ala Cys Cys  Cys Ala Cys Ala Ala  Cys Ala Cys
    1220                 1225                 1230

Ala Cys  Gly Cys Gly Cys Cys  Ala Cys Gly Ala Gly  Gly Cys Gly
    1235                 1240                 1245

Gly Gly  Gly Ala Gly Ala Thr  Cys Thr Cys Cys Thr  Gly Thr Thr
    1250                 1255                 1260

Gly Ala  Cys Ala Gly Cys Thr  Thr Gly Ala Gly Cys  Ala Gly Cys
    1265                 1270                 1275
```

```
Thr Gly Thr Ala Gly Cys Ala Gly Thr Cys Gly Thr Ala Cys
    1280            1285            1290

Gly Ala Cys Gly Gly Ala Gly Cys Gly Ala Cys Cys Gly Ala
    1295            1300            1305

Gly Ala Gly Gly Ala Thr Cys Ala Cys Cys Gly Ala Ala Cys
    1310            1315            1320

Gly Ala Ala Thr Thr Cys Cys Ala Cys Thr Cys Cys Cys Cys
    1325            1330            1335

Ala Thr Thr Gly Gly Ala Cys Thr Cys Ala Cys Cys Ala Gly Ala
    1340            1345            1350

Cys Cys Thr Thr Cys Gly Cys Cys Gly Gly Ala Cys Gly Ala Ala
    1355            1360            1365

Ala Gly Gly Gly Ala Ala Gly Thr Cys Cys Cys Thr Cys Ala
    1370            1375            1380

Gly Thr Cys Ala Ala Gly Cys Gly Cys Ala Thr Gly Cys Gly Ala
    1385            1390            1395

Cys Thr Thr Thr Cys Thr Gly Ala Ala Gly Gly Ala Thr Gly Gly
    1400            1405            1410

Gly Cys Ala Ala Cys Ala Thr Gly Ala
    1415            1420

<210> SEQ ID NO 14
<211> LENGTH: 513
<212> TYPE: PRT
<213> ORGANISM: Homo sapiens

<400> SEQUENCE: 14

Met Ala Asp Ala Asp Glu Ala Leu Ala Gly His Leu Trp Ser Leu
1               5                   10                  15

Thr Gln Lys Thr Cys Leu Arg Phe Glu Pro Arg Ala Arg Ser Gly Pro
                20                  25                  30

Pro Ala Ser Pro Pro Gly Arg Pro Arg Ser Arg Leu His Pro Ala Gly
            35                  40                  45

Met Glu Gly Ile Lys Val Phe Leu His Glu Arg Glu Leu Trp Leu Lys
50                  55                  60

Phe His Glu Val Thr Glu Met Ile Ile Thr Lys Ala Gly Arg Arg Met
65                  70                  75                  80

Phe Pro Ser Tyr Lys Val Lys Val Thr Gly Ile Asn Pro Lys Thr Lys
                85                  90                  95

Tyr Ile Leu Leu Met Asp Ile Val Pro Ala Asp Asp His Arg Tyr Lys
            100                 105                 110

Phe Ala Asp Asn Lys Trp Cys Val Thr Gly Lys Ala Glu Pro Ala Met
        115                 120                 125

Ala Gly Arg Leu Tyr Val His Pro Asp Ser Pro Ala Thr Gly Ala His
    130                 135                 140

Trp Met Arg Gln Leu Val Ser Phe Gln Lys Leu Lys Leu Thr Asn Asn
145                 150                 155                 160

His Leu Asp Pro Phe Gly His Ile Ile Leu Asn Ser Met His Lys Tyr
                165                 170                 175

Gln Pro Arg Leu His Ile Val Lys Ala Asp Glu Asn Asn Gly Phe Gly
            180                 185                 190

Ser Lys Asn Thr Ala Phe Cys Thr His Val Phe Pro Glu Thr Ala Phe
        195                 200                 205

Ile Ala Val Thr Ser Tyr Gln Asn His Lys Ile Thr Gln Leu Lys Ile
    210                 215                 220
```

```
Glu Asn Asn Pro Phe Ala Lys Gly Phe Arg Gly Ser Asp Asp Met Glu
225                 230                 235                 240

Leu His Arg Met Ser Arg Met Gln Ser Lys Glu Tyr Pro Val Val Pro
            245                 250                 255

Arg Ser Thr Val Arg Gln Lys Val Ala Ser Asn His Ser Pro Phe Ser
        260                 265                 270

Ser Glu Ser Arg Ala Leu Ser Thr Ser Ser Asn Leu Gly Ser Gln Tyr
    275                 280                 285

Gln Cys Glu Asn Gly Val Ser Gly Pro Ser Gln Asp Leu Leu Pro Pro
290                 295                 300

Pro Asn Pro Tyr Pro Leu Pro Gln Glu His Ser Gln Ile Tyr His Cys
305                 310                 315                 320

Thr Lys Arg Lys Glu Glu Glu Cys Ser Thr Thr Asp His Pro Tyr Lys
                325                 330                 335

Lys Pro Tyr Met Glu Thr Ser Pro Ser Glu Glu Asp Ser Phe Tyr Arg
            340                 345                 350

Ser Ser Tyr Pro Gln Gln Gln Gly Leu Gly Ala Ser Tyr Arg Thr Glu
        355                 360                 365

Ser Ala Gln Arg Gln Ala Cys Met Tyr Ala Ser Ser Ala Pro Pro Ser
370                 375                 380

Glu Pro Val Pro Ser Leu Glu Asp Ile Ser Cys Asn Thr Trp Pro Ser
385                 390                 395                 400

Met Pro Ser Tyr Ser Ser Cys Thr Val Thr Val Gln Pro Trp Thr
                405                 410                 415

Gly Tyr Pro Thr Ser Thr Ser Pro Leu Thr Ser Pro Arg Gly Pro Trp
            420                 425                 430

Ser Leu Gly Trp Leu Ala Trp Gln Pro Trp Leu Pro Thr Ala Gly Arg
        435                 440                 445

Gly Asn Val Pro Ser Thr Arg Pro Pro Val Ala His Gln Pro Val Val
450                 455                 460

Ser Ser Val Gly Pro Gln Thr Gly Leu Gln Ser Pro Gly Thr Leu Gln
465                 470                 475                 480

Pro Pro Glu Phe Leu Tyr Ser His Gly Val Gly Leu Tyr Pro Leu
                485                 490                 495

Ile Ser Thr Thr Leu Cys Thr Glu Leu Ala Trp Cys Arg Val Glu Arg
            500                 505                 510

Gln

<210> SEQ ID NO 15
<211> LENGTH: 1542
<212> TYPE: PRT
<213> ORGANISM: Homo sapiens

<400> SEQUENCE: 15

Ala Thr Gly Gly Cys Cys Gly Ala Cys Gly Cys Ala Gly Ala Cys Gly
1               5                   10                  15

Ala Gly Gly Cys Thr Thr Thr Gly Cys Thr Gly Gly Cys Gly Cys
            20                  25                  30

Ala Cys Ala Cys Thr Cys Thr Gly Gly Ala Gly Cys Cys Thr Gly
        35                  40                  45

Ala Cys Gly Cys Ala Ala Ala Gly Ala Cys Cys Thr Gly Cys Cys
    50                  55                  60

Thr Gly Cys Gly Ala Thr Thr Cys Gly Ala Ala Cys Cys Gly Ala Gly
65                  70                  75                  80
```

```
Ala Gly Cys Gly Cys Gly Cys Thr Cys Gly Gly Gly Gly Cys Cys Cys
                85                  90                  95

Cys Cys Ala Gly Cys Ala Ala Gly Thr Cys Cys Cys Cys Cys Cys Gly
            100                 105                 110

Gly Thr Cys Gly Thr Cys Cys Cys Cys Gly Cys Ala Gly Cys Cys Gly
        115                 120                 125

Cys Cys Thr Thr Cys Ala Cys Cys Cys Ala Gly Cys Ala Gly Gly Cys
    130                 135                 140

Ala Thr Gly Gly Ala Gly Gly Gly Ala Ala Thr Cys Ala Ala Ala Gly
145                 150                 155                 160

Thr Gly Thr Thr Thr Cys Thr Cys Cys Ala Thr Gly Ala Ala Ala Gly
                165                 170                 175

Ala Gly Ala Ala Cys Thr Gly Thr Gly Gly Cys Thr Ala Ala Ala Ala
            180                 185                 190

Thr Thr Cys Cys Ala Cys Gly Ala Ala Gly Thr Cys Ala Cys Gly Gly
        195                 200                 205

Ala Ala Ala Thr Gly Ala Thr Cys Ala Thr Ala Ala Cys Cys Ala Ala
    210                 215                 220

Gly Gly Cys Thr Gly Gly Ala Ala Gly Gly Cys Gly Gly Ala Thr Gly
225                 230                 235                 240

Thr Thr Thr Cys Cys Cys Ala Gly Thr Thr Ala Cys Ala Ala Ala Gly
                245                 250                 255

Thr Gly Ala Ala Gly Gly Thr Gly Ala Cys Gly Gly Gly Cys Ala Thr
            260                 265                 270

Thr Ala Ala Thr Cys Cys Cys Ala Ala Ala Ala Cys Gly Ala Ala Gly
        275                 280                 285

Thr Ala Cys Ala Thr Thr Cys Thr Thr Cys Thr Cys Ala Thr Gly Gly
    290                 295                 300

Ala Cys Ala Thr Thr Gly Thr Ala Cys Cys Thr Gly Cys Gly Gly Ala
305                 310                 315                 320

Cys Gly Ala Thr Cys Ala Cys Ala Gly Ala Thr Ala Cys Ala Ala Ala
                325                 330                 335

Thr Thr Cys Gly Cys Ala Gly Ala Thr Ala Ala Thr Ala Ala Ala Thr
            340                 345                 350

Gly Gly Thr Gly Thr Gly Thr Gly Ala Cys Gly Gly Gly Cys Ala Ala
        355                 360                 365

Ala Gly Cys Thr Gly Ala Gly Cys Cys Cys Gly Cys Cys Ala Thr Gly
    370                 375                 380

Gly Cys Thr Gly Gly Cys Cys Gly Cys Cys Thr Gly Thr Ala Cys Gly
385                 390                 395                 400

Thr Gly Cys Ala Cys Cys Cys Ala Gly Ala Cys Thr Cys Cys Cys Cys
                405                 410                 415

Cys Gly Cys Cys Ala Cys Cys Gly Gly Gly Gly Cys Gly Cys Ala Thr
            420                 425                 430

Thr Gly Gly Ala Thr Gly Ala Gly Gly Cys Ala Gly Cys Thr Cys Gly
        435                 440                 445

Thr Cys Thr Cys Cys Thr Thr Cys Cys Ala Gly Ala Ala Ala Cys Thr
    450                 455                 460

Cys Ala Ala Gly Cys Thr Cys Ala Cys Cys Ala Ala Cys Ala Ala Cys
465                 470                 475                 480

Cys Ala Cys Cys Thr Gly Gly Ala Cys Cys Cys Ala Thr Thr Thr Gly
                485                 490                 495
```

```
Gly Gly Cys Ala Thr Ala Thr Thr Ala Thr Cys Thr Ala Ala Ala
            500                 505                 510
Thr Thr Cys Cys Ala Thr Gly Cys Ala Cys Ala Ala Thr Ala Cys
            515                 520                 525
Cys Ala Gly Cys Cys Thr Ala Gly Ala Thr Thr Ala Cys Ala Cys Ala
            530                 535                 540
Thr Cys Gly Thr Gly Ala Ala Gly Cys Gly Gly Ala Thr Gly Ala
545                 550                 555                 560
Ala Ala Ala Thr Ala Ala Thr Gly Gly Ala Thr Thr Thr Gly Gly Cys
                565                 570                 575
Thr Cys Ala Ala Ala Ala Ala Thr Ala Cys Ala Gly Cys Gly Thr
            580                 585                 590
Thr Cys Thr Gly Cys Ala Cys Thr Cys Ala Cys Gly Thr Cys Thr Thr
            595                 600                 605
Thr Cys Cys Thr Gly Ala Gly Ala Cys Thr Gly Cys Gly Thr Thr Thr
            610                 615                 620
Ala Thr Ala Gly Cys Ala Gly Thr Gly Ala Cys Thr Cys Cys Thr
625                 630                 635                 640
Ala Cys Cys Ala Gly Ala Ala Cys Cys Ala Cys Ala Ala Gly Ala Thr
                645                 650                 655
Cys Ala Cys Gly Cys Ala Ala Thr Thr Ala Ala Ala Gly Ala Thr Thr
            660                 665                 670
Gly Ala Gly Ala Ala Thr Ala Ala Thr Cys Cys Thr Thr Thr Gly
            675                 680                 685
Cys Cys Ala Ala Ala Gly Gly Ala Thr Thr Thr Cys Gly Gly Gly Gly
            690                 695                 700
Cys Ala Gly Thr Gly Ala Thr Gly Ala Cys Ala Thr Gly Gly Ala Gly
705                 710                 715                 720
Cys Thr Gly Cys Ala Cys Ala Gly Ala Ala Thr Gly Thr Cys Ala Ala
                725                 730                 735
Gly Ala Ala Thr Gly Cys Ala Ala Ala Gly Thr Ala Ala Ala Gly Ala
                740                 745                 750
Ala Thr Ala Thr Cys Cys Cys Gly Thr Gly Gly Thr Cys Cys Cys Cys
            755                 760                 765
Ala Gly Gly Ala Gly Cys Ala Cys Cys Gly Thr Gly Ala Gly Gly Cys
            770                 775                 780
Ala Ala Ala Ala Ala Gly Thr Gly Gly Cys Cys Thr Cys Cys Ala Ala
785                 790                 795                 800
Cys Cys Ala Cys Ala Gly Thr Cys Cys Thr Thr Thr Cys Ala Gly Cys
                805                 810                 815
Ala Gly Cys Gly Ala Gly Thr Cys Thr Cys Gly Ala Gly Cys Thr Cys
                820                 825                 830
Thr Cys Thr Cys Cys Ala Cys Cys Thr Cys Ala Thr Cys Cys Ala Ala
            835                 840                 845
Thr Thr Thr Gly Gly Gly Gly Thr Cys Cys Ala Ala Thr Ala Cys
            850                 855                 860
Cys Ala Gly Thr Gly Thr Gly Ala Gly Ala Ala Thr Gly Gly Thr Gly
865                 870                 875                 880
Thr Thr Thr Cys Cys Gly Gly Cys Cys Cys Thr Cys Cys Ala
                885                 890                 895
Gly Gly Ala Cys Cys Thr Cys Thr Gly Cys Cys Thr Cys Cys Ala
            900                 905                 910
Cys Cys Cys Ala Ala Cys Cys Cys Ala Thr Ala Cys Cys Cys Ala Cys
```

-continued

```
        915                 920                 925

Thr Gly Cys Cys Cys Cys Ala Gly Gly Ala Gly Cys Ala Thr Ala Gly
    930                 935                 940

Cys Cys Ala Ala Ala Thr Thr Thr Ala Cys Cys Ala Thr Thr Gly Thr
945                 950                 955                 960

Ala Cys Cys Ala Ala Gly Ala Gly Gly Ala Ala Ala Gly Ala Gly Gly
                965                 970                 975

Ala Ala Gly Ala Ala Thr Gly Thr Thr Cys Cys Ala Cys Cys Ala Cys
            980                 985                 990

Ala Gly Ala Cys Cys Ala Thr Cys  Cys Cys Thr Ala Thr  Ala Ala Gly
        995                 1000                1005

Ala Ala  Gly Cys Cys Cys Thr  Ala Cys Ala Thr Gly  Gly Ala Gly
    1010                1015                1020

Ala Cys  Ala Thr Cys Ala Cys  Cys Cys Ala Gly Thr  Gly Ala Ala
    1025                1030                1035

Gly Ala  Ala Gly Ala Thr Thr  Cys Cys Thr Thr Cys  Thr Ala Cys
    1040                1045                1050

Cys Gly  Cys Thr Cys Thr Ala  Gly Cys Thr Ala Thr  Cys Cys Ala
    1055                1060                1065

Cys Ala  Gly Cys Ala Gly Cys  Ala Gly Gly Gly Cys  Cys Thr Gly
    1070                1075                1080

Gly Gly  Thr Gly Cys Cys Thr  Cys Cys Thr Ala Cys  Ala Gly Gly
    1085                1090                1095

Ala Cys  Ala Gly Ala Gly Thr  Cys Gly Gly Cys Ala  Cys Ala Gly
    1100                1105                1110

Cys Gly  Gly Cys Ala Ala Gly  Cys Thr Thr Gly Cys  Ala Thr Gly
    1115                1120                1125

Thr Ala  Thr Gly Cys Cys Ala  Gly Cys Thr Cys Thr  Gly Cys Gly
    1130                1135                1140

Cys Cys  Cys Cys Cys Cys Ala  Gly Cys Gly Ala Gly  Cys Cys Thr
    1145                1150                1155

Gly Thr  Gly Cys Cys Cys Ala  Gly Cys Cys Thr Ala  Gly Ala Gly
    1160                1165                1170

Gly Ala  Cys Ala Thr Cys Ala  Gly Cys Thr Gly Cys  Ala Ala Cys
    1175                1180                1185

Ala Cys  Gly Thr Gly Gly Cys  Cys Ala Ala Gly Cys  Ala Thr Gly
    1190                1195                1200

Cys Cys  Thr Thr Cys Cys Thr  Ala Cys Ala Gly Cys  Ala Gly Cys
    1205                1210                1215

Thr Gly  Cys Ala Cys Cys Gly  Thr Cys Ala Cys Cys  Ala Cys Cys
    1220                1225                1230

Gly Thr  Gly Cys Ala Gly Cys  Cys Ala Thr Gly Gly  Ala Cys Ala
    1235                1240                1245

Gly Gly  Cys Thr Ala Cys Cys  Cys Thr Ala Cys Cys  Ala Gly Cys
    1250                1255                1260

Ala Cys  Thr Thr Cys Thr Cys  Cys Gly Cys Thr Cys  Ala Cys Thr
    1265                1270                1275

Thr Cys  Ala Cys Cys Thr Cys  Gly Gly Gly Gly Cys  Cys Cys Cys
    1280                1285                1290

Thr Gly  Gly Thr Cys Cys Cys  Thr Cys Gly Gly Cys  Thr Gly Gly
    1295                1300                1305

Cys Thr  Gly Gly Cys Ala Thr  Gly Gly Cys Ala Ala  Cys Cys Ala
    1310                1315                1320
```

-continued

```
Thr Gly Gly Cys Thr Cys Cys Cys Ala Cys Ala Gly Cys Thr
    1325                1330                1335

Gly Gly Gly Ala Gly Ala Gly Gly Ala Ala Thr Gly Thr Thr
    1340                1345                1350

Cys Cys Cys Ala Gly Cys Ala Cys Cys Ala Gly Ala Cys Cys Thr
    1355                1360                1365

Cys Cys Cys Gly Thr Gly Gly Cys Cys Ala Cys Cys Ala Gly
    1370                1375                1380

Cys Cys Thr Gly Thr Gly Gly Thr Cys Ala Gly Cys Ala Gly Thr
    1385                1390                1395

Gly Thr Gly Gly Gly Gly Cys Cys Cys Ala Ala Ala Cys Thr
    1400                1405                1410

Gly Gly Cys Cys Thr Gly Cys Ala Gly Thr Cys Cys Cys Thr
    1415                1420                1425

Gly Gly Cys Ala Cys Cys Cys Thr Thr Cys Ala Gly Cys Cys Cys
    1430                1435                1440

Cys Cys Thr Gly Ala Gly Thr Thr Cys Cys Thr Cys Thr Ala Cys
    1445                1450                1455

Thr Cys Thr Cys Ala Thr Gly Gly Cys Gly Thr Gly Cys Ala Ala
    1460                1465                1470

Gly Gly Ala Cys Thr Cys Thr Ala Thr Cys Cys Cys Thr Cys
    1475                1480                1485

Ala Thr Cys Ala Gly Thr Ala Cys Cys Ala Cys Thr Cys Thr Gly
    1490                1495                1500

Thr Gly Cys Ala Cys Gly Gly Ala Gly Thr Thr Gly Gly Cys Ala
    1505                1510                1515

Thr Gly Gly Thr Gly Cys Ala Gly Ala Gly Thr Gly Gly Ala Gly
    1520                1525                1530

Cys Gly Ala Cys Ala Ala Thr Ala Gly
    1535                1540

<210> SEQ ID NO 16
<211> LENGTH: 518
<212> TYPE: PRT
<213> ORGANISM: Homo sapiens

<400> SEQUENCE: 16

Met Ala Asp Ala Asp Glu Gly Phe Gly Leu Ala His Thr Pro Leu Glu
1               5                   10                  15

Pro Asp Ala Lys Asp Leu Pro Cys Asp Ser Lys Pro Glu Ser Ala Leu
            20                  25                  30

Gly Ala Pro Ser Lys Ser Pro Ser Pro Gln Ala Ala Phe Thr Gln
        35                  40                  45

Gln Gly Met Glu Gly Ile Lys Val Phe Leu His Glu Arg Glu Leu Trp
    50                  55                  60

Leu Lys Phe His Glu Val Gly Thr Glu Met Ile Ile Thr Lys Ala Gly
65                  70                  75                  80

Arg Arg Met Phe Pro Ser Tyr Lys Val Lys Val Thr Gly Leu Asn Pro
                85                  90                  95

Lys Thr Lys Tyr Ile Leu Leu Met Asp Ile Val Pro Ala Asp Asp His
            100                 105                 110

Arg Tyr Lys Phe Ala Asp Asn Lys Trp Ser Val Thr Gly Lys Ala Glu
        115                 120                 125

Pro Ala Met Pro Gly Arg Leu Tyr Val His Pro Asp Ser Pro Ala Thr
```

```
            130                 135                 140
Gly Ala His Trp Met Arg Gln Leu Val Ser Phe Gln Lys Leu Lys Leu
145                 150                 155                 160

Thr Asn Asn His Leu Asp Pro Phe Gly His Ile Ile Leu Asn Ser Met
                165                 170                 175

His Lys Tyr Gln Pro Arg Leu His Ile Val Lys Ala Asp Glu Asn Asn
                180                 185                 190

Gly Phe Gly Ser Lys Asn Thr Ala Phe Cys Thr His Val Phe Pro Glu
                195                 200                 205

Thr Ala Phe Ile Ala Val Thr Ser Tyr Gln Asn His Lys Ile Thr Gln
210                 215                 220

Leu Lys Ile Glu Asn Asn Pro Phe Ala Lys Gly Phe Arg Gly Ser Asp
225                 230                 235                 240

Asp Met Glu Leu His Arg Met Ser Arg Met Gln Ser Lys Glu Tyr Pro
                245                 250                 255

Val Val Pro Arg Ser Thr Val Arg Gln Lys Val Ala Ser Asn His Ser
                260                 265                 270

Pro Phe Ser Ser Glu Ser Arg Ala Leu Ser Thr Ser Ser Asn Leu Gly
                275                 280                 285

Ser Gln Tyr Gln Cys Glu Asn Gly Val Ser Gly Pro Ser Gln Asp Leu
                290                 295                 300

Leu Pro Pro Pro Asn Pro Tyr Pro Leu Pro Gln Glu His Ser Gln Ile
305                 310                 315                 320

Tyr His Cys Thr Lys Arg Lys Glu Glu Glu Cys Ser Thr Thr Asp His
                325                 330                 335

Pro Tyr Lys Lys Pro Tyr Met Glu Thr Ser Pro Ser Glu Glu Asp Ser
                340                 345                 350

Phe Tyr Arg Ser Ser Tyr Pro Gln Gln Gln Gly Leu Gly Ala Ser Tyr
                355                 360                 365

Arg Thr Glu Ser Ala Gln Arg Gln Ala Cys Met Tyr Ala Ser Ser Ala
370                 375                 380

Pro Pro Ser Glu Pro Val Pro Ser Leu Glu Asp Ile Ser Cys Asn Thr
385                 390                 395                 400

Trp Pro Ser Met Pro Ser Tyr Ser Ser Cys Thr Val Thr Thr Val Gln
                405                 410                 415

Pro Met Asp Arg Leu Pro Tyr Gln His Phe Ser Ala His Phe Thr Ser
                420                 425                 430

Gly Pro Leu Val Pro Arg Leu Ala Gly Met Ala Asn His Gly Ser Pro
                435                 440                 445

Gln Leu Gly Glu Gly Met Phe Gln His Gln Thr Ser Val Ala His Gln
                450                 455                 460

Pro Val Val Arg Gln Cys Gly Pro Gln Thr Gly Leu Gln Ser Pro Gly
465                 470                 475                 480

Thr Leu Gln Pro Pro Glu Phe Leu Tyr Ser His Gly Val Pro Arg Thr
                485                 490                 495

Leu Ser Pro His Gln Tyr His Ser Val His Gly Val Gly Met Val Pro
                500                 505                 510

Glu Trp Ser Asp Asn Ser
                515

<210> SEQ ID NO 17
<211> LENGTH: 1557
<212> TYPE: PRT
<213> ORGANISM: Homo sapiens
```

<400> SEQUENCE: 17

```
Ala Thr Gly Gly Cys Cys Gly Ala Cys Gly Cys Ala Gly Ala Cys Gly
1               5                   10                  15

Ala Gly Gly Gly Cys Thr Thr Thr Gly Gly Cys Cys Thr Gly Gly Cys
            20                  25                  30

Gly Cys Ala Cys Ala Cys Gly Cys Cys Thr Cys Thr Gly Gly Ala Gly
        35                  40                  45

Cys Cys Thr Gly Ala Cys Gly Cys Ala Ala Ala Ala Gly Ala Cys Cys
    50                  55                  60

Thr Gly Cys Cys Cys Thr Gly Cys Gly Ala Thr Thr Cys Gly Ala Ala
65                  70                  75                  80

Ala Cys Cys Cys Gly Ala Gly Ala Gly Cys Gly Cys Gly Cys Thr Cys
                85                  90                  95

Gly Gly Gly Gly Cys Cys Cys Cys Cys Ala Gly Cys Ala Ala Gly Thr
            100                 105                 110

Cys Cys Cys Cys Gly Thr Cys Gly Thr Cys Cys Cys Cys Gly Cys Ala
        115                 120                 125

Gly Gly Cys Cys Gly Cys Cys Thr Thr Cys Ala Cys Cys Cys Ala Gly
    130                 135                 140

Cys Ala Gly Gly Gly Cys Ala Thr Gly Gly Ala Gly Gly Gly Ala Ala
145                 150                 155                 160

Thr Cys Ala Ala Ala Gly Thr Gly Thr Thr Thr Cys Thr Cys Cys Ala
                165                 170                 175

Thr Gly Ala Ala Ala Gly Ala Gly Ala Ala Cys Thr Gly Thr Gly Gly
            180                 185                 190

Cys Thr Ala Ala Ala Ala Thr Thr Cys Cys Ala Cys Gly Ala Ala Gly
        195                 200                 205

Thr Gly Gly Gly Cys Ala Cys Gly Gly Ala Ala Ala Thr Gly Ala Thr
    210                 215                 220

Cys Ala Thr Ala Ala Cys Cys Ala Ala Gly Gly Cys Thr Gly Gly Ala
225                 230                 235                 240

Ala Gly Gly Cys Gly Gly Ala Thr Gly Thr Thr Thr Cys Cys Cys Ala
                245                 250                 255

Gly Thr Thr Ala Cys Ala Ala Ala Gly Thr Gly Ala Ala Gly Gly Thr
            260                 265                 270

Gly Ala Cys Gly Gly Gly Cys Cys Thr Thr Ala Ala Thr Cys Cys Cys
        275                 280                 285

Ala Ala Ala Ala Cys Gly Ala Ala Gly Thr Ala Cys Ala Thr Thr Cys
    290                 295                 300

Thr Thr Cys Thr Cys Ala Thr Gly Gly Ala Cys Ala Thr Thr Gly Thr
305                 310                 315                 320

Ala Cys Cys Thr Gly Cys Cys Gly Ala Cys Gly Ala Thr Cys Ala Cys
                325                 330                 335

Ala Gly Ala Thr Ala Cys Ala Ala Ala Thr Thr Cys Gly Cys Ala Gly
            340                 345                 350

Ala Thr Ala Ala Thr Ala Ala Ala Thr Gly Gly Thr Cys Thr Gly Thr
        355                 360                 365

Gly Ala Cys Gly Gly Gly Cys Ala Ala Ala Gly Cys Thr Gly Ala Gly
    370                 375                 380

Cys Cys Cys Gly Cys Cys Ala Thr Gly Cys Cys Thr Gly Gly Cys Cys
385                 390                 395                 400

Gly Cys Cys Thr Gly Thr Ala Cys Gly Thr Gly Cys Ala Cys Cys Cys
```

```
                        405                 410                 415
Ala Gly Ala Cys Thr Cys Cys Cys Cys Gly Cys Ala Cys Cys
                420                 425                 430
Gly Gly Gly Gly Cys Gly Cys Ala Thr Thr Gly Gly Ala Thr Gly Ala
            435                 440                 445
Gly Gly Cys Ala Gly Cys Thr Cys Gly Thr Cys Thr Cys Cys Thr Thr
        450                 455                 460
Cys Cys Ala Gly Ala Ala Ala Cys Thr Cys Ala Ala Gly Cys Thr Cys
465                 470                 475                 480
Ala Cys Cys Ala Ala Cys Ala Ala Cys Ala Cys Thr Gly Gly
                485                 490                 495
Ala Cys Cys Cys Ala Thr Thr Gly Gly Gly Cys Ala Thr Ala Thr
                500                 505                 510
Thr Ala Thr Thr Cys Thr Ala Ala Ala Thr Thr Cys Cys Ala Thr Gly
        515                 520                 525
Cys Ala Cys Ala Ala Thr Ala Cys Ala Gly Cys Cys Thr Ala
        530                 535                 540
Gly Ala Thr Thr Ala Cys Ala Cys Ala Thr Cys Gly Thr Gly Ala Ala
545                 550                 555                 560
Ala Gly Cys Gly Gly Ala Thr Gly Ala Ala Ala Thr Ala Ala Thr
                565                 570                 575
Gly Gly Ala Thr Thr Gly Gly Cys Thr Cys Ala Ala Ala Ala
            580                 585                 590
Ala Thr Ala Cys Ala Gly Cys Gly Thr Thr Cys Thr Gly Cys Ala Cys
                595                 600                 605
Thr Cys Ala Cys Gly Thr Cys Thr Thr Thr Cys Cys Thr Gly Ala Gly
        610                 615                 620
Ala Cys Thr Gly Cys Gly Thr Thr Thr Ala Thr Ala Gly Cys Ala Gly
625                 630                 635                 640
Thr Gly Ala Cys Thr Thr Cys Cys Thr Ala Cys Cys Ala Gly Ala Ala
                645                 650                 655
Cys Cys Ala Cys Ala Ala Gly Ala Thr Cys Ala Cys Gly Cys Ala Ala
                660                 665                 670
Thr Thr Ala Ala Ala Gly Ala Thr Thr Gly Ala Gly Ala Ala Thr Ala
            675                 680                 685
Ala Thr Cys Cys Cys Thr Thr Thr Gly Cys Cys Ala Ala Ala Gly Gly
        690                 695                 700
Ala Thr Thr Thr Cys Gly Gly Gly Cys Ala Gly Thr Gly Ala Thr
705                 710                 715                 720
Gly Ala Cys Ala Thr Gly Gly Ala Gly Cys Thr Gly Cys Ala Cys Ala
                725                 730                 735
Gly Ala Ala Thr Gly Thr Cys Ala Ala Gly Ala Ala Thr Gly Cys Ala
            740                 745                 750
Ala Ala Gly Thr Ala Ala Ala Gly Ala Ala Thr Ala Thr Cys Cys Cys
        755                 760                 765
Gly Thr Gly Gly Thr Cys Cys Cys Ala Gly Gly Ala Gly Cys Ala
        770                 775                 780
Cys Cys Gly Thr Gly Ala Gly Gly Cys Ala Ala Ala Ala Gly Thr
785                 790                 795                 800
Gly Gly Cys Cys Thr Cys Cys Ala Ala Cys Ala Cys Ala Gly Thr
            805                 810                 815
Cys Cys Thr Thr Thr Cys Ala Gly Cys Ala Gly Cys Gly Ala Gly Thr
        820                 825                 830
```

```
Cys Thr Cys Gly Ala Gly Cys Thr Cys Thr Cys Thr Cys Cys Ala Cys
        835                 840                 845

Cys Thr Cys Ala Thr Cys Cys Ala Ala Thr Thr Thr Gly Gly Gly Gly
    850                 855                 860

Thr Cys Cys Cys Ala Ala Thr Ala Cys Cys Ala Gly Thr Gly Thr Gly
865                 870                 875                 880

Ala Gly Ala Ala Thr Gly Gly Thr Gly Thr Thr Thr Cys Cys Gly Gly
                885                 890                 895

Cys Cys Cys Cys Thr Cys Cys Cys Ala Gly Gly Ala Cys Cys Thr Cys
            900                 905                 910

Cys Thr Gly Cys Cys Thr Cys Cys Ala Cys Cys Cys Ala Ala Cys Cys
        915                 920                 925

Cys Ala Thr Ala Cys Cys Cys Ala Cys Thr Gly Cys Cys Cys Cys Ala
    930                 935                 940

Gly Gly Ala Gly Cys Ala Thr Ala Gly Cys Cys Ala Ala Ala Thr Thr
945                 950                 955                 960

Thr Ala Cys Cys Ala Thr Thr Gly Thr Ala Cys Cys Ala Ala Gly Ala
                965                 970                 975

Gly Gly Ala Ala Ala Gly Ala Gly Gly Ala Ala Gly Ala Ala Thr Gly
            980                 985                 990

Thr Thr Cys Cys Ala Cys Cys Ala  Cys Ala Gly Ala Cys  Cys Ala Thr
        995                 1000                1005

Cys Cys  Cys Thr Ala Thr Ala  Ala Gly Ala Ala Gly  Cys Cys Cys
    1010                1015                1020

Thr Ala  Cys Ala Thr Gly Gly  Ala Gly Ala Cys Ala  Thr Cys Ala
    1025                1030                1035

Cys Cys  Cys Ala Gly Thr Gly  Ala Ala Gly Ala Ala  Gly Ala Thr
    1040                1045                1050

Thr Cys  Cys Thr Thr Cys Thr  Ala Cys Cys Gly Cys  Thr Cys Thr
    1055                1060                1065

Ala Gly  Cys Thr Ala Thr Cys  Cys Ala Cys Ala Gly  Cys Ala Gly
    1070                1075                1080

Cys Ala  Gly Gly Gly Cys Cys  Thr Gly Gly Gly Thr  Gly Cys Cys
    1085                1090                1095

Thr Cys  Cys Thr Ala Cys Ala  Gly Gly Ala Cys Ala  Gly Ala Gly
    1100                1105                1110

Thr Cys  Gly Gly Cys Ala Cys  Ala Gly Cys Gly Gly  Cys Ala Ala
    1115                1120                1125

Gly Cys  Thr Thr Gly Cys Ala  Thr Gly Thr Ala Thr  Gly Cys Cys
    1130                1135                1140

Ala Gly  Cys Thr Cys Thr Gly  Cys Gly Cys Cys Cys  Cys Cys Cys
    1145                1150                1155

Ala Gly  Cys Gly Ala Gly Cys  Cys Thr Gly Thr Gly  Cys Cys Cys
    1160                1165                1170

Ala Gly  Cys Cys Thr Ala Gly  Ala Gly Gly Ala Cys  Ala Thr Cys
    1175                1180                1185

Ala Gly  Cys Thr Gly Cys Ala  Ala Cys Ala Cys Gly  Thr Gly Gly
    1190                1195                1200

Cys Cys  Ala Ala Gly Cys Ala  Thr Gly Cys Cys Thr  Thr Cys Cys
    1205                1210                1215

Thr Ala  Cys Ala Gly Cys Ala  Gly Cys Thr Gly Cys  Ala Cys Cys
    1220                1225                1230
```

```
Gly Thr Cys Ala Cys Cys Ala Cys Cys Gly Thr Gly Cys Ala Gly
    1235                1240                1245

Cys Cys Cys Ala Thr Gly Gly Ala Cys Ala Gly Gly Cys Thr Ala
    1250                1255                1260

Cys Cys Cys Thr Ala Cys Cys Ala Gly Cys Ala Cys Thr Thr Cys
    1265                1270                1275

Thr Cys Cys Gly Cys Thr Cys Ala Cys Thr Thr Cys Ala Cys Cys
    1280                1285                1290

Thr Cys Gly Gly Gly Cys Cys Cys Cys Thr Gly Gly Thr Cys
    1295                1300                1305

Cys Cys Thr Cys Gly Gly Cys Thr Gly Gly Cys Thr Gly Gly Cys
    1310                1315                1320

Ala Thr Gly Gly Cys Cys Ala Ala Cys Cys Ala Thr Gly Gly Cys
    1325                1330                1335

Thr Cys Cys Cys Ala Cys Ala Gly Cys Thr Gly Gly Gly Ala
    1340                1345                1350

Gly Ala Gly Gly Gly Ala Ala Thr Gly Thr Thr Cys Cys Ala Gly
    1355                1360                1365

Cys Ala Cys Cys Ala Gly Ala Cys Cys Thr Cys Cys Gly Thr Gly
    1370                1375                1380

Gly Cys Cys Cys Ala Cys Cys Ala Gly Cys Cys Thr Gly Thr Gly
    1385                1390                1395

Gly Thr Cys Ala Gly Gly Cys Ala Gly Thr Gly Thr Gly Gly Gly
    1400                1405                1410

Cys Cys Thr Cys Ala Gly Ala Cys Thr Gly Gly Cys Cys Thr Gly
    1415                1420                1425

Cys Ala Gly Thr Cys Cys Cys Thr Gly Gly Cys Ala Cys Cys
    1430                1435                1440

Cys Thr Thr Cys Ala Gly Cys Cys Cys Cys Thr Gly Ala Gly
    1445                1450                1455

Thr Thr Cys Cys Thr Cys Thr Ala Cys Thr Cys Thr Cys Ala Thr
    1460                1465                1470

Gly Gly Cys Gly Thr Gly Cys Cys Ala Ala Gly Gly Ala Cys Thr
    1475                1480                1485

Cys Thr Ala Thr Cys Cys Cys Thr Cys Ala Thr Cys Ala Gly
    1490                1495                1500

Thr Ala Cys Cys Ala Cys Thr Cys Thr Gly Thr Gly Cys Ala Cys
    1505                1510                1515

Gly Gly Ala Gly Thr Thr Gly Gly Cys Ala Thr Gly Gly Thr Gly
    1520                1525                1530

Cys Cys Ala Gly Ala Gly Thr Gly Gly Ala Gly Cys Gly Ala Cys
    1535                1540                1545

Ala Ala Thr Ala Gly Cys Thr Ala Ala
    1550                1555
```

<210> SEQ ID NO 18
<211> LENGTH: 268
<212> TYPE: PRT
<213> ORGANISM: Homo sapiens

<400> SEQUENCE: 18

```
Met Ala Gln Pro Leu Cys Pro Pro Leu Ser Glu Ser Trp Met Leu Ser
1               5                   10                  15

Ala Ala Trp Gly Pro Thr Arg Arg Pro Pro Ser Asp Lys Asp Cys
                20                  25                  30
```

Gly Arg Ser Leu Val Ser Ser Pro Asp Ser Trp Gly Ser Thr Pro Ala
            35                  40                  45

Asp Ser Pro Val Ala Ser Pro Ala Arg Pro Gly Thr Leu Arg Asp Pro
 50                  55                  60

Arg Ala Pro Ser Val Gly Arg Gly Ala Arg Ser Ser Arg Leu Gly
 65                  70                  75                  80

Ser Gly Gln Arg Gln Ser Ala Ser Glu Arg Glu Lys Leu Arg Met Arg
                85                  90                  95

Thr Leu Ala Arg Ala Leu His Glu Leu Arg Arg Phe Leu Pro Pro Ser
                100                 105                 110

Val Ala Pro Ala Gly Gln Ser Leu Thr Lys Ile Glu Thr Leu Arg Leu
                115                 120                 125

Ala Ile Arg Tyr Ile Gly His Leu Ser Ala Val Leu Gly Leu Ser Glu
            130                 135                 140

Glu Ser Leu Gln Arg Arg Cys Arg Gln Arg Gly Asp Ala Gly Ser Pro
145                 150                 155                 160

Arg Gly Cys Pro Leu Cys Pro Asp Asp Cys Pro Ala Gln Met Gln Thr
                165                 170                 175

Arg Thr Gln Ala Glu Gly Gln Gly Gln Gly Arg Gly Leu Gly Leu Val
                180                 185                 190

Ser Ala Val Arg Ala Gly Ala Ser Trp Gly Ser Pro Pro Ala Cys Pro
            195                 200                 205

Gly Ala Arg Ala Ala Pro Glu Pro Arg Asp Pro Pro Ala Leu Phe Ala
            210                 215                 220

Glu Ala Ala Cys Pro Glu Gly Gln Ala Met Glu Pro Ser Pro Pro Ser
225                 230                 235                 240

Pro Leu Leu Pro Gly Asp Val Leu Ala Leu Leu Glu Thr Trp Met Pro
                245                 250                 255

Leu Ser Pro Leu Glu Trp Leu Pro Glu Glu Pro Lys
            260                 265

<210> SEQ ID NO 19
<211> LENGTH: 807
<212> TYPE: PRT
<213> ORGANISM: Homo sapiens

<400> SEQUENCE: 19

Ala Thr Gly Gly Cys Cys Cys Ala Gly Cys Cys Cys Thr Gly Thr
1               5                   10                  15

Gly Cys Cys Cys Gly Cys Cys Gly Cys Thr Cys Thr Cys Cys Gly Ala
                20                  25                  30

Gly Thr Cys Cys Thr Gly Gly Ala Thr Gly Cys Thr Cys Thr Cys Thr
            35                  40                  45

Gly Cys Gly Gly Cys Cys Thr Gly Gly Gly Cys Cys Cys Ala Ala
            50                  55                  60

Cys Thr Cys Gly Gly Cys Gly Cys Cys Gly Cys Gly Cys Gly Cys Cys
65                  70                  75                  80

Cys Thr Cys Cys Gly Ala Cys Ala Ala Gly Gly Ala Cys Thr Gly Cys
                85                  90                  95

Gly Gly Cys Cys Gly Cys Thr Cys Cys Cys Thr Cys Gly Thr Cys Thr
                100                 105                 110

Cys Gly Thr Cys Cys Cys Ala Gly Ala Cys Thr Cys Ala Thr Gly
            115                 120                 125

Gly Gly Gly Cys Ala Gly Cys Ala Cys Cys Cys Cys Ala Gly Cys Cys

-continued

```
            130                 135                 140
Gly Ala Cys Ala Gly Cys Cys Cys Gly Thr Gly Cys Gly Ala
145                 150                 155                 160
Gly Cys Cys Cys Gly Cys Gly Cys Gly Cys Cys Ala Gly Gly
                165                 170                 175
Cys Ala Cys Cys Cys Thr Cys Cys Gly Gly Ala Cys Cys Cys
                180                 185                 190
Cys Gly Cys Gly Cys Cys Cys Cys Thr Cys Cys Gly Thr Ala Gly
                195                 200                 205
Gly Thr Ala Gly Gly Cys Gly Cys Gly Cys Gly Cys Gly Cys Gly
        210                 215                 220
Cys Ala Gly Cys Ala Gly Cys Cys Gly Cys Thr Gly Gly Gly Cys
225                 230                 235                 240
Ala Gly Cys Gly Gly Gly Cys Ala Gly Ala Gly Gly Cys Ala Gly Ala
                245                 250                 255
Gly Cys Gly Cys Cys Ala Gly Thr Gly Ala Gly Cys Gly Gly Gly Ala
                260                 265                 270
Gly Ala Ala Ala Cys Thr Gly Cys Gly Cys Ala Thr Gly Cys Gly Cys
            275                 280                 285
Ala Cys Gly Cys Thr Gly Gly Cys Cys Cys Gly Cys Cys Cys
290                 295                 300
Thr Gly Cys Ala Cys Gly Ala Gly Cys Thr Gly Cys Gly Cys Cys Gly
305                 310                 315                 320
Cys Thr Thr Thr Cys Thr Ala Cys Cys Gly Cys Cys Gly Thr Cys
                325                 330                 335
Gly Thr Gly Gly Cys Gly Cys Cys Cys Gly Cys Gly Gly Gly Cys Cys
                340                 345                 350
Ala Gly Ala Gly Cys Cys Thr Gly Ala Cys Cys Ala Ala Gly Ala Thr
            355                 360                 365
Cys Gly Ala Gly Ala Cys Gly Cys Thr Gly Cys Gly Cys Cys Thr Gly
            370                 375                 380
Gly Cys Thr Ala Thr Cys Cys Gly Cys Thr Ala Thr Ala Thr Cys Gly
385                 390                 395                 400
Gly Cys Cys Ala Cys Cys Thr Gly Thr Cys Gly Gly Cys Cys Gly Thr
                405                 410                 415
Gly Cys Thr Ala Gly Gly Cys Cys Thr Cys Ala Gly Cys Gly Ala Gly
                420                 425                 430
Gly Ala Gly Ala Gly Thr Cys Thr Cys Cys Ala Gly Cys Gly Cys Cys
            435                 440                 445
Gly Gly Thr Gly Cys Cys Gly Gly Cys Ala Gly Cys Gly Cys Gly Gly
            450                 455                 460
Thr Gly Ala Cys Gly Cys Gly Gly Gly Gly Thr Cys Cys Cys Cys Thr
465                 470                 475                 480
Cys Gly Gly Gly Gly Cys Thr Gly Cys Cys Cys Gly Cys Thr Gly Thr
                485                 490                 495
Gly Cys Cys Cys Cys Gly Ala Cys Gly Ala Cys Thr Gly Cys Cys Cys
                500                 505                 510
Cys Gly Cys Gly Cys Ala Gly Ala Thr Gly Cys Ala Gly Ala Cys Ala
            515                 520                 525
Cys Gly Gly Ala Cys Gly Cys Ala Gly Cys Thr Gly Ala Gly Gly
            530                 535                 540
Gly Gly Cys Ala Gly Gly Gly Gly Cys Ala Gly Gly Gly Cys Gly
545                 550                 555                 560
```

```
Cys Gly Gly Gly Cys Thr Gly Gly Cys Cys Thr Gly Thr Ala
            565                 570                 575

Thr Cys Cys Gly Cys Cys Gly Thr Cys Cys Gly Cys Gly Cys Gly
        580                 585                 590

Gly Gly Gly Cys Gly Thr Cys Cys Thr Gly Gly Gly Ala Thr Cys
        595                 600                 605

Cys Cys Cys Gly Cys Cys Thr Gly Cys Thr Gly Cys Cys Cys
    610                 615                 620

Gly Gly Ala Gly Cys Cys Cys Gly Ala Gly Cys Thr Gly Cys Ala Cys
625                 630                 635                 640

Cys Cys Gly Ala Gly Cys Cys Gly Cys Gly Cys Gly Ala Cys Cys Cys
                645                 650                 655

Gly Cys Cys Thr Gly Cys Gly Cys Thr Gly Thr Thr Cys Gly Cys Cys
                660                 665                 670

Gly Ala Gly Gly Cys Gly Gly Cys Gly Thr Gly Cys Cys Thr Gly
                675                 680                 685

Ala Ala Gly Gly Gly Cys Ala Gly Gly Cys Gly Ala Thr Gly Gly Ala
690                 695                 700

Gly Cys Cys Ala Ala Gly Cys Cys Cys Ala Cys Cys Gly Thr Cys Cys
705                 710                 715                 720

Cys Cys Gly Cys Thr Cys Cys Thr Thr Cys Cys Gly Gly Cys Gly
                725                 730                 735

Ala Cys Gly Thr Gly Cys Thr Gly Gly Cys Thr Cys Thr Gly Thr Thr
                740                 745                 750

Gly Gly Ala Gly Ala Cys Cys Thr Gly Gly Ala Thr Gly Cys Cys
                755                 760                 765

Cys Thr Cys Thr Cys Gly Cys Cys Thr Cys Thr Gly Gly Ala Gly Thr
770                 775                 780

Gly Gly Cys Thr Gly Cys Cys Thr Gly Ala Gly Gly Ala Gly Cys Cys
785                 790                 795                 800

Cys Ala Ala Gly Thr Gly Ala
                805

<210> SEQ ID NO 20
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 20
ctatataaat ag                                                        12

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Tyr Gly Arg Lys Lys Arg Arg Gln Arg Arg Arg
1               5                   10

<210> SEQ ID NO 22
<211> LENGTH: 12
<212> TYPE: PRT
<213> ORGANISM: Artificial sequence
```

```
<220> FEATURE:
<223> OTHER INFORMATION: Synthetic peptide

<400> SEQUENCE: 22

Arg Arg Gln Arg Arg Thr Ser Lys Leu Met Lys Arg
1               5                   10

<210> SEQ ID NO 23
<211> LENGTH: 27
<212> TYPE: PRT
<213> ORGANISM: Artificial sequence
<220> FEATURE:
<223> OTHER INFORMATION: Synthetic peptide

<400> SEQUENCE: 23

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 24
<211> LENGTH: 33
<212> TYPE: PRT
<213> ORGANISM: Artificial sequence
<220> FEATURE:
<223> OTHER INFORMATION: Synthetic peptide

<400> SEQUENCE: 24

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 25
<211> LENGTH: 16
<212> TYPE: PRT
<213> ORGANISM: Artificial sequence
<220> FEATURE:
<223> OTHER INFORMATION: Synthetic peptide

<400> SEQUENCE: 25

Arg Gln Ile Lys Ile Trp Phe Gln Asn Arg Arg Met Lys Trp Lys Lys
1               5                   10                  15

<210> SEQ ID NO 26
<211> LENGTH: 9
<212> TYPE: PRT
<213> ORGANISM: Artificial sequence
<220> FEATURE:
<223> OTHER INFORMATION: Synthetic peptide

<400> SEQUENCE: 26

Arg Lys Lys Arg Arg Gln Arg Arg Arg
1               5

<210> SEQ ID NO 27
<211> LENGTH: 11
<212> TYPE: PRT
<213> ORGANISM: Artificial sequence
<220> FEATURE:
<223> OTHER INFORMATION: Synthetic peptide

<400> SEQUENCE: 27

Tyr Ala Arg Ala Ala Ala Arg Gln Ala Arg Ala
```

```
<210> SEQ ID NO 28
<211> LENGTH: 11
<212> TYPE: PRT
<213> ORGANISM: Artificial sequence
<220> FEATURE:
<223> OTHER INFORMATION: Synthetic peptide

<400> SEQUENCE: 28

Thr His Arg Leu Pro Arg Arg Arg Arg Arg Arg
1               5                   10

<210> SEQ ID NO 29
<211> LENGTH: 11
<212> TYPE: PRT
<213> ORGANISM: Artificial sequence
<220> FEATURE:
<223> OTHER INFORMATION: Synthetic peptide

<400> SEQUENCE: 29

Gly Gly Arg Arg Ala Arg Arg Arg Arg Arg Arg
1               5                   10

<210> SEQ ID NO 30
<211> LENGTH: 44
<212> TYPE: PRT
<213> ORGANISM: Homo sapiens

<400> SEQUENCE: 30

Met Ser Asp Lys Pro Asp Met Ala Glu Ile Glu Lys Phe Asp Lys Ser
1               5                   10                  15

Lys Leu Lys Lys Thr Glu Thr Gln Glu Lys Asn Pro Leu Pro Ser Lys
            20                  25                  30

Glu Thr Ile Glu Gln Glu Lys Gln Ala Gly Glu Ser
        35                  40

<210> SEQ ID NO 31
<211> LENGTH: 27
<212> TYPE: DNA
<213> ORGANISM: Artificial Sequence
<220> FEATURE:
<223> OTHER INFORMATION: synthetic primer

<400> SEQUENCE: 31
gggaggaatg tgtttaagga ttaaaaa                                           27

<210> SEQ ID NO 32
<211> LENGTH: 25
<212> TYPE: DNA
<213> ORGANISM: Artificial sequence
<220> FEATURE:
<223> OTHER INFORMATION: Synthetic primer

<400> SEQUENCE: 32
attggttgtt tgtggttttg gtggt                                             25

<210> SEQ ID NO 33
<211> LENGTH: 26
<212> TYPE: DNA
<213> ORGANISM: Artificial sequence
<220> FEATURE:
<223> OTHER INFORMATION: Synthetic primer

<400> SEQUENCE: 33
```

```
taaaaacatt tccccaaac tccccc                                    26

<210> SEQ ID NO 34
<211> LENGTH: 27
<212> TYPE: DNA
<213> ORGANISM: Artificial sequence
<220> FEATURE:
<223> OTHER INFORMATION: Synthetic primer

<400> SEQUENCE: 34
aattagggga gttgggtatt agttaag                                  27

<210> SEQ ID NO 35
<211> LENGTH: 30
<212> TYPE: DNA
<213> ORGANISM: Artificial sequence
<220> FEATURE:
<223> OTHER INFORMATION: Synthetic primer

<400> SEQUENCE: 35
cccacttcaa aaatataaaa aaaataaaaa                               30

<210> SEQ ID NO 36
<211> LENGTH: 25
<212> TYPE: DNA
<213> ORGANISM: Artificial Sequence
<220> FEATURE:
<223> OTHER INFORMATION: synthetic primer

<400> SEQUENCE: 36
tacaaaacat cccaccccaa acctc                                    25
```

METHODS FOR GENERATING CARDIOMYOCYTES

CROSS-REFERENCE

This application claims the benefit of U.S. Provisional Patent Application No. 61/529,042, filed Aug. 30, 2011, which application is incorporated herein by reference in its entirety.

STATEMENT REGARDING FEDERALLY SPONSORED RESEARCH

This invention was made with government support under Grant No. U01 HL100406 awarded by the National Institutes of Health. The government has certain rights in the invention.

BACKGROUND

Heart disease is a leading cause of adult and childhood mortality in developed countries. The underlying pathology is typically loss of cardiomyocytes that leads to heart failure, or improper development of cardiomyocytes during embryogenesis that leads to congenital heart malformations. A major objective is to replace the lost cardiomyocytes and to rescue cardiac dysfunction.

There is a need in the art for methods of generating cardiomyocytes.

LITERATURE

U.S. Patent Publication No. 2009/0208465; U.S. Pat. No. 7,682,828; U.S. Patent Publication No. 2010/0075421; WO 2009/152484; WO 2009/152485; Takahashi and Yamanaka (2006) *Cell* 126:663; Ieda et al. (2010) *Cell* 142:375.

SUMMARY

The present disclosure provides method of generating cardiomyocytes from post-natal fibroblasts. The present disclosure further provides cells and compositions for use in generating cardiomyocytes.

BRIEF DESCRIPTION OF THE DRAWINGS

FIG. 9 depicts an amino acid sequence of a human Esrrg.

FIGS. 10A and 10B depict a nucleotide sequence encoding the amino acid sequence depicted in FIG. 9.

FIGS. 11A and 11B depict an alignment of amino acid sequences of human Esrrg isoforms.

FIGS. 12-23 depict amino acid sequences of various reprogramming factors and nucleotide sequences encoding same.

DEFINITIONS

Figure 1:
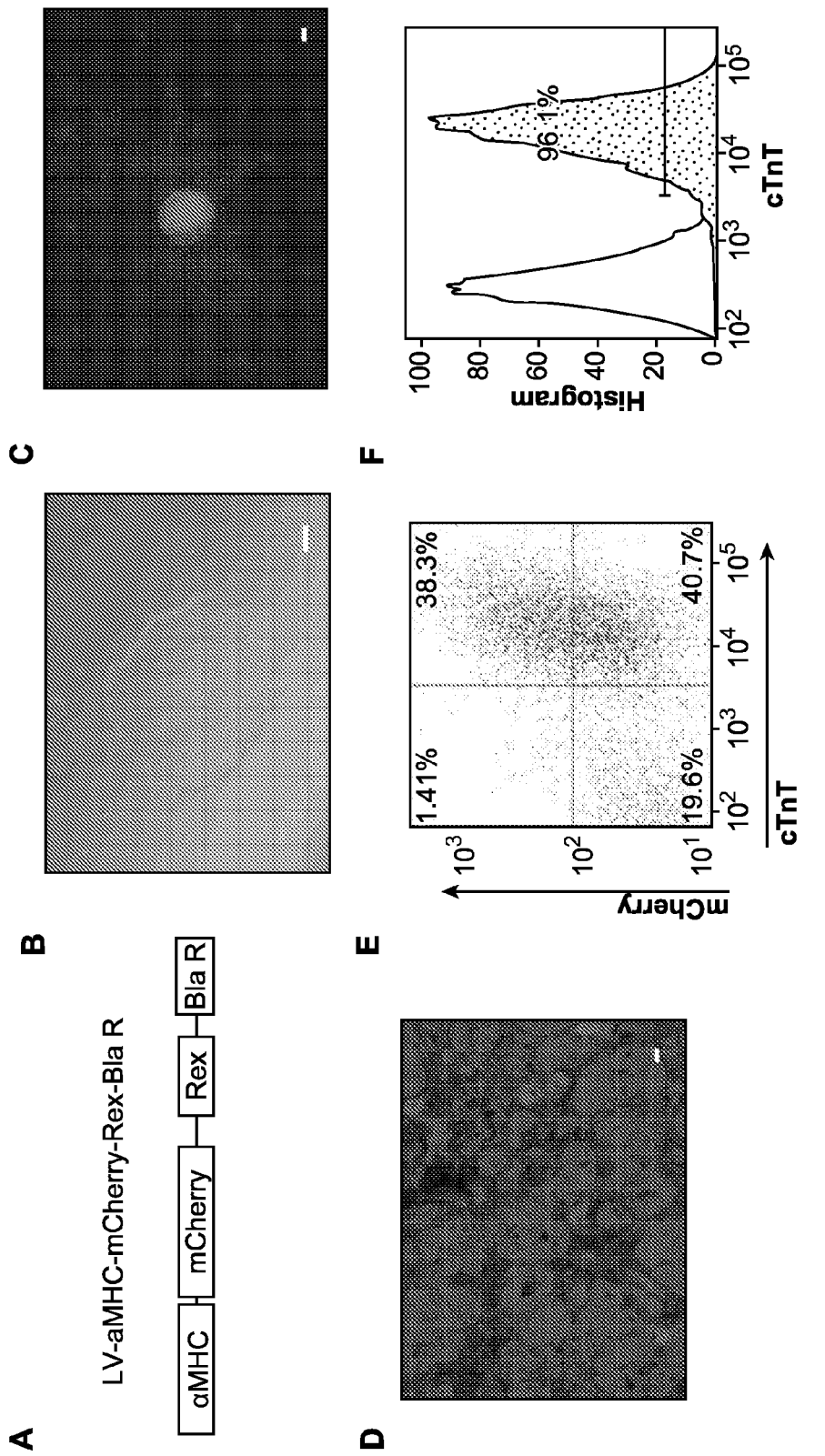
FIGS. 1A-J depict results using fibroblasts differentiated from transgenic H9 human embryonic stem cells in which the red fluorescent protein mCherry is driven by mouse α-myosin heavy chain promoter.

The terms "polypeptide," "peptide," and "protein," used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "nucleic acid" and "polynucleotide" are used interchangeably herein and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The term "operably linked" refers to functional linkage between molecules to provide a desired function. For example, "operably linked" in the context of nucleic acids refers to a functional linkage between nucleic acids to provide a desired function such as transcription, translation, and the like, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide.

As used herein the term "isolated" with reference to a cell, refers to a cell that is in an environment different from that in which the cell naturally occurs, e.g., where the cell naturally occurs in a multicellular organism, and the cell is removed from the multicellular organism, the cell is "isolated." An isolated genetically modified host cell can be present in a mixed population of genetically modified host cells, or in a mixed population comprising genetically modified host cells and host cells that are not genetically modified. For example, an isolated genetically modified host cell can be present in a mixed population of genetically modified host cells in vitro, or in a mixed in vitro population comprising genetically modified host cells and host cells that are not genetically modified.

A "host cell," as used herein, denotes an in vivo or in vitro cell (e.g., a eukaryotic cell cultured as a unicellular entity), which eukaryotic cell can be, or has been, used as recipients for a nucleic acid (e.g., an exogenous nucleic acid) or an exogenous polypeptide(s), and include the progeny of the original cell which has been modified by introduction of the exogenous polypeptide(s) or genetically modified by the nucleic acid. It is understood that the progeny of a single cell may not necessarily be completely identical in morphology or in genomic or total DNA complement as the original parent, due to natural, accidental, or deliberate mutation.

The term "genetic modification" and refers to a permanent or transient genetic change induced in a cell following introduction of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

As used herein, the term "exogenous nucleic acid" refers to a nucleic acid that is not normally or naturally found in and/or produced by a cell in nature, and/or that is introduced into the cell (e.g., by electroporation, transfection, infection, lipofection, or any other means of introducing a nucleic acid into a cell).

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. In some embodiments, the individual is a human. In some embodiments, the individual is a murine.

A "therapeutically effective amount" or "efficacious amount" means the amount of a compound or a number of cells that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cardiomyocyte" includes a plurality of such cardiomyocyte and reference to "the reprogramming factor" includes reference to one or more reprogramming factors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides method of generating cardiomyocytes from post-natal fibroblasts. The present disclosure further provides cells and compositions for use in generating cardiomyocytes.

Methods of Generating Cardiomyocytes

The present disclosure provides method of generating cardiomyocytes from post-natal fibroblasts. The methods generally involve introducing into a post-natal fibroblast one or more reprogramming factors. In some cases, the polypeptides themselves are introduced into a post-natal fibroblast. In other cases, the post-natal fibroblast is genetically modified with one or more nucleic acids comprising nucleotide sequences encoding the re-programming factors. The post-natal fibroblast in some cases is a human cardiac fibroblast. The modification can be carried out in vivo or in vitro.

In some embodiments, the methods involve introducing into a post-natal fibroblast the following reprogramming factors: Gata4, Mef2c, Tbx5, Mesp1, Esrrg, Nkx2.5, Srf, Zfpm2, Myocd, Baf60c, Hand2, Isl1, Nfatc1, Smyd1, and TGFβ1. In some cases, the polypeptides themselves are introduced into a post-natal fibroblast. In other cases, the post-natal fibroblast is genetically modified with one or more nucleic acids comprising nucleotide sequences encoding Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides.

In some embodiments, the methods involve introducing into a post-natal fibroblast the following reprogramming factors: Gata4, Mef2c, Tbx5, Mesp1, Esrrg, Nkx2.5, Srf, Zfpm2, and Myocd. In some cases, the polypeptides themselves are introduced into a post-natal fibroblast. In other cases, the post-natal fibroblast is genetically modified with one or more nucleic acids comprising nucleotide sequences encoding Gata4, Mef2c, Tbx5, Mesp1, Esrrg, Nkx2.5, Srf, Zfpm2, and Myocd polypeptides.

In some embodiments, the methods involve introducing into a post-natal fibroblast the following reprogramming factors: Gata4, Mef2c, Tbx5, Mesp1, and Esrrg; and one or more of Nkx2.5, Srf, Zfpm2, Myocd, Baf60c, Hand2, Isl1, Nfatc1, Smyd1, and TGFβ1. In some cases, the polypeptides themselves are introduced into a post-natal fibroblast. In other cases, the post-natal fibroblast is genetically modified with one or more nucleic acids comprising nucleotide sequences encoding Gata4, Mef2c, Tbx5, Mesp1, and Esrrg; and one or more of Nkx2.5, Srf, Zfpm2, Myocd, Baf60c, Hand2, Isl1, Nfatc1, Smyd1, and TGFβ1 polypeptides.

In some embodiments, the methods involve introducing into a post-natal fibroblast the following reprogramming factors: Gata4, Mef2c, Tbx5, Mesp1, and Esrrg. In some cases, the polypeptides themselves are introduced into a post-natal fibroblast. In other cases, the post-natal fibroblast is genetically modified with one or more nucleic acids comprising nucleotide sequences encoding Gata4, Mef2c, Tbx5, Mesp1, and Esrrg polypeptides.

In some embodiments, the methods involve introducing into a post-natal fibroblast five (and only five) reprogramming factors: Gata4, Mef2c, Tbx5, Mesp1, and Esrrg polypeptides. In some cases, the polypeptides themselves are introduced into a post-natal fibroblast. In other cases, the post-natal fibroblast is genetically modified with one or more nucleic acids comprising nucleotide sequences encoding Gata4, Mef2c, Tbx5, Mesp1, and Esrrg polypeptides (and no other exogenous polypeptides).

Cardiomyocytes generated from post-natal fibroblasts using a subject method are referred to herein as "induced cardiomyocytes." Polypeptides such as Gata4, Mef2c, Tbx5, Mesp1, Esrrg, Nkx2.5, Srf, Zfpm2, Myocd, Baf60c, Hand2, Isl1, Nfatc1, Smyd1, and TGFβ1) are also referred to collectively herein as "reprogramming factors." In any of the embodiments described below, "reprogramming factors" that are introduced (either as the polypeptides themselves or as nucleic acid(s) comprising nucleotide sequences encoding the polypeptides) into a post-natal fibroblast can include:

1) Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides;
2) Gata4, Mef2c, Tbx5, Mesp1, Esrrg, Nkx2.5, Srf, Zfpm2, and Myocd polypeptides;
3) Gata4, Mef2c, Tbx5, Mesp1, and Esrrg polypeptides; and
4) Gata4, Mef2c, Tbx5, Mesp1, and Esrrg polypeptides; and one or more of, Nkx2.5, Srf, Zfpm2, Myocd, Baf60c, Hand2, Isl1, Nfatc1, Smyd1, and TGFβ1 polypeptides.

Reprogramming factors that include Gata4, Mef2c, Tbx5, Mesp1, and Esrrg polypeptides; and one or more of, Nkx2.5, Srf, Zfpm2, Myocd, Baf60c, Hand2, Isl1, Nfatc1, Smyd1, and TGFβ1 polypeptides can include, e.g.:

1) Gata4, Mef2c, Tbx5, Mesp1, Esrrg, Nkx2.5, Srf, Zfpm2, Myocd, and BAF60c polypeptides;
2) Gata4, Mef2c, Tbx5, Mesp1, Esrrg, Nkx2.5, Srf, Zfpm2, Myocd, BAF60c, and Hand2 polypeptides;
3) Gata4, Mef2c, Tbx5, Mesp1, Esrrg, Nkx2.5, Srf, Zfpm2, Myocd, BAF60c, Hand2, and Isl1 polypeptides;
4) Gata4, Mef2c, Tbx5, Mesp1, Esrrg, Nkx2.5, Srf, Zfpm2, Myocd, BAF60c, Hand2, Isl1, and Nfatc1 polypeptides;
5) Gata4, Mef2c, Tbx5, Mesp1, Esrrg, Nkx2.5, Srf, Zfpm2, Myocd, BAF60c, Hand2, Isl1, Nfatc1, and Smyd1 polypeptides;
6) Gata4, Mef2c, Tbx5, Mesp1, Esrrg, Nkx2.5, Srf, Zfpm2, Myocd, BAF60c, Hand2, Isl1, Nfatc1, and TGFβ1 polypeptides;
7) Gata4, Mef2c, Tbx5, Mesp1, Esrrg, and Nkx2.5 polypeptides;
8) Gata4, Mef2c, Tbx5, Mesp1, Esrrg, Nkx2.5, and Srf polypeptides;
9) Gata4, Mef2c, Tbx5, Mesp1, Esrrg, Nkx2.5, Srf, and Zfpm2 polypeptides; and
10) Gata4, Mef2c, Tbx5, Mesp1, Esrrg, Nkx2.5, Srf, and Myocd polypeptides.

Those skilled in the art will recognize that other combinations are possible.

As noted above, in some cases, a subject method of generating a cardiomyocyte involves genetically modifying a post-natal fibroblast with one or more nucleic acids comprising nucleotide sequences encoding reprogramming factors (e.g., Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides). The reprogramming factors encoded by the nucleotide sequences are produced in the post-natal fibroblast and, as a result of the production of the one or more reprogramming factors, the genetically modified fibroblast is reprogrammed into a differentiated cardiomyocyte.

As noted above, in some cases, a subject method of generating a cardiomyocyte involves genetically modifying a post-natal fibroblast with one or more nucleic acids comprising nucleotide sequences encoding reprogramming factors (e.g., Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides). The reprogramming factors are produced in the post-natal fibroblast and, as a result of the production of the reprogramming factors, the genetically modified fibroblast is reprogrammed to become a differentiated cardiomyocyte.

In some cases, a post-natal fibroblast is modified by introducing reprogramming factor polypeptides themselves into a host post-natal fibroblast (e.g., where suitable reprogramming factors include Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides). A post-natal fibroblast into which reprogramming factor polypeptides has been introduced (either by introducing the polypeptides themselves or by introducing one or more nucleic acids comprising nucleotide sequence encoding the one or more polypeptides) is referred to as a "modified fibroblast" or a "modified post-natal fibroblast." A post-natal fibroblast into which one or more nucleic acids comprising nucleotide sequence encoding reprogramming factors has been introduced is referred to as a "genetically modified fibroblast" or a "genetically modified post-natal fibroblast."

As noted above, using a subject method, one or more reprogramming factors (e.g., one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1; or a subset of reprogramming factors comprising Gata4, Mef2c, Tbx5, Mesp1, and Esrrg polypeptides) are introduced into a post-natal fibroblast (e.g., the reprogramming factor polypeptide(s) themselves are introduced into a post-natal fibroblast; or a post-natal fibroblast is genetically modified with one or more nucleic acids comprising nucleotide sequences encoding reprogramming factor polypeptide(s)), and as a result, the modified fibroblast is reprogrammed into a differentiated cardiomyocyte, which may or may not occur without the fibroblast first becoming a stem cell or progenitor cell. Thus, for example, the modified or genetically modified fibroblast may or may not produce detectable levels of an early cardiac progenitor marker. For example, the modified or genetically modified fibroblast may or may not produce detectable levels of Isl1, an early cardiac progenitor marker that is transiently expressed before cardiac differentiation.

In Vivo Modification

In other embodiments, a post-natal fibroblast is genetically modified in vivo with one or more nucleic acids comprising nucleotide sequences encoding one or more reprogramming factors (e.g., 1) Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides; 2) Gata4, Mef2c, Tbx5, Mesp1, Esrrg, Nkx2.5, Srf, Zfpm2, and Myocd polypeptides; 3) Gata4, Mef2c, Tbx5, Mesp1, and Esrrg polypeptides; or 4) Gata4, Mef2c, Tbx5, Mesp1, and Esrrg polypeptides; and one or more of, Nkx2.5, Srf, Zfpm2, Myocd, Baf60c, Hand2, Isl1, Nfatc1, Smyd1, and TGFβ1 polypeptides), or is modified in vivo with one or more reprogramming factor polypeptides themselves (e.g., 1) Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides; 2) Gata4, Mef2c, Tbx5, Mesp1, Esrrg, Nkx2.5, Srf, Zfpm2, and Myocd polypeptides; 3) Gata4, Mef2c, Tbx5, Mesp1, and Esrrg polypeptides; or 4) Gata4, Mef2c, Tbx5, Mesp1, and Esrrg polypeptides; and one or more of, Nkx2.5, Srf, Zfpm2, Myocd, Baf60c, Hand2, Isl1, Nfatc1, Smyd1, and TGFβ1 polypeptides) are introduced in vivo into a post-natal fibroblast; and the modified or genetically modified fibroblasts are reprogrammed into cardiomyocytes in vivo.

For in vivo delivery of reprogramming factors (e.g., one or more nucleic acids comprising nucleotide sequences encoding reprogramming factors such as Gata4, Mef2c, Tbx5, Mesp1, and Esrrg polypeptides and optionally one or more reprogramming factors, as described above; or reprogramming factor polypeptides themselves) into a post-natal fibroblast such as a cardiac fibroblast, reprogramming factor polypeptides or nucleic acid(s) comprising nucleotide sequences encoding the reprogramming factors can be administered to an individual in need thereof intravascularly, or can be delivered directly into cardiac tissue via intramyocardial administration.

The present disclosure provides a method of generating an induced cardiomyocyte in vivo, the method generally involving administering to an individual in need thereof an effective amount of a subject reprogramming composition (described below), where the reprogramming factors induce the human cardiac fibroblast to become a cardiomyocyte, thereby generating an induced cardiomyocyte. The reprogramming composition can be a solid composition, a semi-solid composition, or a liquid composition. In some cases, the reprogramming composition is a controlled release composition, which may be a solid composition, a semi-solid composition, or a liquid composition. For example, the reprogramming composition can be a sustained release matrix.

Administration of the reprogramming composition can be achieved by various means, including via intravascular injection, and via intramyocardial delivery. For example, intramyocardial delivery can be carried out using a catheter, e.g., via a transendocardial catheter system. See, e.g., U.S. Pat. No. 7,736,346. Intramyocardial delivery via a catheter can be global, focal, or diffuse.

In Vitro Modification

In some embodiments, a post-natal fibroblast is genetically modified in vitro with one or more nucleic acids comprising nucleotide sequences encoding one or more reprogramming factors (e.g., one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1; or a subset of reprogramming factors comprising Gata4, Mef2c, Tbx5, Mesp1, and Esrrg polypeptides); or is modified with one or more reprogramming factor polypeptides themselves (e.g., one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1; or a subset of reprogramming factors comprising Gata4, Mef2c, Tbx5, Mesp1, and Esrrg polypeptides) are introduced in vitro into a post-natal fibroblast; where the modified or genetically modified fibroblasts become cardiomyocytes in vitro. Once the fibroblasts are reprogrammed into cardiomyocytes in vitro, generating induced cardiomyocytes, the induced cardiomyocytes can be introduced into an individual.

For example, in some embodiments, a subject method involves: a) genetically modifying a post-natal fibroblast in vitro with one or more nucleic acids comprising nucleotide sequences encoding one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides, where production of the encoded polypeptides in the genetically modified fibroblasts results in reprogramming of the genetically modified fibroblast into a cardiomyocyte in vitro, thereby generating an induced cardiomyocyte; and b) introducing the induced cardiomyocyte(s) into an individual. In other embodiments, a subject method involves: a) introducing one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides into a post-natal fibroblast in vitro, generating a modified fibroblast, where the modified fibroblast, as a result of introduction of the one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides, is reprogrammed into a cardiomyocyte in vitro, thereby generating an induced cardiomyocyte; and b) introducing the induced cardiomyocyte into an individual.

As another example, in some embodiments, a subject method involves: a) genetically modifying a post-natal fibroblast in vitro with one or more nucleic acids comprising nucleotide sequences encoding Gata4, Mef2c, Tbx5, Mesp1, Esrrg, Nkx2.5, Srf, Zfpm2, and Myocd polypeptides in the genetically modified fibroblasts results in reprogramming of the genetically modified fibroblast into a cardiomyocyte in vitro, thereby generating an induced cardiomyocyte; and b) introducing the induced cardiomyocyte(s) into an individual. In other embodiments, a subject method involves: a) introducing Gata4, Mef2c, Tbx5, Mesp1, Esrrg, Nkx2.5, Srf, Zfpm2, and Myocd polypeptides into a post-natal fibroblast in vitro, generating a modified fibroblast, where the modified fibroblast, as a result of introduction of the Gata4, Mef2c, Tbx5, Mesp1, Esrrg, Nkx2.5, Srf, Zfpm2, and Myocd polypeptides, is reprogrammed into a cardiomyocyte in vitro, thereby generating an induced cardiomyocyte; and b) introducing the induced cardiomyocyte into an individual.

As another example, in some embodiments, a subject method involves: a) genetically modifying a post-natal fibroblast in vitro with one or more nucleic acids comprising nucleotide sequences encoding Gata4, Mef2c, Tbx5, Mesp1, and Esrrg, and one or more of Nkx2.5, Srf, Zfpm2, Myocd, Baf60c, Hand2, Isl1, Nfatc1, Smyd1, and TGFβ1 polypeptides in the genetically modified fibroblasts results in reprogramming of the genetically modified fibroblast into a cardiomyocyte in vitro, thereby generating an induced cardiomyocyte; and b) introducing the induced cardiomyocyte(s) into an individual. In other embodiments, a subject method involves: a) introducing Gata4, Mef2c, Tbx5, Mesp1, and Esrrg, and one or more of Nkx2.5, Srf, Zfpm2, Myocd, Baf60c, Hand2, Isl1, Nfatc1, Smyd1, and TGFβ1 polypeptides into a post-natal fibroblast in vitro, generating a modified fibroblast, where the modified fibroblast, as a result of introduction of the Gata4, Mef2c, Tbx5, Mesp1, and Esrrg, and one or more of Nkx2.5, Srf, Zfpm2, Myocd, Baf60c, Hand2, Isl1, Nfatc1, Smyd1, and TGFβ1 polypeptides, is reprogrammed into a cardiomyocyte in vitro, thereby generating an induced cardiomyocyte; and b) introducing the induced cardiomyocyte into an individual.

As another example, in some embodiments, a subject method involves: a) genetically modifying a post-natal fibroblast in vitro with one or more nucleic acids comprising nucleotide sequences encoding Gata4, Mef2c, Tbx5, Mesp1, and Esrrg polypeptides in the genetically modified fibroblasts results in reprogramming of the genetically modified fibroblast into a cardiomyocyte in vitro, thereby generating an induced cardiomyocyte; and b) introducing the induced cardiomyocyte(s) into an individual. In other embodiments, a subject method involves: a) introducing Gata4, Mef2c, Tbx5, Mesp1, and Esrrg polypeptides into a post-natal fibroblast in vitro, generating a modified fibroblast, where the modified fibroblast, as a result of introduction of the Gata4, Mef2c, Tbx5, Mesp1, and Esrrg polypeptides, is reprogrammed into a cardiomyocyte in vitro, thereby generating an induced cardiomyocyte; and b) introducing the induced cardiomyocyte into an individual.

In other embodiments, a post-natal fibroblast is genetically modified in vitro with one or more nucleic acids comprising nucleotide sequences encoding one or more reprogramming factors (e.g., one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1; or a subset of reprogramming factors comprising Gata4, Mef2c, Tbx5, Mesp1, and Esrrg polypeptides); or is modified with one or more reprogramming factor polypeptides themselves (e.g., one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1; or a subset of reprogramming factors comprising Gata4, Mef2c, Tbx5, Mesp1, and Esrrg polypeptides) are introduced in vitro into a post-natal fibroblast; and the modified or genetically modified fibroblasts are introduced into an individual, where the modified or genetically modified fibroblasts are reprogrammed into cardiomyocytes in vivo.

Thus, for example, in some embodiments, a subject method involves: a) genetically modifying a post-natal fibroblast in vitro with one or more nucleic acids comprising nucleotide sequences encoding one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides; and b) introducing the genetically modified fibroblasts into an individual, where production of the one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides in the genetically modified fibroblasts results in reprogramming of the genetically modified fibroblast into a cardiomyocyte in vivo, thereby generating an induced cardiomyocyte in the individual. In other embodiments, a subject method involves: a) introducing one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides into a post-natal fibroblast in vitro, generating a modified fibroblast; and b) introducing the modified fibroblast(s) into an individual, where the modified fibroblasts, as a result of introduction of the one or more of Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides, are reprogrammed into a cardiomyocyte in vivo, thereby generating an induced cardiomyocyte in the individual.

As another example, in some embodiments, a subject method involves: a) genetically modifying a post-natal fibroblast in vitro with one or more nucleic acids comprising nucleotide sequences encoding Gata4, Mef2c, Tbx5, Mesp1, Esrrg, Nkx2.5, Srf, Zfpm2, and Myocd polypeptides; and b) introducing the genetically modified fibroblasts into an individual, where production of the Gata4, Mef2c, Tbx5, Mesp1, Esrrg, Nkx2.5, Srf, Zfpm2, and Myocd polypeptides in the genetically modified fibroblasts results in reprogramming of the genetically modified fibroblast into a cardiomyocyte in vivo, thereby generating an induced cardiomyocyte in the individual. In other embodiments, a subject method involves: a) introducing Gata4, Mef2c, Tbx5, Mesp1, Esrrg, Nkx2.5, Srf, Zfpm2, and Myocd polypeptides into a post-natal fibroblast in vitro, generating a modified fibroblast; and b) introducing the modified fibroblast(s) into an individual, where the modified fibroblasts, as a result of introduction of the Gata4, Mef2c, Tbx5, Mesp1, Esrrg, Nkx2.5, Srf, Zfpm2, and Myocd polypeptides, are reprogrammed into a cardiomyocyte in vivo, thereby generating an induced cardiomyocyte in the individual.

As another example, in some embodiments, a subject method involves: a) genetically modifying a post-natal fibroblast in vitro with one or more nucleic acids comprising nucleotide sequences encoding Gata4, Mef2c, Tbx5, Mesp1, and Esrrg, and one or more of Nkx2.5, Srf, Zfpm2, Myocd, Baf60c, Hand2, Isl1, Nfatc1, Smyd1, and TGFβ1 polypeptides; and b) introducing the genetically modified fibroblasts into an individual, where production of the Gata4, Mef2c, Tbx5, Mesp1, and Esrrg, and one or more of Nkx2.5, Srf, Zfpm2, Myocd, Baf60c, Hand2, Isl1, Nfatc1, Smyd1, and TGFβ1 polypeptides in the genetically modified fibroblasts results in reprogramming of the genetically modified fibroblast into a cardiomyocyte in vivo, thereby generating an induced cardiomyocyte in the individual. In other embodiments, a subject method involves: a) introducing Gata4, Mef2c, Tbx5, Mesp1, and Esrrg, and one or more of Nkx2.5, Srf, Zfpm2, Myocd, Baf60c, Hand2, Isl1, Nfatc1, Smyd1, and TGFβ1 polypeptides into a post-natal fibroblast in vitro, generating a modified fibroblast; and b) introducing the modified fibroblast(s) into an individual, where the modified fibroblasts, as a result of introduction of the Gata4, Mef2c, Tbx5, Mesp1, and Esrrg, and one or more of Nkx2.5, Srf, Zfpm2, Myocd, Baf60c, Hand2, Isl1, Nfatc1, Smyd1, and TGFβ1 polypeptides, are reprogrammed into a cardiomyocyte in vivo, thereby generating an induced cardiomyocyte in the individual.

As another example, in some embodiments, a subject method involves: a) genetically modifying a post-natal fibroblast in vitro with one or more nucleic acids comprising nucleotide sequences encoding Gata4, Mef2c, Tbx5, Mesp1, and Esrrg polypeptides; and b) introducing the genetically modified fibroblasts into an individual, where production of the Gata4, Mef2c, Tbx5, Mesp1, and Esrrg polypeptides in the genetically modified fibroblasts results in reprogramming of the genetically modified fibroblast into a cardiomyocyte in vivo, thereby generating an induced cardiomyocyte in the individual. In other embodiments, a subject method involves: a) introducing Gata4, Mef2c, Tbx5, Mesp1, and Esrrg polypeptides into a post-natal fibroblast in vitro, generating a modified fibroblast; and b) introducing the modified fibroblast(s) into an individual, where the modified fibroblasts, as a result of introduction of the Gata4, Mef2c, Tbx5, Mesp1, and Esrrg polypeptides, are reprogrammed into a cardiomyocyte in vivo, thereby generating an induced cardiomyocyte in the individual.

Post-Natal Fibroblasts

A post-natal fibroblast that is genetically modified with one or more nucleic acids comprising nucleotide sequences encoding reprogramming factor polypeptides, or that is modified with one or more reprogramming factor polypeptides themselves, is reprogrammed into a differentiated cardiomyocyte in a time period of from about 5 days to about 7 days, or from about 7 days to about 14 days. For example, where a population of post-natal fibroblasts is genetically modified or modified by introducing reprogramming factor polypeptides, as described above, at least about 10%, at least about 15%, at least about 20%, at least about 25%, at least about 30%, at least about 50%, at least about 75%, or more than 75% (e.g., at least about 80%, at least about 85%, at least about 90%, at least about 95%, at least about 98%, or more than 98%), of the population is reprogrammed into differentiated cardiomyocytes (induced cardiomyocytes) in a time period of from about 5 days to about 7 days, from about 7 days to about 14 days, or from about 2 weeks to about 4 weeks.

In some embodiments, where a population of post-natal fibroblasts is genetically modified with one or more nucleic acids comprising nucleotide sequences encoding reprogramming factor polypeptides, or where a population of post-natal fibroblasts is modified by introducing reprogramming factors themselves into the fibroblasts, at least about 10%, at least about 15%, at least about 20%, at least about 25%, at least about 30%, at least about 50%, at least about 75%, or more than 75% (e.g., at least about 80%, at least about 85%, at least about 90%, at least about 95%, at least about 98%, or more than 98%), of the population is cTnT$^+$ (i.e., expresses cardiac troponin T) in a time period of from about 5 days to about 7 days, from about 7 days to about 14 days, or from about 2 weeks to about 4 weeks.

In some embodiments, a subject method of generating induced cardiomyocytes involves genetically modifying a host post-natal fibroblast (or a population of host post-natal fibroblasts) in vivo with one or more nucleic acids comprising nucleotide sequences encoding reprogramming factors (e.g., Gata4, Mef2c, Tbx5, Mesp1, and Esrrg polypeptides; or any of the other sets or subsets of reprogramming factors mentioned above); generating a population of genetically modified post-natal fibroblasts. In some embodiments, a subject method of generating induced cardiomyocytes involves modifying a host post-natal fibroblast (or a population of host post-natal fibroblasts) in vivo by introducing reprogramming factor polypeptides (e.g., Gata4, Mef2c, Tbx5, Mesp1, and Esrrg polypeptides; or any of the other sets or subsets of reprogramming factors mentioned above) into host post-natal fibroblasts; generating a population of modified post-natal fibroblasts.

In some embodiments, a subject method of generating induced cardiomyocytes involves genetically modifying a host post-natal fibroblast (or a population of host post-natal fibroblasts) in vitro with one or more nucleic acids comprising nucleotide sequences encoding reprogramming factors (e.g., Gata4, Mef2c, Tbx5, Mesp1, and Esrrg polypeptides; or any of the other sets or subsets of reprogramming factors mentioned above); generating a population of genetically modified post-natal fibroblasts, and, after a time (e.g., 5 days to 7 days, 1 week to 2 weeks, or 2 weeks to 4 weeks), sorting the population of genetically modified post-natal fibroblasts to enrich for cardiomyocytes. The population of genetically modified post-natal fibroblasts can be sorted for expression of a fibroblast-specific marker, to remove any remaining fibroblasts. The population of genetically modified post-natal fibroblasts can be sorted for expression of a cardiomyocyte-specific marker.

In some embodiments, a subject method of generating induced cardiomyocytes involves modifying a host post-natal fibroblast (or a population of host post-natal fibroblasts) by introducing reprogramming factor polypeptides (e.g., Gata4, Mef2c, Tbx5, Mesp1, and Esrrg polypeptides; or any of the other sets or subsets of reprogramming factors mentioned above) into host post-natal fibroblasts; generating a population of modified post-natal fibroblasts, and, after a time (e.g., 5 days to 7 days, 1 week to 2 weeks, or 2 weeks to 4 weeks), sorting the population of modified post-natal fibroblasts to enrich for cardiomyocytes. The population of modified post-natal fibroblasts can be sorted for expression of a fibroblast-specific marker, to remove any remaining fibroblasts. The population of modified post-natal fibroblasts can be sorted for expression of a cardiomyocyte-specific marker.

In some embodiments, a host post-natal fibroblast is genetically modified with one or more nucleic acids comprising nucleotide sequences encoding reprogramming factors (e.g., Gata4, Mef2c, Tbx5, Mesp1, and Esrrg polypeptides; or any of the other sets or subsets of reprogramming factors mentioned above), or is modified by introducing reprogramming factor polypeptides (e.g., Gata4, Mef2c, Tbx5, Mesp1, and Esrrg polypeptides; or any of the other sets or subsets of reprogramming factors mentioned above) into host post-natal fibroblasts); and is also genetically modified with a nucleic acid comprising a nucleotide sequence encoding a detectable marker (e.g., a polypeptide that directly produces a detectable signal; an enzyme that produces a detectable signal upon acting on a substrate), where the detectable marker-encoding nucleotide sequence is operably linked to a cardiomyocyte-specific promoter. Suitable polypeptides that provide a direct detectable signal include a fluorescent protein such as a green fluorescent protein, a yellow fluorescent protein, a blue fluorescent protein, etc. Suitable enzymes that produce a detectable signal upon acting on a substrate include, e.g., luciferase (acting on the substrate luciferin), alkaline phosphatase, and the like. Cardiomyocyte-specific promoters include, e.g., an α-myosin heavy chain promoter; a cTnT promoter; and the like. Expression of the detectable marker can provide for detection of an induced cardiomyocyte; and can provide a means of sorting for induced cardiomyocytes.

The post-natal fibroblasts that serve as host cells for modification or genetic modification, as described above, can be from any of a variety of sources. Mammalian fibroblasts, e.g., human fibroblasts, murine (e.g., mouse) fibroblasts, rat fibroblasts, porcine fibroblasts, etc., can be used. In some embodiments, the fibroblasts are human fibroblasts. In other embodiments, the fibroblasts are mouse fibroblasts. In other embodiments, the fibroblasts are rat fibroblasts. Thus, a "post-natal fibroblast" refers to a fibroblast obtained from a post-natal mammal, or the progeny of a fibroblast obtained from a post-natal mammal.

The post-natal fibroblasts can be from any of a variety of tissue sources. For example, cardiac fibroblasts, foreskin fibroblasts, dermal fibroblasts, lung fibroblasts, etc.

In certain embodiments, the post-natal fibroblasts are cardiac fibroblasts. In certain embodiments, the post-natal fibroblasts are human cardiac fibroblasts, where the human cardiac fibroblasts can be in vivo or in vitro.

The fibroblasts can be obtained from a living individual. The fibroblasts can be obtained from tissue taken from a living individual. The fibroblasts can be obtained from a recently deceased individual who is considered a suitable organ donor. In some embodiments, the individual is screened for various genetic disorders, viral infections, etc., to determine whether the individual is a suitable source of fibroblasts, where individuals may be excluded on the basis of one or more of a genetic disorder, a viral infection, etc.

Suitable fibroblasts express markers characteristic of fibroblasts, where such markers include, e.g., vimentin, prolyl-4-hydroxylase (an intracellular enzyme involved in collagen synthesis), fibroblast-specific protein-1 (see, e.g., Strutz et al. (1995) *J. Cell Biol.* 130:393), fibroblast surface antigen, and collagen type 1. In some embodiments, the fibroblasts used as host cells are cardiac fibroblasts, where cardiac fibroblasts can be characterized as Thy1$^+$, vimentin$^+$, and are also negative for c-kit or equivalent of c-kit.

In general, a fibroblast that is suitable for use as a host cell for modification or genetic modification in accordance with a subject method is non-transformed (e.g., exhibits normal cell proliferation), and is otherwise normal.

Where the host cells for modification or genetic modification is a population of fibroblasts, the population of fibroblasts are isolated, e.g., the population of fibroblasts is composed of at least about 75% fibroblasts, at least about 80% fibroblasts, at least about 85% fibroblasts, at least about 90% fibroblasts, at least about 95% fibroblasts, at least about 98% fibroblasts, at least about 99% fibroblasts, or greater than 99% fibroblasts.

Post-natal fibroblasts can be derived from tissue of a non-embryonic subject, a neonatal infant, a child, or an adult. Post-natal fibroblasts can be derived from neonatal or post-natal tissue collected from a subject within the period from birth, including cesarean birth, to death. For example, the post-natal fibroblasts used to generate induced cardiomyocytes can be from a subject who is greater than about 10 minutes old, greater than about 1 hour old, greater than about 1 day old, greater than about 1 month old, greater than about 2 months old, greater than about 6 months old, greater than about 1 year old, greater than about 2 years old, greater than about 5 years old, greater than about 10 years old, greater than about 15 years old, greater than about 18 years old, greater than about 25 years old, greater than about 35 years old, >45 years old, >55 years old, >65 years old, >80 years old, <80 years old, <70 years old, <60 years old, <50 years old, <40 years old, <30 years old, <20 years old or <10 years old.

Methods of isolating fibroblasts from tissues are known in the art, and any known method can be used. As a non-limiting example, cardiac fibroblasts can be obtained using the method of Ieda et al. (2009) *Dev. Cell* 16:233. Foreskin fibroblasts can be obtained from foreskin tissue (i.e., the skin tissue covering the glans penis; preputium penis) of a male individual, e.g., from an 8-14 day old male individual. The fibroblasts can be obtained by mincing the foreskin tissue, then dissociating the tissue to single cells. Foreskin cell clamps can be dissociated by any means known in the art including physical de-clamping or enzymatic digestion using, for example trypsin.

As noted above, a post-natal fibroblast is genetically modified with one or more nucleic acids comprising nucleotide sequences encoding reprogramming factors (e.g., Gata4, Mef2c, Tbx5, Mesp1, and Esrrg polypeptides), or is modified by introducing reprogramming factor polypeptides themselves (e.g., Gata4, Mef2c, Tbx5, Mesp1, and Esrrg polypeptides) into the post-natal fibroblast. Amino acid sequences of such reprogramming factors are known in the art. Nucleotide sequences encoding reprogramming factors are known in the art.

Reprogramming Factors

As discussed above, a post-natal fibroblast is genetically modified with one or more nucleic acids comprising nucleotide sequences encoding reprogramming factor polypeptides; or is modified by introduction into the fibroblast of the reprogramming factor polypeptides themselves. As discussed above, a post-natal fibroblast can be modified by introduction of a set of reprogramming factors such as: 1) Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides; 2) Gata4, Mef2c, Tbx5, Mesp1, Esrrg, Nkx2.5, Srf, Zfpm2, and Myocd polypeptides; 3) Gata4, Mef2c, Tbx5, Mesp1, and Esrrg polypeptides; or 4) Gata4, Mef2c, Tbx5, Mesp1, and Esrrg polypeptides; and one or more of, Nkx2.5, Srf, Zfpm2, Myocd, Baf60c, Hand2, Isl1, Nfatc1, Smyd1, and TGFβ1 polypeptides.

Esrrg

An Esrrg polypeptide functions as a transcription activator in the absence of bound ligand; and binds specifically to an estrogen response element. See, e.g., Wang et al. (2006) *J. Biol. Chem.* 281:37773; Greschik et al. (2002) *Mol. Cell.* 9:303; and Hong et al. (1999) *J. Biol. Chem.* 274:22618.

Amino acid sequences for Esrrg polypeptides, and nucleotide sequences encoding Esrrg polypeptides, from a variety of species are known in the art. See, e.g.: 1) GenBank Accession No. NP001127757.1 (*Homo sapiens* 435 amino acid Esrrg); and GenBank Accession No. NM_001134285.2 (nucleotide sequence encoding the *Homo sapiens* 435 amino acid Esrrg); 2) GenBank Accession No. NP_001429 (*Homo sapiens* 458 amino acid Esrrg); and GenBank Accession No. NM_001438.2 (nucleotide sequence encoding the *Homo sapiens* 458 amino acid Esrrg); 3) GenBank Accession No. CAH70619 (*Homo sapiens* 442 amino acid Esrrg); 4) GenBank Accession No. AAH08218 (*Homo sapiens* 343 amino acid Esrrg); and BC008218 (nucleotide sequence encoding the *Homo sapiens* 343 amino acid Esrrg); 5) GenBank Accession No. NP_036065 (*Mus musculus* 458 amino acid Esrrg); and GenBank Accession No. NM_011935 (nucleotide sequence encoding the *Mus musculus* 458 amino acid Esrrg); 6) GenBank Accession No. EDL13041 (*Mus musculus* 435 amino acid Esrrg); 7) GenBank Accession No. NP_976081 (*Rattus norvegicus* 435 amino acid Esrrg); and GenBank Accession No. NM_203336 (nucleotide sequence encoding the *Rattus norvegicus* 435 amino acid Esrrg); 8) GenBank Accession No. AAQ90023 (*Rattus norvegicus* 458 amino acid Esrrg); and GenBank Accession No. AY341017 (nucleotide sequence encoding the *Rattus norvegicus* 458 amino acid Esrrg); 9) GenBank Accession No. DAA21449 (*Bos taurus* 435 amino acid Esrrg); and GenBank Accession No. GJ062474 (nucleotide sequence encoding the *Bos taurus* 435 amino acid Esrrg); 10) GenBank Accession No. DAA21448 (*Bos taurus* 458 amino acid Esrrg).

In some embodiments, a suitable Esrrg nucleic acid comprises a nucleotide sequence having at least about 80%, at least about 85%, at least about 90%, at least about 95%, at least about 98%, at least about 99%, or 100%, nucleotide sequence identity to a contiguous stretch of from about 1000 nucleotides to about 1100 nucleotides (nt), from about 1100 nt to about 1200 nt, or from about 1200 nt to about 1308 nt, of the nucleotide sequence depicted in FIGS. 10A and 10B (SEQ ID NO:2). In some embodiments, a suitable Esrrg nucleic acid comprises a nucleotide sequence having at least about 80%, at least about 85%, at least about 90%, at least about 95%, at least about 98%, at least about 99%, or 100%, nucleotide sequence identity to a contiguous stretch of from about 1000 nucleotides to about 1100 nucleotides (nt), from about 1100 nt to about 1200 nt, from about 1200 nt to about 1300 nt, or from about 1300 nt to 1377 nt, of the nucleotide sequence depicted in FIGS. 10A and 10B (SEQ ID NO:2).

A suitable Esrrg nucleic acid comprises a nucleotide sequence encoding a Esrrg polypeptide, where in some embodiments, a suitable Esrrg polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, or from about 400 aa to 435 aa, of the amino acid sequence depicted in FIG. 9 (SEQ ID NO:1). In some embodiments, a suitable Esrrg polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, or from about 400 aa to 435 aa, of the amino acid sequence depicted in FIG. 9 (SEQ ID NO:1). The encoded Esrrg polypeptide is biologically active, e.g., specifically to an estrogen response element.

A suitable Esrrg nucleic acid comprises a nucleotide sequence encoding a Esrrg polypeptide, where in some embodiments, a suitable Esrrg polypeptide comprises an amino acid sequence having at least about 80%, at least about 85%, at least about 90%, at least about 95%, at least about 98%, at least about 99%, or 100%, amino acid sequence identity to: a) a contiguous stretch of from about 300 amino acids (aa) to about 343 aa, of the 343-amino acid sequence depicted in FIGS. 11A and 11B (SEQ ID NO:7); b) a contiguous stretch of from about 400 amino acids to about 442 amino acids of the 442-amino acid sequence depicted in FIGS. 11A and 11B (SEQ ID NO:4); c) a contiguous stretch of from about 400 amino acids to about 457 amino acids of the 457-amino acid sequence depicted in FIGS. 11A and 11B (SEQ ID NO:6); or d) a contiguous stretch of from about 400 amino acids to about 435 amino acids of the amino acid sequence depicted in FIG. 9 (SEQ ID NO:1). In some embodiments, a suitable Esrrg polypeptide comprises an amino acid sequence having at least about 80%, at least about 85%, at least about 90%, at least about 95%, at least about 98%, at least about 99%, or 100%, amino acid sequence identity to: a) a contiguous stretch of from about 300 amino acids (aa) to about 343 aa, of the 343-amino acid sequence depicted in FIGS. 11A and 11B (SEQ ID NO:7); b) a contiguous stretch of from about 400 amino acids to about 442 amino acids of the 442-amino acid sequence depicted in FIGS. 11A and 11B (SEQ ID NO:4); c) a contiguous stretch of from about 400 amino acids to about 457 amino acids of the 457-amino acid sequence depicted in FIGS. 11A and 11B (SEQ ID NO:6); or d) a contiguous stretch of from about 400 amino acids to about 435 amino acids of the amino acid sequence depicted in FIG. 9 (SEQ ID NO:1). The encoded Esrrg polypeptide is biologically active, e.g., specifically to an estrogen response element.

Gata4

A Gata4 polypeptide is a member of the GATA family zinc-finger transcription factor that recognizes and binds a GATA motif (e.g., recognizes and binds the consensus sequence 5'-AGATAG-3') present in the promoter region of many genes. See, e.g., Huang et al. (1995) *Gene* 155:219. Amino acid sequences for Gata4 polypeptides, and nucleotide sequences encoding Gata4 polypeptides, from a variety of species are known in the art. See, e.g.: 1) GenBank Accession No. NP_002043.2 (*Homo sapiens* Gata4 amino acid sequence; and GenBank Accession No. NM_002052 (*Homo sapiens* Gata4-encoding nucleotide sequence; 2) GenBank Accession No. NP_0032118 (*Mus musculus* Gata4 amino acid sequence); and GenBank Accession No. NM_008092 (*Mus musculus* Gata4-encoding nucleotide sequence); 3) GenBank Accession No. NP_653331 (*Rattus norvegicus* Gata4 amino acid sequence); and GenBank Accession No. NM_144730 (*Rattus norvegicus* Gata4-encoding nucleotide sequence); 4) GenBank Accession No. ABI63575 (*Danio rerio* Gata4 amino acid sequence; and GenBank Accession No. DQ886664 (*Danio rerio* Gata4-encoding nucleotide sequence; and 5) GenBank Accession No. AAH71101.1 (*Xenopus laevis* Gata4 amino acid sequence); and GenBank Accession No. BC071107 (*Xenopus laevis* Gata4-encoding nucleotide sequence).

In some embodiments, a suitable Gata4 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1000 nt to about 1100 nt, from about 1100 nt to about 1200 nt, or from about 1200 nt to 1329 nt, of the nucleotide sequence depicted in FIG. 13 (SEQ ID NO:9). In some embodiments, a suitable Gata4 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1000 nt to about 1100 nt, from about 1100 nt to about 1200 nt, or from about 1200 nt to 1323 nt, of the nucleotide sequence depicted in FIG. 13 (SEQ ID NO:9).

A suitable Gata4 nucleic acid comprises a nucleotide sequence encoding a Gata4 polypeptide, where in some embodiments, a suitable Gata4 polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, or from about 400 aa to 442 aa, of the amino acid sequence depicted in FIG. 12 (SEQ ID NO:8). In some embodiments, a suitable Gata4 polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, or from about 400 aa to 441 aa, of the amino acid sequence depicted in FIG. 12 (SEQ ID NO:8). The encoded Gata4 polypeptide is biologically active, e.g., recognizes and binds a GATA motif (e.g., recognizes and binds the consensus sequence 5'-AGATAG-3') present in a promoter; and activates transcription of a gene operably linked to the promoter comprising the GATA motif.

In some embodiments, a polypeptide that is functionally equivalent to a Gata4 polypeptide (or a nucleotide sequence encoding such functional equivalent) is used. For example, in some embodiments, a Gata5 polypeptide (or a nucleotide sequence encoding a Gata5 polypeptide) is used. In other embodiments, a Gata6 polypeptide (or a nucleotide sequence encoding a Gata6 polypeptide) is used.

Amino acid sequences of Gata5 polypeptides, and nucleotide sequences encoding Gata5 polypeptides, are known in the art. See, e.g., GenBank Accession Nos.: 1) NP_536721 (*Homo sapiens* Gata5 amino acid sequence), and NM_080473 (nucleotide sequence encoding the NP_536721 amino acid sequence); 2) NP_032119 (*Mus musculus* Gata5 amino acid sequence), and NM_008093 (nucleotide sequence encoding the NP_032119 amino acid sequence); and 3) NP_001019487 (*Rattus norvegicus* Gata5 amino acid sequence), and NM_001024316 (nucleotide sequence encoding the NP_001019487 amino acid sequence).

Amino acid sequences of Gata6 polypeptides, and nucleotide sequences encoding Gata6 polypeptides, are known in the art. See, e.g., GenBank Accession Nos.: 1) NP_005248 (*Homo sapiens* Gata6 amino acid sequence), and NM_005257 (nucleotide sequence encoding the NP_005248 amino acid sequence); 2) NP_062058 (*Rattus norvegicus* Gata6 amino acid sequence) and NM_019185 (nucleotide sequence encoding the NP_062058 amino acid sequence); 3) NP_034388 (*Mus musculus* Gata6 amino acid sequence), and NM_010258 (nucleotide sequence encoding the NP_034388 amino acid sequence).

In some embodiments, a suitable functional equivalent of a Gata4 polypeptide is a polypeptide having at least about 80%, at least about 85%, at least about 90%, at least about 95%, at least about 98%, at least about 99%, or 100%, amino acid sequence identity to an amino acid sequence of a Gata5 polypeptide or a Gata6 polypeptide.

In some embodiments, a suitable nucleotide sequence encoding a functional equivalent of a Gata4 polypeptide comprises a nucleotide sequence having at least about 80%, at least about 85%, at least about 90%, at least about 95%, at least about 98%, at least about 99%, or 100%, nucleotide sequence identity to a nucleotide sequence encoding a Gata5 polypeptide or a Gata6 polypeptide.

Mef2c

Mef2c (myocyte-specific enhancer factor 2c) is a transcription activator that binds specifically to the MEF2 element (e.g., the consensus sequence: 5'-CT(A/t)(a/t)AAATAG-3') (SEQ ID NO:20) present in the regulatory regions of many muscle-specific genes. See, e.g., Andres et al. (1995) *J. Biol. Chem.* 270:23246. Mef2c can include one or more post-translational modifications, e.g., phosphorylation on Ser-59 and Ser-396; sumoylation on Lys-391; and acetylation on Lys-4.

Amino acid sequences of Mef2c polypeptides, and nucleotide sequences encoding Mef2c polypeptides, from a variety of species are known in the art. See, e.g.: 1) GenBank Accession No. XP_001056692 (*Rattus norvegicus* Mef2c amino acid sequence); and GenBank Accession No. XM_001056692 (*Rattus norvegicus* Mef2c-encoding nucleotide sequence); 2) GenBank Accession No. NP_079558.1 (*Mus musculus* Mef2c isoform 2 amino acid sequence); and GenBank Accession No. NM_025282 (*Mus musculus* Mef2c isoform 2-encoding nucleotide sequence); 3) GenBank Accession No. NP_001164008 (*Mus musculus* Mef2c isoform 1 amino acid sequence); and GenBank Accession No. NM_001170537 (*Mus musculus* Mef2c isoform 1-encoding nucleotide sequence); 4) GenBank Accession No. NP_001124477 (*Homo sapiens* Mef2c isoform 2 amino acid sequence); and GenBank Accession No. NM_001131005 (*Homo sapiens* Mef2c isoform 2-encoding nucleotide sequence); 5) GenBank Accession No. NP_002388 (*Homo sapiens* Mef2c isoform 1 amino acid sequence); and GenBank Accession No. NM_002397 (*Homo sapiens* Mef2c isoform 1-encoding nucleotide sequence).

In some embodiments, a suitable Mef2c nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1000 nt to about 1100 nt, from about 1100 nt to about 1200 nt, from about 1200 nt to 1300 nt, or from about 1300 nt to 1392 nt, of the nucleotide sequence depicted in FIG. 15 (SEQ ID NO:11).

In some embodiments, a suitable Mef2c nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1000 nt to about 1100 nt, from about 1100 nt to about 1200 nt, from about 1200 nt to 1300 nt, or from about 1300 nt to 1422 nt, of the nucleotide sequence depicted in FIG. 17 (SEQ ID NO:13).

A suitable Mef2c nucleic acid comprises a nucleotide sequence encoding a Mef2c polypeptide, where in some embodiments a suitable Mef2c polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, or from about 400 aa to 463 aa, of the amino acid sequence depicted in FIG. 14 (SEQ ID NO:10). The encoded Mef2c polypeptide is biologically active, e.g., recognizes and binds a MEF2C element in a promoter; and activates transcription of a gene operably linked to the promoter.

A suitable Mef2c nucleic acid comprises a nucleotide sequence encoding a Mef2c polypeptide, where a suitable Mef2c polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, or from about 400 aa to 473 aa, of the amino acid sequence depicted in FIG. 16 (SEQ ID NO:12). The encoded Mef2c polypeptide is biologically active, e.g., recognizes and binds a MEF2C element in a promoter; and activates transcription of a gene operably linked to the promoter.

In some embodiments, a polypeptide that is functionally equivalent to a Mef2c polypeptide (or a nucleotide sequence encoding such functional equivalent) is used. For example, in some embodiments, a Mef2a polypeptide (or a nucleotide sequence encoding a Mef2a polypeptide) is used. In other embodiments, a Mef2b polypeptide (or a nucleotide sequence encoding a Mef2b polypeptide) is used. In other embodiments, a Mef2d polypeptide (or a nucleotide sequence encoding a Mef2d polypeptide) is used.

Amino acid sequences of Mef2a, Me2b, and Mef2d polypeptides are known, as are nucleotide sequences encoding Mef2a, Me2b, and Mef2d polypeptides. See, e.g., GenBank Accession Nos.: 1) NP_005578.2 (*Homo sapiens* Mef2a isoform 1 amino acid sequence), and NM_005587 (nucleotide sequence encoding the NP_005578.2 amino acid sequence); 2) NP_001124398.1 (*Homo sapiens* Mef2a isoform 2 amino acid sequence), and NM_001130926 (nucleotide sequence encoding the NP_001124398.1 amino acid sequence); 3) NP_001124399.1 (*Homo sapiens* Mef2a isoform 3 amino acid sequence), and NM_001130927 (nucleotide sequence encoding the NP_001124399.1 amino acid sequence); 4) NP_001124400.1 (*Homo sapiens* Mef2a isoform 4 amino acid sequence), and NM_001130928 (nucleotide sequence encoding the NP_001124400.1 amino acid sequence); 5) NP_001139257.1 (*Homo sapiens* Mef2b isoform a amino acid sequence), and NM_001145785 (nucleotide sequence encoding the NP_001139257.1 amino acid sequence); 6) NP_005910.1 (*Homo sapiens* Mef2b isoform b amino acid sequence), and NM_005919 (nucleotide sequence encoding the NP_005910.1 amino acid sequence); 7) NP_032604.2 (*Mus musculus* Mef2b isoform 1 amino acid sequence), and NM_008578 (nucleotide sequence encoding the NP_032604.2 amino acid sequence); 8) NP_001038949.1 (*Mus musculus* Mef2b isoform 2 amino acid sequence), and NM_001045484 (nucleotide sequence encoding the NP_001038949.1 amino acid sequence); 9) NP_005911.1 (*Homo sapiens* Mef2d amino acid sequence), and NM_005920 (nucleotide sequence encoding the NP_005911.1 amino acid sequence); and 10) NP_598426.1 (*Mus musculus* Mef2d amino acid sequence), and NM_133665 (nucleotide sequence encoding the NP_598426.1 amino acid sequence).

In some embodiments, a suitable functional equivalent of a Mef2c polypeptide is a polypeptide having at least about 80%, at least about 85%, at least about 90%, at least about 95%, at least about 98%, at least about 99%, or 100%, amino acid sequence identity to an amino acid sequence of a Mef2a polypeptide, a Mef2b polypeptide, or a Mef2d polypeptide.

In some embodiments, a suitable nucleotide sequence encoding a functional equivalent of a Mef2c polypeptide comprises a nucleotide sequence having at least about 80%, at least about 85%, at least about 90%, at least about 95%, at least about 98%, at least about 99%, or 100%, nucleotide sequence identity to a nucleotide sequence encoding a Mef2a polypeptide, a Mef2b polypeptide, or a Mef2d polypeptide.

Tbx5

Tbx5 (T-box transcription factor 5) is a transcription factor that binds to an recognizes a T-box (e.g., an element having the consensus sequence 5'-(A/G)GGTGT-3') in the promoter region of some genes; and activates transcription of genes operably linked to such promoters.

Amino acid sequences for Tbx5 polypeptides, and nucleotide sequences encoding Tbx5 polypeptides, from a variety of species are known in the art. See, e.g.: 1) GenBank Accession No. CAA70592.1 (*Homo sapiens* Tbx5 amino acid sequence); and GenBank Accession No. Y09445 (*Homo sapiens* Tbx5-encoding nucleotide sequence); 2) GenBank Accession No. NP_000183 (*Homo sapiens* Tbx5 amino acid sequence); and GenBank Accession No. NM_000192 (*Homo sapiens* Tbx5-encoding nucleotide sequence); 3) GenBank Accession No. NP_001009964.1 (*Rattus norvegicus* Tbx5 amino acid sequence); and GenBank Accession No. NM_001009964 (*Rattus norvegicus* Tbx5-encoding nucleotide sequence; 4) GenBank Accession No. NP_035667 (*Mus musculus* Tbx5 amino acid sequence); and NM_011537 (*Mus musculus* Tbx5-encoding nucleotide sequence); 5) GenBank Accession No. NP_001079170 (*Xenopus laevis* Tbx5 amino acid sequence); and GenBank Accession No. NM_001085701 (*Xenopus laevis* Tbx5-encoding nucleotide sequence).

In some embodiments, a suitable Tbx5 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1200 nt to 1300 nt, from about 1300 nt to about 1400 nt, or from about 1400 nt to about 1500 nt, or from about 1500 nt to 1542 nt of the nucleotide sequence depicted in FIG. 19 (SEQ ID NO:15).

In some embodiments, a suitable Tbx5 nucleic acid comprises a nucleotide sequence having at least about 80%, at least about 85%, at least about 90%, at least about 95%, at least about 98%, at least about 99%, or 100%, nucleotide sequence identity to a contiguous stretch of from about 900 nucleotides to about 1000 nucleotides (nt), from about 1200 nt to 1300 nt, from about 1300 nt to about 1400 nt, or from about 1400 nt to about 1500 nt, or from about 1500 nt to 1557, of the nucleotide sequence depicted in FIG. 21 (SEQ ID NO:17).

A suitable Tbx5 nucleic acid comprises a nucleotide sequence encoding a Tbx5 polypeptide. In some embodiments, a suitable Tbx5 polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, from about 400 aa to about 500 aa, or from about 500 aa to 513 aa, of the amino acid sequence depicted in FIG. 18 (SEQ ID NO:14). In some embodiments, a suitable Tbx5 polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, from about 400 aa to about 500 aa, or from about 500 aa to 518 aa, of the amino acid sequence depicted in FIG. 20 (SEQ ID NO:16). The encoded Tbx5 polypeptide is biologically active, e.g., recognizes and binds a Tbx5 binding site (e.g., an element having the consensus sequence 5'-(A/G)GGTGT-3') in a promoter; and activates transcription of a gene operably linked to the promoter.

A suitable Tbx5 nucleic acid comprises a nucleotide sequence encoding a Tbx5 polypeptide, where in some embodiments a suitable Tbx5 polypeptide comprises an amino acid sequence having at least about 80%, at least about 85%, at least about 90%, at least about 95%, at least about 98%, at least about 99%, or 100%, amino acid sequence identity to a contiguous stretch of from about 350 amino acids (aa) to about 400 aa, from about 400 aa to about 500 aa, or from about 500 aa to 518 aa, of the amino acid sequence depicted in FIG. 20 (SEQ ID NO:16). The encoded Tbx5 polypeptide is biologically active, e.g., recognizes and binds a Tbx5 binding site (e.g., an element having the consensus sequence 5'-(A/G)GGTGT-3') in a promoter; and activates transcription of a gene operably linked to the promoter.

Mesp1

In some embodiments, a suitable mesoderm posterior protein 1 (Mesp1) nucleic acid comprises a nucleotide sequence having at least about 80%, at least about 85%, at least about 90%, at least about 95%, at least about 98%, at least about 99%, or 100%, nucleotide sequence identity to a contiguous stretch of from about 600 nucleotides to about 800 nucleotides (nt), or 804 nt, of the nucleotide sequence depicted in FIG. 23 (SEQ ID NO:19).

A suitable Mesp1 nucleic acid comprises a nucleotide sequence encoding a Mesp1 polypeptide, where in some embodiments, a suitable Mesp1 polypeptide comprises an amino acid sequence having at least about 80%, at least about 85%, at least about 90%, at least about 95%, at least about 98%, at least about 99%, or 100%, amino acid sequence identity to a contiguous stretch of from about 200 amino acids (aa) to about 250 aa, or from about 250 aa to 268 aa, of the amino acid sequence depicted in FIG. 22 (SEQ ID NO:18). The encoded Mesp1 polypeptide is biologically active.

It has been found that introduction of one or more nucleic acids comprising nucleotide sequences encoding reprogramming factors Gata4, Mef2c, Mesp1, Tbx5, and Esrrg is sufficient to reprogram a post-natal fibroblast into a cardiomyocyte. Thus, a post-natal fibroblast can be reprogrammed to become a cardiomyocyte without the need for introducing an induction factor (e.g., any other exogenous polypeptide; any other nucleic acid encoding any other exogenous polypeptide) that would reprogram a fibroblast into a stem cell or progenitor cell into the post-natal fibroblast. For example, a subject method does not require and does not involve introducing into a post-natal fibroblast any of an exogenous Sox2 polypeptide, an exogenous Oct-3/4 polypeptide, an exogenous c-Myc polypeptide, an exogenous Klf4 polypeptide, an exogenous Nanog polypeptide, or an exogenous Lin28 polypeptide. A subject method does not require and does not involve introducing into a post-natal fibroblast a nucleic acid(s) comprising nucleotide sequences encoding any of Sox2, Oct-3/4, c-Myc, Klf4, Nanog, or any other polypeptide that would reprogram a fibroblast into a stem cell or progenitor cell.

As noted above, to generate an induced cardiomyocyte, a post-natal fibroblast is genetically modified with one or more nucleic acids comprising nucleotide sequences encoding one or more reprogramming factors. Induced cardiomyocytes express one or more cardiomyocyte-specific markers, where cardiomyocyte-specific markers include, but are not limited to, cardiac troponin I, cardiac troponin-C, tropomyosin, caveolin-3, myosin heavy chain, myosin light chain-2a, myosin light chain-2v, ryanodine receptor, sarcomeric α-actinin, Nkx2.5, connexin 43, and atrial natriuretic factor. Induced cardiomyocytes can also exhibit sarcomeric structures. Induced cardiomyocytes exhibit increased expression of cardiomyocyte-specific genes ACTC1 (cardiac α-actin), ACTN2 (actinin a2), MYH6 (α-myosin heavy chain), RYR2 (ryanodine receptor 2), MYL2 (myosin regulatory light chain 2, ventricular isoform), MYL7 (myosin regulatory light chain, atrial isoform), TNNT2 (troponin T type 2, cardiac), and NPPA (natriuretic peptide precursor type A), PLN (phospholamban). Expression of fibroblasts markers such as Col1a2 (collagen 1a2) is downregulated in induced cardiomyocytes, compared to fibroblasts from which the iCM is derived.

The expression of various markers specific to cardiomyocytes is detected by conventional biochemical or immunochemical methods (e.g., enzyme-linked immunosorbent assay; immunohistochemical assay; and the like). Alternatively, expression of nucleic acid encoding a cardiomyocyte-specific marker can be assessed. Expression of cardiomyocyte-specific marker-encoding nucleic acids in a cell can be confirmed by reverse transcriptase polymerase chain reaction (RT-PCR) or hybridization analysis, molecular biological methods which have been commonly used in the past for amplifying, detecting and analyzing mRNA coding for any marker proteins. Nucleic acid sequences coding for markers specific to cardiomyocytes are known and are available through public data bases such as GenBank; thus, marker-specific sequences needed for use as primers or probes is easily determined.

Induced cardiomyocytes can also exhibit spontaneous contraction. Whether an induced cardiomyocyte exhibits spontaneous contraction can be determined using standard electrophysiological methods (e.g., patch clamp); a suitable method is described in the Examples.

In some embodiments, induced cardiomyocytes can exhibit spontaneous $Ca^{2+}$ oscillations. $Ca^{2+}$ oscillations can be detected using standard methods, e.g., using any of a variety of calcium-sensitive dyes. intracellular $Ca^{2+}$ ion-detecting dyes include, but are not limited to, fura-2, bis-fura 2, indo-1, Quin-2, Quin-2 AM, Benzothiaza-1, Benzothiaza-2, indo-5F, Fura-FF, BTC, Mag-Fura-2, Mag-Fura-5, Mag-Indo-1, fluo-3, rhod-2, rhod-3, fura-4F, fura-5F, fura-6F, fluo-4, fluo-5F, fluo-5N, Oregon Green 488 BAPTA, Calcium Green, Calcein, Fura-C18, Calcium Green-C18, Calcium Orange, Calcium Crimson, Calcium Green-5N, Magnesium Green, Oregon Green 488 BAPTA-1, Oregon Green 488 BAPTA-2, X-rhod-1, Fura Red, Rhod-5F, Rhod-5N, X-Rhod-5N, Mag-Rhod-2, Mag-X-Rhod-1, Fluo-5N, Fluo-5F, Fluo-4FF, Mag-Fluo-4, Aequorin, dextran conjugates or any other derivatives of any of these dyes, and others (see, e.g., the catalog or Internet site for Molecular Probes, Eugene, see, also, Nuccitelli, ed., *Methods in Cell Biology, Volume 40: A Practical Guide to the Study of Calcium in Living Cells*, Academic Press (1994); Lambert, ed., *Calcium Signaling Protocols* (Methods in Molecular Biology Volume 114), Humana Press (1999); W. T. Mason, ed., *Fluorescent and Luminescent Probes for Biological Activity. A Practical Guide to Technology for Quantitative Real-Time Analysis*, Second Ed, Academic Press (1999); *Calcium Signaling Protocols* (Methods in Molecular Biology), 2005, D. G. Lamber, ed., Humana Press.).

Introduction of Exogenous Re-Programming Factor Polypeptide into a Post-Natal Fibroblast In some embodiments, introduction of exogenous reprogramming factor polypeptides into a post-natal fibroblast is achieved by contacting the post-natal fibroblast with exogenous reprogramming factor polypeptides, wherein the exogenous reprogramming factor polypeptides are taken up into the cell.

In some embodiments, each of an exogenous reprogramming factor polypeptides comprises a protein transduction domain. As a non-limiting example, one or more of an exogenous Gata4 polypeptide, an exogenous Mef2C polypeptide, an exogenous Tbx5 polypeptide, an exogenous Mesp1 polypeptide, and an exogenous Esrrg polypeptide is linked, covalently or non-covalently, to a protein transduction domain.

"Protein Transduction Domain" or PTD refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of a reprogramming factor polypeptide. In some embodiments, a PTD is covalently linked to the carboxyl terminus of a reprogramming factor polypeptide.

Exemplary protein transduction domains include but are not limited to a minimal undecapeptide protein transduction domain (corresponding to residues 47-57 of HIV-1 TAT comprising YGRKKRRQRRR; SEQ ID NO:21); a polyarginine sequence comprising a number of arginines sufficient to direct entry into a cell (e.g., 3, 4, 5, 6, 7, 8, 9, 10, or 10-50 arginines); a VP22 domain (Zender et al., Cancer Gene Ther. 2002 June; 9(6):489-96); an *Drosophila* Antennapedia protein transduction domain (Noguchi et al., Diabetes 2003;

52(7):1732-1737); a truncated human calcitonin peptide (Trehin et al. Pharm. Research, 21:1248-1256, 2004); polylysine (Wender et al., PNAS, Vol. 97:13003-13008); RRQRRTSKLMKR (SEQ ID NO:22); Transportan GWTLNSAGYLLGKINLKALAALAKKIL (SEQ ID NO:23); KALAWEAKLAKALAKALAKHLAKALAKA-LKCEA (SEQ ID NO:24); and RQIKIWFQNRRMKWKK (SEQ ID NO:25). Exemplary PTDs include but are not limited to, YGRKKRRQRRR (SEQ ID NO:21), RKKRRQRRR (SEQ ID NO:26); an arginine homopolymer of from 3 arginine residues to 50 arginine residues; Exemplary PTD domain amino acid sequences include, but are not limited to, any of the following:

```
                            (SEQ ID NO: 21)
YGRKKRRQRRR;

(SEQ ID NO: 26)
RKKRRQRR;

(SEQ ID NO: 27)
YARAAARQARA;

(SEQ ID NO: 28)
THRLPRRRRRR;
and (SEQ ID NO: 29)
GGRRARRRRRR.
```

In some embodiments, an exogenous reprogramming factor polypeptide (e.g., one or more of Gata4, Mef2c, Tbx5, Mesp1, and Esrrg polypeptides) comprises an arginine homopolymer of from 3 arginine residues to 50 arginine residues, e.g., from 3 to 6 arginine residues, from 6 to 10 arginine residues, from 10 to 20 arginine residues, from 20 to 30 arginine residues, from 30 to 40 arginine residues, or from 40 to 50 arginine residues. In some embodiments, an exogenous reprogramming factor polypeptide comprises six Arg residues covalently linked (e.g., by a peptide bond) at the amino terminus of the reprogramming factor polypeptide. In some embodiments, an exogenous reprogramming factor polypeptide comprises six Arg residues covalently linked (e.g., by a peptide bond) at the carboxyl terminus of the reprogramming factor polypeptide.

Exogenous reprogramming factor polypeptides that are introduced into a host post-natal fibroblast can be purified, e.g., at least about 75% pure, at least about 80% pure, at least about 85% pure, at least about 90% pure, at least about 95% pure, at least about 98% pure, at least about 99% pure, or more than 99% pure, e.g., free of proteins other than reprogramming factor(s) being introduced into the cell and free of macromolecules other than the reprogramming factor(s) being introduced into the cell.

Genetic Modification of a Post-Natal Fibroblast

In some embodiments, introduction of exogenous reprogramming factor polypeptides (e.g., 1) Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides; 2) Gata4, Mef2c, Tbx5, Mesp1, Esrrg, Nkx2.5, Srf, Zfpm2, and Myocd polypeptides; 3) Gata4, Mef2c, Tbx5, Mesp1, and Esrrg polypeptides; or 4) Gata4, Mef2c, Tbx5, Mesp1, and Esrrg polypeptides; and one or more of, Nkx2.5, Srf, Zfpm2, Myocd, Baf60c, Hand2, Isl1, Nfatc1, Smyd1, and TGFβ1 polypeptides) into a post-natal fibroblast is achieved by genetic modification of the post-natal fibroblast with one or more exogenous nucleic acids comprising nucleotide sequences encoding reprogramming factor polypeptides. In the following discussion, one or more exogenous nucleic acids comprising nucleotide sequences encoding reprogramming factor polypeptides are referred to generically as "one or more exogenous nucleic acids."

The one or more exogenous nucleic acids comprising nucleotide sequences encoding the above-noted exogenous reprogramming factor polypeptides can be a recombinant expression vector, where suitable vectors include, e.g., recombinant retroviruses, lentiviruses, and adenoviruses; retroviral expression vectors, lentiviral expression vectors, nucleic acid expression vectors, and plasmid expression vectors. In some cases, the one or more exogenous nucleic acids is integrated into the genome of a host post-natal fibroblast and its progeny. In other cases, the one or more exogenous nucleic acids persists in an episomal state in the host post-natal fibroblast and its progeny. In some cases, an endogenous, natural version of the reprogramming factor-encoding nucleic acid may already exist in the cell but an additional "exogenous gene" is added to the host post-natal fibroblast to increase expression of the reprogramming factor. In other cases, the exogenous reprogramming factor-encoding nucleic acid encodes a reprogramming factor polypeptide having an amino acid sequence that differs by one or more amino acids from a polypeptide encoded by an endogenous reprogramming factor-encoding nucleic acid within the host post-natal fibroblast.

In some embodiments, a post-natal fibroblast is genetically modified with five separate expression constructs (expression vectors), each comprising a nucleotide sequence encoding one reprogramming factor polypeptide. In some embodiments, a post-natal fibroblast is genetically modified with two, three, or four separate expression constructs (expression vectors) encoding Gata4, Mef2c, Tbx5, Mesp1, and Esrrg polypeptides. In some embodiments, a single expression construct will comprise nucleotide sequences encoding all five of Gata4, Mef2c, Tbx5, Mesp1, and Esrrg polypeptides.

In some embodiments, one or more exogenous nucleic acids comprising nucleotide sequences encoding reprogramming factor polypeptides is introduced into a single post-natal fibroblast (e.g., a single post-natal fibroblast host cell) in vitro). In other embodiments, one or more exogenous nucleic acids comprising nucleotide sequences encoding reprogramming factor polypeptides is introduced into a population of post-natal fibroblasts (e.g., a population of host post-natal fibroblasts) in vitro. In some embodiments, one or more exogenous nucleic acids comprising nucleotide sequences encoding reprogramming polypeptides is introduced into a post-natal fibroblast (e.g., a single post-natal fibroblast or a population of post-natal fibroblasts) in vivo.

Where a population of post-natal fibroblasts is genetically modified (in vitro or in vivo) with one or more exogenous nucleic acids comprising nucleotide sequences encoding reprogramming factor polypeptides, the one or more exogenous nucleic acids can be introduced into greater than 20% of the total population of post-natal fibroblasts, e.g., 25%, 30%, 35%, 40%, 44%, 50%, 57%, 62%, 70%, 74%, 75%, 80%, 90%, or other percent of cells greater than 20%.

In some embodiments, the one or more nucleic acids comprising nucleotide sequences encoding reprogramming factor polypeptides is/are an expression construct that provides for production of the one or more reprogramming factor polypeptides in the genetically modified host post-natal fibroblast cell. In some embodiments, the expression construct is a viral construct, e.g., a recombinant adeno-associated virus construct (see, e.g., U.S. Pat. No. 7,078, 387), a recombinant adenoviral construct, a recombinant lentiviral construct, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641648, 1999; Ali et al., Hum Mol Genet. 5:591594, 1996; Srivastava in WO 93/09239, Samulski et al., J. Vir. (1989) 63:3822-3828; Mendelson et al., Virol. (1988) 166: 154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

In some embodiments, a reprogramming factor-encoding nucleotide sequence (e.g., a Gata4-encoding nucleotide sequence, an Mef2c-encoding nucleotide sequence, a Tbx5-encoding nucleotide sequence) is operably linked to a control element, e.g., a transcriptional control element, such as a promoter. The transcriptional control element is functional in a eukaryotic cell, e.g., a mammalian cell. Suitable transcriptional control elements include promoters and enhancers. In some embodiments, the promoter is constitutively active. In other embodiments, the promoter is inducible.

Non-limiting examples of suitable eukaryotic promoters (promoters functional in a eukaryotic cell) include CMV immediate early, HSV thymidine kinase, early and late SV40, long terminal repeats (LTRs) from retrovirus, and mouse metallothionein-I.

In some embodiments, a reprogramming factor-encoding nucleotide sequence is operably linked to a cardiac-specific transcriptional regulator element (TRE), where TREs include promoters and enhancers. Suitable TREs include, but are not limited to, TREs derived from the following genes: myosin light chain-2, α-myosin heavy chain, AE3, cardiac troponin C, and cardiac actin. Franz et al. (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Selection of the appropriate vector and promoter is well within the level of ordinary skill in the art. The expression vector may also contain a ribosome binding site for translation initiation and a transcription terminator. The expression vector may also include appropriate sequences for amplifying expression.

Examples of suitable mammalian expression vectors (expression vectors suitable for use in mammalian host cells) include, but are not limited to: recombinant viruses, nucleic acid vectors, such as plasmids, bacterial artificial chromosomes, yeast artificial chromosomes, human artificial chromosomes, cDNA, cRNA, and polymerase chain reaction (PCR) product expression cassettes. Examples of suitable promoters for driving expression of reprogramming factor polypeptide-encoding nucleotide sequence include, but are not limited to, retroviral long terminal repeat (LTR) elements; constitutive promoters such as CMV, HSV1-TK, SV40, EF-1α, β-actin; phosphoglycerol kinase (PGK), and inducible promoters, such as those containing Tet-operator elements. In some cases, the mammalian expression vector(s) encodes, in addition to exogenous reprogramming factor polypeptides, a marker gene that facilitates identification or selection of cells that have been transfected or infected. Examples of marker genes include, but are not limited to, genes encoding fluorescent proteins, e.g., enhanced green fluorescent protein, Ds-Red (DsRed: *Discosoma* sp. red fluorescent protein (RFP); Bevis and Glick (2002) *Nat. Biotechnol.* 20:83), yellow fluorescent protein, mCherry, and cyanofluorescent protein; and genes encoding proteins conferring resistance to a selection agent, e.g., a neomycin resistance gene, a puromycin resistance gene, a blasticidin resistance gene, and the like.

Examples of suitable viral vectors include, but are not limited, viral vectors based on retroviruses (including lentiviruses); adenoviruses; and adeno-associated viruses. An example of a suitable retrovirus-based vector is a vector based on murine moloney leukemia virus (MMLV); however, other recombinant retroviruses may also be used, e.g., Avian Leukosis Virus, Bovine Leukemia Virus, Murine Leukemia Virus (MLV), Mink-Cell focus-Inducing Virus, Murine Sarcoma Virus, Reticuloendotheliosis virus, Gibbon Abe Leukemia Virus, Mason Pfizer Monkey Virus, or Rous Sarcoma Virus, see, e.g., U.S. Pat. No. 6,333,195.

In other cases, the retrovirus-based vector is a lentivirus-based vector, (e.g., Human Immunodeficiency Virus-1 (HIV-1); Simian Immunodeficiency Virus (SIV); or Feline Immunodeficiency Virus (FIV)), See, e.g., Johnston et al., (1999), Journal of Virology, 73(6):4991-5000 (FIV); Negre D et al., (2002), Current Topics in Microbiology and Immunology, 261:53-74 (SIV); Naldini et al., (1996), Science, 272:263-267 (HIV).

The recombinant retrovirus may comprise a viral polypeptide (e.g., retroviral env) to aid entry into the target cell. Such viral polypeptides are well-established in the art, see, e.g., U.S. Pat. No. 5,449,614. The viral polypeptide may be an amphotropic viral polypeptide, e.g., amphotropic env, which aids entry into cells derived from multiple species, including cells outside of the original host species. The viral polypeptide may be a xenotropic viral polypeptide that aids entry into cells outside of the original host species. In some embodiments, the viral polypeptide is an ecotropic viral polypeptide, e.g., ecotropic env, which aids entry into cells of the original host species.

Examples of viral polypeptides capable of aiding entry of retroviruses into cells include but are not limited to: MMLV amphotropic env, MMLV ecotropic env, MMLV xenotropic env, vesicular stomatitis virus-g protein (VSV-g), HIV-1 env, Gibbon Ape Leukemia Virus (GALV) env, RD114, FeLV-C, FeLV-B, MLV 10A1 env gene, and variants thereof, including chimeras. See e.g., Yee et al., (1994), Methods Cell Biol., Pt A:99-112 (VSV-G); U.S. Pat. No. 5,449,614. In some cases, the viral polypeptide is genetically modified to promote expression or enhanced binding to a receptor.

In general, a recombinant virus is produced by introducing a viral DNA or RNA construct into a producer cell. In some cases, the producer cell does not express exogenous genes. In other cases, the producer cell is a "packaging cell" comprising one or more exogenous genes, e.g., genes encoding one or more gag, pol, or env polypeptides and/or one or more retroviral gag, pol, or env polypeptides. The retroviral packaging cell may comprise a gene encoding a viral polypeptide, e.g., VSV-g that aids entry into target cells. In some cases, the packaging cell comprises genes encoding one or more lentiviral proteins, e.g., gag, pol, env, vpr, vpu, vpx, vif, tat, rev, or nef. In some cases, the packaging cell comprises genes encoding adenovirus proteins such as E1A or E1B or other adenoviral proteins. For example, proteins supplied by packaging cells may be retrovirus-derived proteins such as gag, pol, and env; lentivirus-derived proteins such as gag, pol, env, vpr, vpu, vpx, vif, tat, rev, and nef; and adenovirus-derived proteins such as E1A and E1B. In many examples, the packaging cells supply proteins derived from a virus that differs from the virus from which the viral vector derives.

Packaging cell lines include but are not limited to any easily-transfectable cell line. Packaging cell lines can be based on 293T cells, NIH3T3, COS or HeLa cell lines. Packaging cells are often used to package virus vector plasmids deficient in at least one gene encoding a protein required for virus packaging. Any cells that can supply a protein or polypeptide lacking from the proteins encoded by such virus vector plasmid may be used as packaging cells. Examples of packaging cell lines include but are not limited to: Platinum-E (Plat-E); Platinum-A (Plat-A); BOSC 23 (ATCC CRL 11554); and Bing (ATCC CRL 11270), see, e.g., Morita et al., (2000), Gene Therapy, 7:1063-1066; Onishi et al., (1996), Experimental Hematology, 24:324-329; U.S. Pat. No. 6,995,009. Commercial packaging lines are also useful, e.g., Ampho-Pak 293 cell line, Eco-Pak 2-293 cell line, RetroPack PT67 cell line, and Retro-X Universal Packaging System (all available from Clontech).

The retroviral construct may be derived from a range of retroviruses, e.g., MMLV, HIV-1, SIV, FIV, or other retrovirus described herein. The retroviral construct may encode all viral polypeptides necessary for more than one cycle of replication of a specific virus. In some cases, the efficiency of viral entry is improved by the addition of other factors or other viral polypeptides. In other cases, the viral polypeptides encoded by the retroviral construct do not support more than one cycle of replication, e.g., U.S. Pat. No. 6,872,528. In such circumstances, the addition of other factors or other viral polypeptides can help facilitate viral entry. In an exemplary embodiment, the recombinant retrovirus is HIV-1 virus comprising a VSV-g polypeptide but not comprising a HIV-1 env polypeptide.

The retroviral construct may comprise: a promoter, a multi-cloning site, and/or a resistance gene. Examples of promoters include but are not limited to CMV, SV40, EF1α, β-actin; retroviral LTR promoters, and inducible promoters. The retroviral construct may also comprise a packaging signal (e.g., a packaging signal derived from the MFG vector; a psi packaging signal). Examples of some retroviral constructs known in the art include but are not limited to: pMX, pBabeX or derivatives thereof. See e.g., Onishi et al., (1996), Experimental Hematology, 24:324-329. In some cases, the retroviral construct is a self-inactivating lentiviral vector (SIN) vector, see, e.g., Miyoshi et al., (1998), J. Virol., 72(10):8150-8157. In some cases, the retroviral construct is LL-CG, LS-CG, CL-CG, CS-CG, CLG or MFG. Miyoshi et al., (1998), J. Virol., 72(10):8150-8157; Onishi et al., (1996), Experimental Hematology, 24:324-329; Riviere et al., (1995), PNAS, 92:6733-6737. Virus vector plasmids (or constructs), include: pMXs, pMxs-IB, pMXs-puro, pMXs-neo (pMXs-IB is a vector carrying the blasticidin-resistant gene in stead of the puromycin-resistant gene of pMXs-puro) Kimatura et al., (2003), Experimental Hematology, 31: 1007-1014; MFG Riviere et al., (1995), Proc. Natl. Acad. Sci. U.S.A., 92:6733-6737; pBabePuro; Morgenstern et al., (1990), Nucleic Acids Research, 18:3587-3596; LL-CG, CL-CG, CS-CG, CLG Miyoshi et al., (1998), Journal of Virology, 72:8150-8157 and the like as the retrovirus system, and pAdex1 Kanegae et al., (1995), Nucleic Acids Research, 23:3816-3821 and the like as the adenovirus system. In exemplary embodiments, the retroviral construct comprises blasticidin (e.g., pMXs-IB), puromycin (e.g., pMXs-puro, pBabePuro); or neomycin (e.g., pMXs-neo). See, e.g., Morgenstern et al., (1990), Nucleic Acids Research, 18:3587-3596.

Methods of producing recombinant viruses from packaging cells and their uses are well established; see, e.g., U.S. Pat. Nos. 5,834,256; 6,910,434; 5,591,624; 5,817,491; 7,070,994; and 6,995,009. Many methods begin with the introduction of a viral construct into a packaging cell line. The viral construct may be introduced into a host fibroblast by any method known in the art, including but not limited to: a calcium phosphate method, a lipofection method (Felgner et al. (1987) *Proc. Natl. Acad. Sci. U.S.A.* 84:7413-7417), an electroporation method, microinjection, Fugene transfection, and the like, and any method described herein.

One or more nucleic acids encoding reprogramming factors can be introduced into a host cell using a variety of well known techniques, such as non-viral based transfection of the cell. In an exemplary aspect a construct is incorporated into a vector and introduced into a host cell. Introduction into the cell may be performed by any non-viral based transfection known in the art, such as, but not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like), or cell fusion. Other methods of transfection include transfection reagents such as Lipofectamine™, Dojindo Hilymax™, Fugene™, jetPEI™, Effectene™, and DreamFect™.

Additional Polypeptides

In some embodiments, a subject method involves introducing into a post-natal fibroblast reprogramming factors Gata4, Mef2c, Tbx5, Mesp1, and Esrrg; and one or more of an exogenous Nkx2-5 polypeptide, an exogenous Smyd1 polypeptide, an exogenous Myocd polypeptide, an exogenous Baf60c polypeptide, an exogenous Srf polypeptide, an exogenous Isl1 polypeptide, an exogenous Hand2 polypeptide, an exogenous Zfpm2 polypeptide, an exogenous Nfatc1 polypeptide, and an exogenous TGFβ1 polypeptide. In some embodiments, a subject method involves introducing into a post-natal fibroblast a nucleic acid(s) comprising nucleotide sequences encoding Gata4, Mef2c, Tbx5, Mesp1, and Esrrg; and one or more of an exogenous Nkx2-5 polypeptide, an exogenous Smyd1 polypeptide, an exogenous Myocd polypeptide, an exogenous Baf60c polypeptide, an exogenous Srf polypeptide, an exogenous Isl1 polypeptide, an exogenous Hand2 polypeptide, an exogenous Zfpm2 polypeptide, an exogenous Nfatc1 polypeptide, and an exogenous TGFβ1 polypeptide.

Amino acid sequences of Nkx2.5, Srf, Zfpm2, Myocd, Baf60c, Hand2, Isl1, Nfatc1, Smyd1, and TGFβ1 polypeptides are known in the art, as are nucleotide sequences encoding the polypeptides. See, e.g., GenBank Accession Nos:

1) AAR88511.1 (*Homo sapiens* BAF60c; amino acid sequence), and AY450431 (nucleotide sequence encoding the AAR88511.1 amino acid sequence);

2) AAR88510.1 (*Homo sapiens* BAF60c; amino acid sequence), and AY450430 (nucleotide sequence encoding the AAR88510.1 amino acid sequence);

3) NP_068808 (*Homo sapiens* Hand2 amino acid sequence), and NM_021973 (nucleotide sequence encoding the NP_068808 amino acid sequence);

4) NP_004378.1 (*Homo sapiens* NKX2-5 amino acid sequence), and NM_004387 (nucleotide sequence encoding the NP_004378.1 amino acid sequence;

5) NP_001159648.1 (*Homo sapiens* NKX2-5 amino acid sequence), and NM_001166176 (nucleotide sequence encoding the NP_001159648.1 amino acid sequence;

6) NP_001159647.1 (*Homo sapiens* Nkx2-5 amino acid sequence), and NM_001166175 (nucleotide sequence encoding the NP_001159647.1 amino acid sequence;

7) NP_002193.2 (*Homo sapiens* Isl1 amino acid sequence), and NM_002202 (nucleotide sequence encoding the NP_002193.2 amino acid sequence);

8) NP_001139785.1 (*Homo sapiens* Myocd amino acid sequence), and NM_001146313 (nucleotide sequence encoding the NP_001139785.1 amino acid sequence);

9) NP_001139784.1 (*Homo sapiens* Myocd amino acid sequence), and NM_001146312 (nucleotide sequence encoding the NP_001139784.1 amino acid sequence);

10) NP_705832.1 (*Homo sapiens* Myocd amino acid sequence), and NM_153604 (nucleotide sequence encoding the NP_705832.1 amino acid sequence);

11) NP_938015.1 (*Homo sapiens* Smyd1 amino acid sequence), and NM_198274 (nucleotide sequence encoding the NP_938015.1 amino acid sequence);

12) NP_003122.1 (*Homo sapiens* Srf amino acid sequence), and NM_003131 (nucleotide sequence encoding the NP_003122.1 amino acid sequence;

13) NP_036214 (*Homo sapiens* zinc finger protein multitype 2 (Zfpm2) amino acid sequence); and NM_012082 (nucleotide sequence encoding the NP_036214 amino acid sequence;

14) NP_765978 (*Homo sapiens* nuclear factor of activated T-cells, cytoplasmic 1, isoform A; Nfatc1, isoform A) and NM_172390 (nucleotide sequence encoding the NP_765978 amino acid sequence); NP_006153.2 (*Homo sapiens* Nfatc1, isoform B) and NM_006162 (nucleotide sequence encoding the NP_006153 amino acid sequence); NP_765975 (*Homo sapiens* Nfatc1, isoform C); and NM_172387 (nucleotide sequence encoding the NP_765975 amino acid sequence); NP_765976 (*Homo sapiens* Nfatc1, isoform D); and NM_172388 (nucleotide sequence encoding the NP_765976 amino acid sequence); and NP_765977 (*Homo sapiens* Nfatc1, isoform E); and NM_172389 (nucleotide sequence encoding the NP_765977 amino acid sequence);

15) NP_004603 (*Homo sapiens* transforming growth factor-beta type 1, isoform 1); and NM_004612 (nucleotide sequence encoding the NP_004603 amino acid sequence); NP_001124388 (*Homo sapiens* transforming growth factor-beta type 1, isoform 2); and NM_001130916 (nucleotide sequence encoding the NP_001124388 amino acid sequence).

Amino acid sequences of Nkx2.5, Srf, Zfpm2, Myocd, Baf60c, Hand2, Isl1, Nfatc1, Smyd1, and TGFβ1 polypeptides include amino acid sequences having at least about 85%, at least about 90%, at least about 95%, at least about 98%, at least about 99%, or 100%, amino acid sequence identity to an amino acid sequence set forth in one of the aforementioned GenBank entries.

Nucleotide sequences encoding Nkx2.5, Srf, Zfpm2, Myocd, Baf60c, Hand2, Isl1, Nfatc1, Smyd1, and TGFβ1 polypeptides include nucleotide sequences having at least about 85%, at least about 90%, at least about 95%, at least about 98%, at least about 99%, or 100%, nucleotide sequence identity to a nucleotide sequence set forth in one of the aforementioned GenBank entries.

Additional Factors

A post-natal fibroblast can be modified or genetically modified as described above; and can also be contacted with one or more additional factors which can be added to the culture system, e.g., the one or more additional factors can be included as additives in the culture medium.

Examples of such additional factors include, but are not limited to: histone deacetylase (HDAC) inhibitors, see, e.g. Huangfu et al. (2008) Nature Biotechnol. 26:795-797; Huangfu et al. (2008) Nature Biotechnol. 26: 1269-1275; DNA demethylating agents, see, e.g., Mikkelson et al (2008) Nature 454, 49-55; histone methyltransferase inhibitors, see, e.g., Shi et al. (2008) Cell Stem Cell 2:525-528; L-type calcium channel agonists, see, e.g., Shi et al. (2008) 3:568-574; Wnt3a, see, e.g., Marson et al. (2008) Cell 134:521-533; siRNA, see, e.g., Zhao et al. (2008) Cell Stem Cell 3: 475-479.

As one example, thymosin beta4 (Tβ4) can be used. Amino acid sequences of Tβ4 are known in the art. For example, a polypeptide comprising the amino acid sequence MSDKPDMAEIEKFDKSKLKKTETQEKN-PLPSKETIEQEKQAGES (SEQ ID NO:30; human Tβ4); or a polypeptide comprising an amino acid sequence having an amino acid sequence that is at least 95%, at least 98%, or at least 99%, identical to human Tβ4, can be used.

Histone deacetylases (HDAC) are a class of enzymes that remove acetyl groups from an [epsilon]-N-acetyl lysine amino acid on a histone. Exemplary HDACs include those Class I HDAC: HDAC1, HDAC2, HDAC3, HDAC8; and Class II HDACs: HDAC4, HDAC5, HDAC6, HDAC7A, HDAC9, HDAC10. Type I mammalian HDACs include: HDAC1, HDAC2, HDAC3, HDAC8, and HDAC11. Type II mammalian HDACs include: HDAC4, HDAC5, HDAC6, HDAC7, HDAC9, and HDAC1. In some embodiments, an HDAC inhibitor selectively inhibits a Class I or a Class II HDAC.

Suitable concentrations of an HDAC inhibitor range from about 0.001 nM to about 10 mM, depending on the particular HDAC inhibitor to be used. The HDAC concentration can range from 0.01 nM to 1000 nM.

Suitable HDAC inhibitors include any agent that inhibits HDAC enzymatic activity in deacetylation of histone. Suitable HDAC inhibitors include, but are not limited to, carboxylate HDAC inhibitors; hydroxamic acid HDAC inhibitors; peptide (e.g., cyclic tetrapeptide) HDAC inhibitors; benzamide HDAC inhibitors; electrophilic ketone HDAC inhibitors; hybrid polar HDAC inhibitors; and short chain fatty acid HDAC inhibitors.

Suitable HDAC inhibitors include trichostatin A and its analogs, for example: trichostatin A (TSA); and trichostatin C (Koghe et al. (1998) Biochem. Pharmacol, 56:1359-1364).

Suitable peptide HDAC inhibitors include, for example: oxamflatin[(2E)-5-[3-[(phenylsulfonyl)aminophenyl]-pent-2-ene-4-inohydroxamic acid (Kim et al., (1999), Oncogene, 18:2461-2470); Trapoxin A (cyclo-(L-phenylalanyl-L-phenylalanyl-D-pipecolinyl-L-2-amino-8-oxo-9,10-epoxy-decanoyl) (Kijima et al., (1993), J. Biol. Chem. 268:22429-22435); FR901228, depsipeptide ((1S,4S,7Z,10S,16E,21R)-7-ethylidene-4,21-diisopropyl-2-oxa-12,13-dithia-5,8,20,23-tetrazabicyclo[8.7.6]tricos-16-ene-3,6,9,19,22-pentone) (Nakajima et al., (1998). Ex. Cell Res., 241:126-133); apicidin, cyclic tetrapeptide[cyclo-(N—O-methyl-L-tryptophanyl-L-isoleucinyl-D-pipecolinyl-L-2-amino-8-oxodecanoyl)] (Darkin-Rattray et al., (1996), Proc. Natl. Acad. Sci. U.S.A., 93:13143-13147; apicidin Ia, apicidin Ib, apicidin Ic, apicidin IIa, and apicidin IIb (WO 97/11366); HC-toxin, cyclic tetrapeptide (Bosch et al. (1995), Plant Cell, 7:1941-1950); and chlamydocin (Bosch et al., supra).

Suitable HDAC inhibitors include hybrid polar compounds (HPC) based on hydroxamic acid, for example: salicyl hydroxamic acid (SBHA) (Andrews et al., (2000), International J. Parasitology, 30:761-8); suberoylanilide hydroxamic acid (SAHA) (Richon et al., (1998), Proc. Natl. Acad. Sci. U.S.A., 95: 3003-7); azelaic bishydroxamic acid (ABHA) (Andrews et al., supra); azelaic-1-hydroxamate-9-anilide (AAHA) (Qiu et al., (2000), Mol. Biol. Cell, 11:2069-83); M-carboxy cinnamic acid bishydroxamide (CBHA) (Richon et al., supra); 6-(3-chlorophenylureido) carpoic hydroxamic acid, 3-Cl-UCHA) (Richon et al., supra); MW2796 (Andrews et al., supra); MW2996 (Andrews et al., supra); the hydroxamic acid derivative NVP-LAQ-824 (Catley et al. (2003) Blood 102:2615; and Atadja et al. (2004) Cancer Res. 64:689); and CBHA (m-carboxycinnaminic acid bishydroxamic acid).

Suitable HDAC inhibitors include short chain fatty acid (SCFA) compounds, for example: sodium butyrate (Cousens et al., (1979), J. Biol. Chem., 254:1716-23); isovalerate (McBain et al., (1997), Biochem. Pharm., 53:1357-68); valproic acid; valerate (McBain et al., supra); 4-phenyl butyric acid (4-PBA) (Lea and Tulsyan, (1995), Anticancer Research, 15:879-3); phenyl butyric acid (PB) (Wang et al., (1999), Cancer Research 59: 2766-99); propinate (McBain et al., supra); butylamide (Lea and Tulsyan, supra); isobutylamide (Lea and Tulsyan, supra); phenyl acetate (Lea and Tulsyan, supra); 3-bromopropionate (Lea and Tulsyan, supra); tributyrin (Guan et al., (2000), Cancer Research, 60:749-55); arginine butyrate; isobutyl amide; and valproate.

Suitable HDAC inhibitors include benzamide derivatives, for example: MS-275 [N-(2-aminophenyl)-4-[N-(pyridine-3-yl-methoxycarbonyl)aminomethyl]benzamide] (Saito et al., (1999), Proc. Natl. Acad. Sci. U.S.A., 96:4592-7); and a 3'-amino derivative of MS-275 (Saito et al., supra); and CI-994.

Additional suitable HDAC inhibitors include: BML-210 (N-(2-aminophenyl)-N'-phenyl-octanediamide); Depudecin (e.g., (−)-Depudecin); Nullscript (4-(1,3-Dioxo-1H,3H-benzo[de]isoquinolin-2-yl)-N-hydroxybutanamide); Scriptaid; Suramin Sodium; pivaloyloxymethyl butyrate (Pivanex, AN-9), Trapoxin B; CI-994 (i.e., N-acetyl dinaline); MGCD0103 (N-(2-Aminophenyl)-4-[[(4-pyridin-3-ylpyrimidin-2-yl)amino]methyl]benzamide); JNJ16241199 (R-306465; see, e.g., Arts et al. (2007) Br. J. Cancer 97:1344); Tubacin; A-161906; proxamide; oxamflatin; 3-Cl-UCHA (6-(3-chlorophenylureido)caproic hydroxamic acid); and AOE (2-amino-8-oxo-9,10-epoxydecanoic acid).

Suitable DNA methylation inhibitors are inhibitors of DNA methyltransferase, and include, but are not limited to, 5-deoxy-azacytidine (DAC); 5-azacytidine (5-aza-CR) (Vidaza); 5-aza-2'-deoxycytidine (5-aza-CdR; decitabine); 1-[beta]-D-arabinofuranosyl-5-azacytosine; dihydro-5-azacytidine; zebularine ((1-(β-D-ribofuranosyl)-1,2-dihydropyrimidin-2-one); Sinefungin (e.g., InSolution™ Sinefungin), and 5-fluoro-2'-deoxycyticine (FdCyd). Examples of suitable non-nucleoside DNA methyltransferase inhibitors (e.g., other than procaine) include: (−)-epigallocatechin-3-gallate (EGCG); hydralazine; procainamide; psammaplin A (N,N"-(dithiodi-2,1-ethanediyl)bis[3-bromo-4-hydroxy-a-(hydroxyimino)-benzenepropanamide); and RG 108 (2-(1,3-Dioxo-1,3-dihydro-2H-isoindol-2-yl)-3-(1H-indol-3-yl) propionic acid).

Suitable histone methyltransferase (HMT) inhibitors include, but are not limited to, SC-202651 (2-(Hexahydro-4-methyl-1H-1,4-diazepin-1-yl)-6,7-dimethoxy-N-(1-(phenylmethyl)-4-piperidinyl)-4-quinazolinamine); chaetocin (Grainer et al. (2005) Nature Chem. Biol. 1:143); BIX-01294 (2-(Hexahydro-4-methyl-1H-1,4-diazepin-1-yl)-6,7-dimethoxy-N-[1-(phenylmethyl)-4-piperidinyl]-4-quinazolinamine trihydrochloride); 3-deazaneplanocin (Glazer et al. (1986) BBRC 135:688); and the like.

Genetically Modified Host Cells

The present disclosure provides genetically modified host cells, including isolated genetically modified host cells, where a subject genetically modified host cell comprises (has been genetically modified with) one or more exogenous nucleic acids comprising nucleotide sequences encoding reprogramming factor polypeptides (e.g., Gata4, Mef2c, Tbx5, Mesp1, Esrrg reprogramming factors, or a subset comprising Gata4, Mef2c, Tbx5, Mesp1, Esrrg, where sets of reprogramming factors include, e.g., 1) Gata4, Mef2c, Tbx5, Mesp1, Esrrg, Nkx2.5, Srf, Zfpm2, Myocd, Baf60c, Hand2, Isl1, Nfatc1, Smyd1, and TGFβ1 polypeptides; 2) Gata4, Mef2c, Tbx5, Mesp1, Esrrg, Nkx2.5, Srf, Zfpm2, and Myocd polypeptides; 3) Gata4, Mef2c, Tbx5, Mesp1, and Esrrg polypeptides; and 4) Gata4, Mef2c, Tbx5, Mesp1, and Esrrg polypeptides; and one or more of, Nkx2.5, Srf, Zfpm2, Myocd, Baf60c, Hand2, Isl1, Nfatc1, Smyd1, and TGFβ1 polypeptides.

In some embodiments, a subject genetically modified host cell is in vitro. In some embodiments, a subject genetically modified host cell is a human cell or is derived from a human cell. The present disclosure further provides progeny of a subject genetically modified host cell, where the progeny can comprise the same exogenous nucleic acid as the subject genetically modified host cell from which it was derived. The present disclosure further provides a composition comprising a subject genetically modified host cell.

The present disclosure provides genetically modified host cells, including isolated genetically modified host cells, where a subject genetically modified host cell comprises (has been genetically modified with) one or more exogenous nucleic acids comprising nucleotide sequences encoding Gata4, Mef2c, Tbx5, Mesp1, Esrrg reprogramming factors, or a subset comprising Gata4, Mef2c, Tbx5, Mesp1, Esrrg. In some embodiments, a subject genetically modified host cell is in vitro. In some embodiments, a subject genetically modified host cell is a human cell or is derived from a human cell. The present disclosure further provides progeny of a subject genetically modified host cell, where the progeny can comprise the same exogenous nucleic acid as the subject genetically modified host cell from which it was derived.

The present disclosure further provides a composition comprising a subject genetically modified host cell.

Genetically Modified Post-Natal Fibroblasts

In some embodiments, a subject genetically modified host cell is a genetically modified post-natal fibroblast. Thus, the present disclosure provides a genetically modified post-natal fibroblast that comprises (has been genetically modified with) one or more exogenous nucleic acids comprising nucleotide sequences encoding Gata4, Mef2c, Tbx5, Mesp1, and Esrrg polypeptides, or a subset of reprogramming factors comprising Gata4, Mef2c, Tbx5, Mesp1, and Esrrg polypeptides. In some embodiments, a subject genetically modified post-natal fibroblast is in vitro. In some embodiments, a subject genetically modified post-natal fibroblast is a human cell or is derived from a human cell. The present disclosure further provides progeny of a subject genetically modified post-natal fibroblast, where the progeny can comprise the same exogenous nucleic acid as the subject genetically modified post-natal fibroblast from which it was derived. The present disclosure further provides a composition comprising a subject genetically modified post-natal fibroblast.

Genetically Modified Induced Cardiomyocytes

The present disclosure further provides cardiomyocytes ("induced cardiomyocytes") derived from a subject genetically modified host cell. Because a subject induced cardiomyocyte is derived from a subject genetically modified post-natal fibroblast, a subject induced cardiomyocyte is also genetically modified. Thus, the present disclosure provides a genetically modified cardiomyocyte that comprises one or more exogenous nucleic acids comprising nucleotide sequences encoding Gata4, Mef2c, Tbx5, Mesp1, and Esrrg polypeptides, or a subset of reprogramming factors comprising Gata4, Mef2c, Tbx5, Mesp1, and Esrrg polypeptides. In some embodiments, a subject genetically modified cardiomyocyte is in vitro. In some embodiments, a subject genetically modified cardiomyocyte is a human cell or is derived from a human cell. The present disclosure further provides progeny of a subject genetically modified cardiomyocyte, where the progeny can comprise the same exogenous nucleic acid as the subject genetically modified cardiomyocyte from which it was derived. The present disclosure further provides a composition comprising a subject genetically modified cardiomyocyte.

Compositions

The present disclosure provides a composition comprising a subject genetically modified host cell (e.g., a subject genetically modified post-natal fibroblast; progeny of a subject genetically modified post-natal fibroblast; a subject induced cardiomyocyte; progeny of a subject induced cardiomyocyte). A subject composition comprises a subject genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

In some embodiments, a subject composition comprises a subject genetically modified host cell and a matrix (a "subject genetically modified cell/matrix composition"), where a subject genetically modified host cell is associated with the matrix. The term "matrix" refers to any suitable carrier material to which the genetically modified cells are able to attach themselves or adhere in order to form a cell composite. In some embodiments, the matrix or carrier material is present already in a three-dimensional form desired for later application. For example, bovine pericardial tissue is used as matrix which is crosslinked with collagen, decellularized and photofixed.

For example, a matrix (also referred to as a "biocompatible substrate") is a material that is suitable for implantation into a subject. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. The biocompatible substrate can provide the supportive framework that allows cells to attach to it and grow on it.

Suitable matrix components include, e.g., collagen; gelatin; fibrin; fibrinogen; laminin; a glycosaminoglycan; elastin; hyaluronic acid; a proteoglycan; a glycan; poly(lactic acid); poly(vinyl alcohol); poly(vinyl pyrrolidone); poly(ethylene oxide); cellulose; a cellulose derivative; starch; a starch derivative; poly(caprolactone); poly(hydroxy butyric acid); mucin; and the like. In some embodiments, the matrix comprises one or more of collagen, gelatin, fibrin, fibrinogen, laminin, and elastin; and can further comprise a non-proteinaceous polymer, e.g., can further comprise one or more of poly(lactic acid), poly(vinyl alcohol), poly(vinyl pyrrolidone), poly(ethylene oxide), poly(caprolactone), poly(hydroxy butyric acid), cellulose, a cellulose derivative, starch, and a starch derivative. In some embodiments, the matrix comprises one or more of collagen, gelatin, fibrin, fibrinogen, laminin, and elastin; and can further comprise hyaluronic acid, a proteoglycan, a glycosaminoglycan, or a glycan. Where the matrix comprises collagen, the collagen can comprise type I collagen, type II collagen, type III collagen, type V collagen, type XI collagen, and combinations thereof.

The matrix can be a hydrogel. A suitable hydrogel is a polymer of two or more monomers, e.g., a homopolymer or a heteropolymer comprising multiple monomers. Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers. Exemplary hydrogels include, but are not limited to, a copolymer of poly(ethylene oxide) (PEO) and poly(propylene oxide) (PPO); Pluronic™ F-127 (a difunctional block copolymer of PEO and PPO of the nominal formula $EO_{100}$-$PO_{65}$-$EO_{100}$, where EO is ethylene oxide and PO is propylene oxide); poloxamer 407 (a tri-block copolymer consisting of a central block of poly(propylene glycol) flanked by two hydrophilic blocks of poly(ethylene glycol)); a poly(ethylene oxide)-poly(propylene oxide)-poly(ethylene oxide) co-polymer with a nominal molecular weight of 12,500 Daltons and a PEO:PPO ratio of 2:1); a poly(N-isopropylacrylamide)-base hydrogel (a PNIPAAm-based hydrogel); a PNIPAAm-acrylic acid co-polymer (PNIPAAm-co-AAc); poly(2-hydroxyethyl methacrylate); poly(vinyl pyrrolidone); and the like.

A subject genetically modified cell/matrix composition can further comprise one or more additional components, where suitable additional components include, e.g., a growth factor; an antioxidant; a nutritional transporter (e.g., transferrin); a polyamine (e.g., glutathione, spermidine, etc.); and the like.

The cell density in a subject genetically modified cell/matrix composition can range from about $10^2$ cells/mm$^3$ to about $10^9$ cells/mm$^3$, e.g., from about $10^2$ cells/mm$^3$ to about $10^4$ cells/mm$^3$, from about $10^4$ cells/mm$^3$ to about $10^6$ cells/mm$^3$, from about $10^6$ cells/mm$^3$ to about $10^7$ cells/mm$^3$, from about $10^7$ cells/mm$^3$ to about $10^8$ cells/mm$^3$, or from about $10^8$ cells/mm$^3$ to about $10^9$ cells/mm$^3$.

The matrix can take any of a variety of forms, or can be relatively amorphous. For example, the matrix can be in the form of a sheet, a cylinder, a sphere, etc.

Implantable Devices

The present disclosure provides an implantable device (such as an intravascular stent, a scaffold, a graft (e.g., an aortic graft), an artificial heart valve, a coronary shunt, a pacemaker electrode, an endocardial lead, etc.) that comprises a reprogramming composition comprising Gata4, Mef2c, Tbx5, Mesp1, and Esrrg polypeptides, or a subset of reprogramming factors comprising Gata4, Mef2c, Tbx5, Mesp1, and Esrrg polypeptides. The present disclosure further provides an implantable device that comprises a reprogramming composition comprising one or more nucleic acids comprising nucleotide sequences encoding Gata4, Mef2c, Tbx5, Mesp1, and Esrrg polypeptides, or a subset of reprogramming factors comprising Gata4, Mef2c, Tbx5, Mesp1, and Esrrg polypeptides. The reprogramming composition (comprising Gata4, Mef2c, Tbx5, Mesp1, and Esrrg polypeptides, or comprising one or more nucleic acids comprising nucleotide sequences encoding Gata4, Mef2c, Tbx5, Mesp1, and Esrrg polypeptides) can be coated onto a surface of the implantable device, or can be contained within a reservoir in the implantable device. Where the reprogramming composition is contained within a reservoir in the implantable device, the reservoir is structured so as to allow the reprogramming composition to elute from the device.

The present disclosure provides an implantable device (such as an intravascular stent, a scaffold, a graft (e.g., an aortic graft), an artificial heart valve, a coronary shunt, a pacemaker electrode, an endocardial lead, etc.) that comprises a reprogramming composition comprising Gata4, Mef2c, Tbx5, Mesp1, and Esrrg polypeptides, or a subset of reprogramming factors comprising Gata4, Mef2c, Tbx5, Mesp1, and Esrrg polypeptides. The present disclosure further provides an implantable device that comprises a reprogramming composition comprising one or more nucleic acids comprising nucleotide sequences encoding Gata4, Mef2c, Tbx5, Mesp1, and Esrrg polypeptides, or a subset of reprogramming factors comprising Gata4, Mef2c, Tbx5, Mesp1, and Esrrg polypeptides. The reprogramming composition (comprising Gata4, Mef2c, Tbx5, Mesp1, and Esrrg polypeptides, or comprising one or more nucleic acids comprising nucleotide sequences encoding Gata4, Mef2c, Tbx5, Mesp1, and Esrrg polypeptides) can be coated onto a surface of the implantable device, or can be contained within a reservoir in the implantable device. Where the reprogramming composition is contained within a reservoir in the implantable device, the reservoir is structured so as to allow the reprogramming composition to elute from the device.

When the implantable device is at a site in an individual, the nucleic acids or the polypeptides in the reprogramming composition leave the implantable device, and the polypeptides or the nucleic acids enter into a fibroblast at or near the site of the implantable device. Thus, a subject implantable device, when implanted in an individual, can provide for introduction of reprogramming factors, or nucleic acids encoding same, into a fibroblast at or near the site of implant, and can thereby provide for reprogramming of the fibroblast into a cardiomyocyte. For example, where a subject implantable device is a stent, the stent can be implanted into a coronary artery, where the reprogramming factors, or nucleic acids encoding same, elute from the stent, enter fibroblasts in the coronary vascular bed, and reprogram the fibroblasts into cardiomyocytes.

The present disclosure provides a stent comprising a reprogramming composition. Intravascular stents include, e.g., self-expandable stents, balloon-expandable stents, and stent-grafts.

In some instances, a subject implantable device comprises: a reprogramming composition incorporated within a first polymeric material (a first layer) that is affixed to the surface of an implantable device (e.g., a stent); and a second polymeric material (e.g., a barrier layer) is affixed to the first polymeric material, where the second polymeric material controls the elution rate of the polypeptides or the nucleic acids present in the reprogramming composition. As an example, the first polymeric material can comprise a fluoropolymer; and the second polymeric material can comprise an acrylic.

In some instances, a subject implantable device comprises: a reprogramming composition incorporated into a polymeric layer (a first layer) that is coated onto a surface of an implantable device (e.g., a stent); and a barrier layer over at least a portion of the polymeric layer to reduce the rate of release of the polypeptides or nucleic acids contained within the reprogramming composition from the implantable device. The polymeric layer can comprise poly(methylmethacrylate) or poly(butylmethacrylate), and can further include poly(ethylene co-vinyl acetate). The barrier can comprise a polymer or an inorganic material.

Suitable polymer materials for first layer include, but are not limited to, polyurethanes, polyesterurethanes, silicone, fluoropolymers, ethylene vinyl acetate, polyethylene, polypropylene, polycarbonates, trimethylenecarbonate, polyphosphazene, polyhydroxybutyrate, polyhydroxyvalerate, polydioxanone, polyiminocarbonates, polyorthoesters, ethylene vinyl alcohol copolymer, L-polylactide, D,L-polylactide, polyglycolide, polycaprolactone, copolymers of lactide and glycolide, polymethylmethacrylate, poly(n-butyl)methacrylate, polyacrylates, polymethacrylates, elastomers, and mixtures thereof.

Representative elastomers include, but are not limited to, a thermoplastic elastomer material, polyether-amide thermoplastic elastomer, fluoroelastomers, fluorosilicone elastomer, sytrene-butadiene rubber, butadiene-styrene rubber, polyisoprene, neoprene (polychloroprene), ethylene-propylene elastomer, chloro-sulfonated polyethylene elastomer, butyl rubber, polysulfide elastomer, polyacrylate elastomer, nitrile, rubber, polyester, styrene, ethylene, propylene, butadiene and isoprene, polyester thermoplastic elastomer, and mixtures thereof.

The barrier layer is biocompatible (i.e., its presence does not elicit an adverse response from the body). The barrier layer can have a thickness ranging from about 50 angstroms to about 20,000 angstroms. The barrier can comprise mostly inorganic material. However, some organic compounds (e.g., polyacrylonitrile, polyvinylidene chloride, nylon 6-6, perfluoropolymers, polyethylene terephthalate, polyethylene 2,6-napthalene dicarboxylate, and polycarbonate) may be incorporated in the barrier. Suitable inorganic materials for use within the barrier include, but are not limited to, inorganic elements, such as pure metals including aluminum, chromium, gold, hafnium, iridium, niobium, palladium, platinum, tantalum, titanium, tungsten, zirconium, and alloys of these metals, and inorganic compounds, such as inorganic silicides, oxides, nitrides, and carbides. Generally, the solubility of the drug in the material of the barrier is significantly less than the solubility of the drug in the polymer carrier. Also, generally, the diffusivity of the drug in the material of the barrier is significantly lower than the diffusivity of the drug in the polymer carrier.

The barrier may or may not be biodegradable (i.e., capable of being broken down into harmless compounds by the action of the body). While non-biodegradable barrier materials may be used, some biodegradable materials may be used as barriers. For example, calcium phosphates such as hydroxyapatite, carbonated hydroxyapatite, tricalcium phosphate, beta-tricalcium phosphate, octacalcium phosphate, amorphous calcium phosphate, and calcium orthophosphate may be used. Certain calcium salts such as calcium phosphate (plaster of paris) may also be used. The biodegradability of the barrier may act as an additional mechanism for controlling drug release from the underlying first layer.

Methods of affixing the first layer onto the surface of an implantable device, and methods of affixing a barrier layer on the first layer, are known in the art. See, e.g., U.S. Pat. Nos. 7,695,731 and 7,691,401.

As noted above, in some embodiments, a subject implantable device comprises a reservoir comprising a reprogramming composition. For example, in some embodiments, a subject implantable device has at least one surface for contacting a bodily tissue, organ or fluid, where the implantable device comprises: a substrate having a contacting surface; and a drug-eluting coating on at least a portion of the contacting surface, where the coating is comprised of a polymer having zeolites dispersed through the polymer, and where a porous structure of the zeolites includes reservoirs containing a release agent and a reprogramming composition. The release agent prevents the therapeutic material from exiting the reservoir until a triggering condition is met. A triggering condition can be contact of the release agent with a bodily fluid; a change in pH proximate to the release agent; and the like.

Biodegradable polymers, suitable for use alone or in combination, include, but are not limited to: poly(α-hydroxy acids), such as, polycapro lactone (PCL), poly(lactide-co-glycolide) (PLGA), polylactide (PLA), and polyglycolide (PGA), and combinations and blends thereof above at different ratios to fine-tune release rates, PLGA-PEG (polyethylene glycol), PLA-PEG, PLA-PEG-PLA, polyanhydrides, trimethylene carbonates, polyorthoesters, polyaspirins, polyphosphagenes, and tyrozine polycarbonates; natural and synthetic hydrogel materials, e.g., collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, and PLGA-PEO-PLGA. Polymer matrices according to embodiments of the present invention may include any of the following biostable polymers, alone or in combination: polyurethanes, polymethylmethacrylates copolymers, polyvinyl acetate (PVA), polyamides, and copolymers of polyurethane and silicone.

Reprogramming Composition

The present disclosure provides reprogramming compositions.

In some embodiments, a subject reprogramming composition comprises either: 1) a mixture Gata4, Mef2c, Tbx5, Mesp1, and Esrrg polypeptides, or a subset of reprogramming factors comprising Gata4, Mef2c, Tbx5, Mesp1, and Esrrg polypeptides; or 2) one or more nucleic acids comprising nucleotide sequences encoding Gata4, Mef2c, Tbx5, Mesp1, and Esrrg polypeptides, or a subset of reprogramming factors comprising Gata4, Mef2c, Tbx5, Mesp1, and Esrrg polypeptides. The reprogramming composition can comprise, in addition to the polypeptides or the nucleic acids, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

In some embodiments, a subject reprogramming composition comprises either: 1) a mixture of Gata4, Mef2c, and Tbx5 polypeptides, or a subset of reprogramming factors comprising Gata4, Mef2c, Tbx5, Mesp1, and Esrrg polypeptides; or 2) one or more nucleic acids comprising nucleotide sequences encoding Gata4, Mef2c, and Tbx5 polypeptides, or a subset of reprogramming factors comprising Gata4, Mef2c, Tbx5, Mesp1, and Esrrg polypeptides. The reprogramming composition can comprise, in addition to the polypeptides or the nucleic acids, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

A subject reprogramming composition can be included in a subject implantable device, as described above. A subject reprogramming composition can be administered directly into an individual. A subject reprogramming composition is useful for reprogramming a post-natal fibroblast into a cardiomyocyte, which reprogramming can be carried out in vitro or in vivo. Reprogramming a post-natal fibroblast into a cardiomyocyte can be used to treat various cardiac disorders, as described below.

A subject reprogramming composition can include a pharmaceutically acceptable excipient. Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject reprogramming composition is formulated as a controlled release (also referred to herein as a "sustained release") formulation. Controlled release compositions suitable for use include solid compositions, semi-solid (e.g., gel) compositions, and fluid (e.g., liquid) compositions. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in activity of a polypeptide or a nucleic acid comprised in sustained-release preparations may be prevented by using appropriate additives, by controlling moisture content and by developing specific polymer matrix compositions.

A subject reprogramming composition can further comprise one or more therapeutic agents, e.g., a therapeutic agent for treating a heart disease or condition. Therapeutic agents that can be included in a subject reprogramming composition can include, e.g., digitalis, a statin, an anti-platelet agent, an anti-coagulant, a calcium channel blocker, an angiotensin-converting enzyme inhibitor, a vasodilator, an angiotensin II receptor blocker, a beta blocker, and the like.

Utility

A subject method of reprogramming a post-natal fibroblast is useful for generating a population of induced cardiomyocytes, which induced cardiomyocytes can be used in analytical assays, for generating artificial heart tissue, and in treatment methods.

Analytical Assays

A subject method can be used to generate cardiomyocytes for analytical assays. Analytical assays include, e.g., introduction of the cardiomyocytes into a non-human animal model of a disease (e.g., a cardiac disease) to determine efficacy of the cardiomyocytes in the treatment of the disease; use of the cardiomyocytes in screening methods to identify candidate agents suitable for use in treating cardiac disorders; and the like. In some cases, a cardiomyocyte generated using a subject method can be used to assess the toxicity of a test agent or for drug optimization.

Animal Models

In some embodiments, a cardiomyocyte generated using a subject method can be introduced into a non-human animal model of a cardiac disorder, and the effect of the cardiomyocyte on ameliorating the disorder can be tested in the non-human animal model (e.g., a rodent model such as a rat model, a guinea pig model, a mouse model, etc.; a non-human primate model; a lagomorph model; and the like). For example, the effect of a cardiomyocyte generated using a subject method on a cardiac disorder in a non-human animal model of the disorder can be tested by introducing the cardiomyocyte into, near, or around diseased cardiac tissue in the non-human animal model; and the effect, if any, of the introduced cardiomyocyte on cardiac function can be assessed. Methods of assessing cardiac function are well known in the art; and any such method can be used.

Drug/Agent Screening or Identification

Cardiomyocytes generated using a subject method may be used to screen for drugs or test agents (e.g., solvents, small molecule drugs, peptides, oligonucleotides) or environmental conditions (e.g., culture conditions or manipulation) that affect the characteristics of such cells and/or their various progeny. See, e.g., U.S. Pat. No. 7,425,448. Drugs or test agents may be individual small molecules of choice (e.g., a lead compound from a previous drug screen) or in some cases, the drugs or test agents to be screened come from a combinatorial library, e.g., a collection of diverse chemical compounds generated by either chemical synthesis or biological synthesis by combining a number of chemical "building blocks." For example, a linear combinatorial chemical library such as a polypeptide library is formed by combining a set of amino acids in every possible way for a given compound length (e.g., the number of amino acids in a polypeptide compound). Millions of test agents (e.g., chemical compounds) can be synthesized through such combinatorial mixing of chemical building blocks. Indeed, theoretically, the systematic, combinatorial mixing of 100 interchangeable chemical building blocks results in the synthesis of 100 million tetrameric compounds or 10 billion pentameric compounds. See, e.g., Gallop et al. (1994), J. Med. Chem. 37(9), 1233. Preparation and screening of combinatorial chemical libraries are well known in the art. Combinatorial chemical libraries include, but are not limited to: diversomers such as hydantoins, benzodiazepines, and dipeptides, as described in, e.g., Hobbs et al. (1993), Proc. Natl. Acad. Sci. U.S.A. 90, 6909; analogous organic syntheses of small compound libraries, as described in Chen et al. (1994), J. Amer. Chem. Soc., 116: 2661; Oligocarbamates, as described in Cho, et al. (1993), Science 261, 1303; peptidyl phosphonates, as described in Campbell et al. (1994), J. Org. Chem., 59: 658; and small organic molecule libraries containing, e.g., thiazolidinones and metathiazanones (U.S. Pat. No. 5,549,974), pyrrolidines (U.S. Pat. Nos. 5,525,735 and 5,519,134), benzodiazepines (U.S. Pat. No. 5,288,514).

Numerous combinatorial libraries are commercially available from, e.g., ComGenex (Princeton, N.J.); Asinex (Moscow, Russia); Tripos, Inc. (St. Louis, Mo.); ChemStar, Ltd. (Moscow, Russia); 3D Pharmaceuticals (Exton, Pa.); and Martek Biosciences (Columbia, Md.).

In some embodiments, a cardiomyocyte generated using a subject method is contacted with a test agent, and the effect, if any, of the test agent on a biological activity of the cardiomyocyte is assessed, where a test agent that has an effect on a biological activity of the cardiomyocyte is a candidate agent for treating a cardiac disorder or condition. For example, a test agent of interest is one that increases a biological activity of the cardiomyocyte by at least about 5%, at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the biological activity in the absence of the test agent. A test agent of interest is a candidate agent for treating a cardiac disorder or condition. In some embodiments, the contacting is carried out in vitro. In other embodiments, the contacting is carried out in vivo, e.g, in a non-human animal.

A "biological activity" includes, e.g., one or more of marker expression (e.g., cardiomyocyte-specific marker expression), receptor binding, ion channel activity, contractile activity, and electrophysiological activity.

For example, in some embodiments, the effect, if any, of the test agent on expression of a cardiomyocyte marker is assessed. Cardiomyocyte markers include, e.g., cardiac troponin I (cTnI), cardiac troponin T (cTnT), sarcomeric myosin heavy chain (MHC), GATA-4, Nkx2.5, N-cadherin, β-adrenoceptor (β1-AR), a member of the MEF-2 family of transcription factors, creatine kinase MB (CK-MB), myoglobin, and atrial natriuretic factor (ANF).

As another example, the effect, if any, of the test agent on electrophysiology of the cardiomyocyte is assessed. Electrophysiology can be studied by patch clamp analysis for cardiomyocyte-like action potentials. See Igelmund et al., Pflugers Arch. 437:669, 1999; Wobus et al., Ann. N.Y. Acad. Sci. 27:752, 1995; and Doevendans et al., J. Mol. Cell. Cardiol. 32:839, 2000.

As another example, in some embodiments, the effect, if any, of the test agent on ligand-gated ion channel activity is assessed. As another example, in some embodiments, the effect, if any, of the test agent on voltage-gated ion channel activity is assessed. The effect of a test agent on ion channel activity is readily assessed using standard assays, e.g., by measuring the level of an intracellular ion (e.g., $Na^+$, $Ca^{2+}$, $K^+$, etc.). A change in the intracellular concentration of an ion can be detected using an indicator appropriate to the ion whose influx is controlled by the channel. For example, where the ion channel is a potassium ion channel, a potassium-detecting dye is used; where the ion channel is a calcium ion channel, a calcium-detecting dye is used; etc.

Suitable intracellular $K^+$ ion-detecting dyes include, but are not limited to, $K^+$-binding benzofuran isophthalate and the like. Suitable intracellular $Ca^{2+}$ ion-detecting dyes are listed above.

The effect of a test agent in the assays described herein can be assessed using any standard assay to observe phenotype or activity of cardiomyocytes generated using a subject method, such as marker expression, receptor binding, contractile activity, or electrophysiology—either in in vitro cell culture or in vivo. See, e.g., U.S. Pat. No. 7,425, 448. For example, pharmaceutical candidates are tested for their effect on contractile activity—such as whether they increase or decrease the extent or frequency of contraction, using any methods known in the art. Where an effect is observed, the concentration of the compound can be titrated to determine the median effective dose (ED50).

Test Agent/Drug Toxicity

A cardiomyocyte generated using a subject method can be used to assess the toxicity of a test agent, or drug, e.g., a test agent or drug designed to have a pharmacological effect on cardiomyocytes, e.g., a test agent or drug designed to have effects on cells other than cardiomyocytes but potentially affecting cardiomyocytes as an unintended consequence. In some embodiments, the disclosure provides methods for evaluating the toxic effects of a drug, test agent, or other factor, in a human or non-human (e.g., murine; lagomorph; non-human primate) subject, comprising contacting one or more cardiomyocytes generated using a subject method with a dose of a drug, test agent, or other factor and assaying the contacted cardiomyocytes for markers of toxicity or cardiotoxicity.

Any method known in the art may be used to evaluate the toxicity or adverse effects of a test agent or drug on cardiomyocytes generated using a subject method. Cytotoxicity or cardiotoxicity can be determined, e.g., by the effect on cell viability, survival, morphology, and the expression of certain markers and receptors. For example, biochemical markers of myocardial cell necrosis (e.g., cardiac troponin T and I (cTnT, cTnI)) may be used to assess drug-induced toxicity or adverse reactions in cardiomyocytes generated using a subject method, where the presence of such markers in extracellular fluid (e.g., cell culture medium) can indicate necrosis. See, e.g., Gaze and Collinson (2005) Expert Opin Drug Metab Toxicol 1(4):715-725. In another example, lactate dehydrogenase is used to assess drug-induced toxicity or adverse reactions in cardiomyocytes generated using a subject method. See, e.g., Inoue et al. (2007) AATEX 14, Special Issue: 457-462. In another example, the effects of a drug on chromosomal DNA can be determined by measuring DNA synthesis or repair and used to assess drug-induced toxicity or adverse reactions in cardiomyocytes generated using a subject method. In still another example, the rate, degree, and/or timing of $[^3H]$-thymidine or BrdU incorporation may be evaluated to assess drug-induced toxicity or adverse reactions in cardiomyocytes generated using a subject method. In yet another example, evaluating the rate or nature of sister chromatid exchange, determined by metaphase spread, can be used to assess drug-induced toxicity or adverse reactions in cardiomyocytes generated using a subject method. See, e.g., A. Vickers (pp 375-410 in In vitro Methods in Pharmaceutical Research, Academic Press, 1997). In yet another example, assays to measure electrophysiology or activity of ion-gated channels (e.g., Calcium-gated channels) can be used to assess drug-induced toxicity or adverse reactions in cardiomyocytes generated using a subject method. In still another example, contractile activity (e.g., frequency of contraction) can be used to assess drug-induced toxicity or adverse reactions in cardiomyocytes generated using a subject method.

In some embodiments, the present disclosure provides methods for reducing the risk of drug toxicity in a human or murine subject, comprising contacting one or more cardiomyocytes generated using a subject method with a dose of a drug, test agent, or pharmacological agent, assaying the contacted one or more differentiated cells for toxicity, and prescribing or administering the pharmacological agent to the subject if the assay is negative for toxicity in the contacted cells. In some embodiments, the present disclosure provides methods for reducing the risk of drug toxicity in a human or murine subject, comprising contacting one or more cardiomyocytes generated using a subject method with a dose of a pharmacological agent, assaying the contacted one or more differentiated cells for toxicity, and prescribing or administering the pharmacological agent to the subject if the assay indicates a low risk or no risk for toxicity in the contacted cells.

Treatment Methods Using Cells

A subject modified or genetically modified fibroblast can be used to treat an individual in need of such treatment. Similarly, a subject induced cardiomyocyte can be used to treat an individual in need of such treatment. A subject modified or genetically modified fibroblast, or a subject induced cardiomyocyte, can be introduced into a recipient individual (an individual in need of treatment), where introduction into the recipient individual of a subject modified or genetically modified fibroblast, or a subject induced cardiomyocyte, treats a condition or disorder in the individual. Thus, in some embodiments, a subject treatment method involves administering to an individual in need thereof a population of subject modified or genetically modified fibroblasts. In some embodiments, a subject treatment method involves administering to an individual in need thereof a population of subject induced cardiomyocytes.

In some embodiments, the present disclosure provides a method for performing cell transplantation in a recipient individual in need thereof, the method generally involving: (i) generating an induced cardiomyocyte from a fibroblast obtained from a donor individual, wherein the donor individual is immunocompatible with the recipient individual; and (ii) transplanting one or more of the induced cardiomyocytes into the recipient individual. In some embodiments, the recipient individual and the donor individual are the same individual. In some embodiments, the recipient individual and the donor individual are not the same individuals.

In some embodiments, the present disclosure provides a method for performing cell transplantation in a recipient individual in need thereof, the method generally involving: (i) genetically modifying a host post-natal fibroblast with one or more nucleic acids comprising nucleotide sequences encoding Gata4, Mef2c, Tbx5, Mesp1, and Esrrg polypeptides (or a subset of reprogramming factors comprising Gata4, Mef2c, Tbx5, Mesp1, and Esrrg polypeptides), where the host post-natal fibroblasts are obtained from a donor individual, wherein the donor individual is immunocompatible with the recipient individual; and (ii) transplanting one or more of the genetically modified post-natal fibroblasts into the recipient individual. In some embodiments, the recipient individual and the donor individual are the same individual. In some embodiments, the recipient individual and the donor individual are not the same individuals.

In some embodiments, the present disclosure provides a method for performing cell transplantation in a recipient individual in need thereof, the method generally involving: (i) modifying a host post-natal fibroblast by introducing into the host post-natal fibroblast Gata4, Mef2c, Tbx5, Mesp1, and Esrrg polypeptides (or a subset of reprogramming factors comprising Gata4, Mef2c, Tbx5, Mesp1, and Esrrg polypeptides), where the host post-natal fibroblasts are obtained from a donor individual, wherein the donor individual is immunocompatible with the recipient individual; and (ii) transplanting one or more of the modified post-natal fibroblasts into the recipient individual. In some embodiments, the recipient individual and the donor individual are the same individual. In some embodiments, the recipient individual and the donor individual are not the same individuals.

A subject method of generating induced cardiomyocytes is useful for generating artificial heart tissue, e.g., for implanting into a mammalian subject in need thereof. In some embodiments, a subject treatment method involves administering to an individual in need thereof a subject artificial heart tissue.

A subject treatment method is useful for replacing damaged heart tissue (e.g., ischemic heart tissue; cardiac tissue that has been injured). Where a subject method involves introducing (implanting) an induced cardiomyocyte into an individual, allogeneic or autologous transplantation can be carried out.

The present disclosure provides methods of treating a cardiac disorder in an individual, the method generally involving administering to an individual in need thereof a therapeutically effective amount of: a) a population of induced cardiomyocytes prepared using a subject method; b) a population of genetically modified post-natal fibroblasts prepared using a subject method; c) a population of modified post-natal fibroblasts prepared using a subject method; or d) an artificial heart tissue prepared using a subject method.

For example, in some embodiments, a subject method comprises: i) generating an induced cardiomyocyte in vitro, as described above; and ii) introducing the induced cardiomyocyte into an individual in need thereof. In other embodiments, a subject method comprises: i) genetically modifying a host post-natal fibroblast with one or more nucleic acids comprising nucleotide sequences encoding Gata4, Mef2c, Tbx5, Mesp1, and Esrrg polypeptides (or a subset of reprogramming factors comprising Gata4, Mef2c, Tbx5, Mesp1, and Esrrg polypeptides); and ii) introducing the genetically modified post-natal fibroblasts into an individual in need thereof.

In other embodiments, a subject method comprises: i) modifying a host post-natal fibroblast by introducing into the host post-natal fibroblast Gata4, Mef2c, Tbx5, Mesp1, and Esrrg polypeptides (or a subset of reprogramming factors comprising Gata4, Mef2c, Tbx5, Mesp1, and Esrrg polypeptides); and ii) introducing the modified post-natal fibroblasts into an individual in need thereof.

In other embodiments, a subject method comprises: i) generating artificial heart tissue by: a) generating an induced cardiomyocyte, as described above; and b) associating the induced cardiomyocyte with a matrix, to form artificial heart tissue; and ii) introducing the artificial heart tissue into an individual in need thereof. In other embodiments, a subject comprises: i) generating artificial heart tissue by: a) genetically modifying a host post-natal fibroblast with one or more nucleic acids comprising nucleotide sequences encoding Gata4, Mef2c, Tbx5, Mesp1, and Esrrg polypeptides (or a subset of reprogramming factors comprising Gata4, Mef2c, Tbx5, Mesp1, and Esrrg polypeptides); and b) associating the genetically modified post-natal fibroblasts with a matrix, to form artificial heart tissue; and ii) introducing the artificial heart tissue into an individual in need thereof. In other embodiments, a subject comprises: i) generating artificial heart tissue by: a) modifying a host post-natal fibroblast by introducing into the host post-natal fibroblast one or more of Gata4, Mef2c, Tbx5, Mesp1, and Esrrg polypeptides (or a subset of reprogramming factors comprising Gata4, Mef2c, Tbx5, Mesp1, and Esrrg polypeptides); and b) associating the modified post-natal fibroblasts with a matrix, to form artificial heart tissue; and ii) introducing the artificial heart tissue into an individual in need thereof. The artificial heart tissue can be introduced into, on, or around existing heart tissue in the individual.

Individuals in need of treatment using a subject method and/or donor individuals include, but are not limited to, individuals having a congenital heart defect; individuals suffering from a degenerative muscle disease; individuals suffering from a condition that results in ischemic heart tissue, e.g., individuals with coronary artery disease; and the like. In some examples, a subject method is useful to treat a degenerative muscle disease or condition, e.g., familial cardiomyopathy, dilated cardiomyopathy, hypertrophic cardiomyopathy, restrictive cardiomyopathy, or coronary artery disease with resultant ischemic cardiomyopathy. In some examples, a subject method is useful to treat individuals having a cardiac or cardiovascular disease or disorder, e.g., cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism.

Individuals who are suitable for treatment with a subject method include individuals (e.g., mammalian subjects, such as humans; non-human primates; experimental non-human mammalian subjects such as mice, rats, etc.) having a cardiac condition including but not limited to a condition that results in ischemic heart tissue, e.g., individuals with coronary artery disease; and the like. In some examples, an individual suitable for treatment suffers from a cardiac or cardiovascular disease or condition, e.g., cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism. In some examples, individuals suitable for treatment with a subject method include individuals who have a degenerative muscle disease, e.g., familial cardiomyopathy, dilated cardiomyopathy, hypertrophic cardiomyopathy, restrictive cardiomyopathy, or coronary artery disease with resultant ischemic cardiomyopathy.

For administration to a mammalian host, a population of induced cardiomyocytes, or a population of genetically modified post-natal fibroblasts, generated using a subject method can be formulated as a pharmaceutical composition. A pharmaceutical composition can be a sterile aqueous or non-aqueous solution, suspension or emulsion, which additionally comprises a physiologically acceptable carrier (i.e., a non-toxic material that does not interfere with the activity of the cardiomyocytes). Any suitable carrier known to those of ordinary skill in the art may be employed in a subject pharmaceutical composition. The selection of a carrier will depend, in part, on the nature of the substance (i.e., cells or chemical compounds) being administered. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

In some embodiments, an induced cardiomyocyte population, a population of modified post-natal fibroblasts, or a population of genetically modified post-natal fibroblasts, is encapsulated, according to known encapsulation technologies, including microencapsulation (see, e.g., U.S. Pat. Nos. 4,352,883; 4,353,888; and 5,084,350). Where the cardiomyocytes, the modified post-natal fibroblasts, or the genetically modified post-natal fibroblasts are encapsulated, in some embodiments the cardiomyocytes, the modified post-natal fibroblasts, or the genetically modified post-natal fibroblasts are encapsulated by macroencapsulation, as described in U.S. Pat. Nos. 5,284,761; 5,158,881; 4,976,859; 4,968,733; 5,800,828 and published PCT patent application WO 95/05452.

In some embodiments, an induced cardiomyocyte population, a population of modified post-natal fibroblasts, or a population of genetically modified post-natal fibroblasts, is present in a matrix, as described below.

A unit dosage form of an induced cardiomyocyte population, a population of modified post-natal fibroblasts, or a population of genetically modified post-natal fibroblasts, can contain from about $10^3$ cells to about $10^9$ cells, e.g., from about $10^3$ cells to about $10^4$ cells, from about $10^4$ cells to about $10^5$ cells, from about $10^5$ cells to about $10^6$ cells, from about $10^6$ cells to about $10^7$ cells, from about $10^7$ cells to about $10^8$ cells, or from about $10^8$ cells to about $10^9$ cells.

An induced cardiomyocyte population, a population of modified post-natal fibroblasts, or a population of genetically modified post-natal fibroblasts, can be cryopreserved according to routine procedures. For example, cryopreservation can be carried out on from about one to ten million cells in "freeze" medium which can include a suitable proliferation medium, 10% serum albumin (e.g., human serum albumin; bovine serum albumin; and the like) and 7.5% dimethylsulfoxide. Cells are centrifuged. Growth medium is aspirated and replaced with freeze medium. Cells are resuspended as spheres. Cells are slowly frozen, by, e.g., placing in a container at −80° C. Cells are thawed by swirling in a 37° C. bath, resuspended in fresh proliferation medium, and grown as described above.

Artificial Heart Tissue

In some embodiments, a subject method comprises: a) reprogramming a population of post-natal fibroblasts into cardiomyocytes in vitro, e.g., where the post-natal fibroblasts are present in a matrix, wherein a population of induced cardiomyocytes is generated; and b) implanting the population of induced cardiomyocytes into or on an existing heart tissue in an individual. Thus, the present disclosure provides a method for generating artificial heart tissue in vitro; and implanting the artificial heart tissue in vivo. In some embodiments, a subject method comprises: a) reprogramming a population of post-natal fibroblasts into cardiomyocytes in vitro, generating a population of induced cardiomyocytes; b) associating the induced cardiomyocytes with a matrix, forming an artificial heart tissue; and c) implanting the artificial heart tissue into or on an existing heart tissue in an individual.

The artificial heart tissue can be used for allogeneic or autologous transplantation into an individual in need thereof. To produce artificial heart tissue, a matrix can be provided which is brought into contact with the post-natal fibroblasts, where the post-natal fibroblasts are reprogrammed into cardiomyocytes using a subject method, as described above. This means that this matrix is transferred into a suitable vessel and a layer of the cell-containing culture medium is placed on top (before or during the reprogramming of the post-natal fibroblasts). The term "matrix" should be understood in this connection to mean any suitable carrier material to which the cells are able to attach themselves or adhere in order to form the corresponding cell composite, i.e. the artificial tissue. In some embodiments, the matrix or carrier material, respectively, is present already in a three-dimensional form desired for later application. For example, bovine pericardial tissue is used as matrix which is crosslinked with collagen, decellularized and photofixed.

For example, a matrix (also referred to as a "biocompatible substrate") is a material that is suitable for implantation into a subject onto which a cell population can be deposited. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. The biocompatible substrate provides the supportive framework that allows cells to attach to it, and grow on it. Cultured populations of cells can then be grown on the biocompatible substrate, which provides the appropriate interstitial distances required for cell-cell interaction.

Treatment Methods Using Polypeptides or Nucleic Acids

The present disclosure provides methods of reprogramming a fibroblast into a cardiomyocyte in vivo.

In some embodiments, the methods generally involve contacting a fibroblast in vivo with a reprogramming composition. As discussed above, a reprogramming composition comprises either: 1) Gata4, Mef2c, Tbx5, Mesp1, and Esrrg polypeptides (or a subset of reprogramming factors comprising Gata4, Mef2c, Tbx5, Mesp1, and Esrrg polypeptides); or 2) one or more nucleic acids comprising nucleotide sequences encoding Gata4, Mef2c, Tbx5, Mesp1, and Esrrg polypeptides (or a subset of reprogramming factors comprising Gata4, Mef2c, Tbx5, Mesp1, and Esrrg polypeptides). As described above, a subject reprogramming composition can comprise one or more additional components. A subject reprogramming composition can be administered to an individual at or near a treatment site, e.g., in or around the heart.

In some embodiments, the methods generally involve contacting a fibroblast in vivo with a reprogramming composition. As discussed above, a reprogramming composition comprises either: 1) a mixture of Gata4, Mef2c, Tbx5, Mesp1, and Esrrg polypeptides (or a subset of reprogramming factors comprising Gata4, Mef2c, Tbx5, Mesp1, and Esrrg polypeptides); or 2) one or more nucleic acids comprising nucleotide sequences encoding Gata4, Mef2c, Tbx5, Mesp1, and Esrrg polypeptides (or a subset of reprogramming factors comprising Gata4, Mef2c, Tbx5, Mesp1, and Esrrg polypeptides). As described above, a subject reprogramming composition can comprise one or more additional components. A subject reprogramming composition can be administered to an individual at or near a treatment site, e.g., in or around the heart.

In some embodiments, a reprogramming composition is introduced into an individual in need thereof in association with an implantable device. Thus, in some embodiments, the present disclosure provides methods of reprogramming a fibroblast into a cardiomyocyte in vivo, the methods generally involving introducing a subject implantable device (comprising a subject reprogramming composition) into an individual in need thereof, where the implantable device is introduced at or near a treatment site, e.g., in or around the heart.

Individuals in need of treatment using a subject method and/or donor individuals include, but are not limited to, individuals having a congenital heart defect; individuals suffering from a degenerative muscle disease; individuals suffering from a condition that results in ischemic heart tissue, e.g., individuals with coronary artery disease; and the like. In some examples, a subject method is useful to treat a degenerative muscle disease or condition, e.g., familial cardiomyopathy, dilated cardiomyopathy, hypertrophic cardiomyopathy, restrictive cardiomyopathy, or coronary artery disease with resultant ischemic cardiomyopathy. In some examples, a subject method is useful to treat individuals having a cardiac or cardiovascular disease or disorder, e.g., cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism.

Individuals who are suitable for treatment with a subject method include individuals (e.g., mammalian subjects, such as humans; non-human primates; experimental non-human mammalian subjects such as mice, rats, etc.) having a cardiac condition including but not limited to a condition that results in ischemic heart tissue, e.g., individuals with coronary artery disease; and the like. In some examples, an individual suitable for treatment suffers from a cardiac or cardiovascular disease or condition, e.g., cardiovascular disease, aneurysm, angina, arrhythmia, atherosclerosis, cerebrovascular accident (stroke), cerebrovascular disease, congenital heart disease, congestive heart failure, myocarditis, coronary valve disease, dilated coronary artery disease, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism. In some examples, individuals suitable for treatment with a subject method include individuals who have a degenerative muscle disease, e.g., familial cardiomyopathy, dilated cardiomyopathy, hypertrophic cardiomyopathy, restrictive cardiomyopathy, or coronary artery disease with resultant ischemic cardiomyopathy.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Direct Reprogramming of Human Fibroblasts into Functional Cardiomyocytes by Defined Factors In this study, cardiomyocytes were reprogrammed directly from fully differentiated human fibroblasts. Cardiac reprogramming was carried out first using human ES cell-derived fibroblasts, which contain fluorescence reporter driven by cardiac promoter. Numerous key developmental cardiac regulators were screened. It was found that a specific combination of five transcription factors is sufficient to rapidly and efficiently generate functional cardiomyocytes directly from human ES cell-derived fibroblasts, and also from human fetal cardiac fibroblasts and neonatal foreskin fibroblast.

Materials and Methods

Human Embryonic Stem Cell Culture and Fibroblast Differentiation

The alpha-myosin heavy chain (αMHC)-mCherry stable H9 human embryonic stem (ES) cells (Kita-Matsuo et al., 2009) were grown on Matrigel (growth factor-reduced, BD Bioscience)-coated 6-well plates (Corning, Inc.) in mTeSR1 media (StemCell Technologies), and passaged following dispase digestion. For fibroblast differentiation, embryoid bodies (EBs) were formed from enzymatically dispersed human ES cells suspended in low-attachment plates for 7 days, then plated on gelatin-coated dishes and cultured in medium (DMDM/20% FBS) for another 7 days. The migrated cells were harvested and filtered with 40-μm cell strainers (BD). For αMHC-mCherry⁻/Thy1⁺ cell sorting, cells were incubated with allophycocyanin (APC)-conjugated anti-Thy1 antibody (eBioscience) and sorted by fluorescence activated cell sorting using fluorescence activated cell sorting (FACS) Aria 2 (BD Biosciences). The purified fibroblasts were further cultured in M106 with low serum growth supplement (LSGS) (Invitrogen), and passaged by trypsin digestion in a 1:3 split ratio. The fibroblasts with passage number from 6 to 12 were used for reprogramming by retrovirus.

Cardiomyocytes Differentiation from Human Embryonic Stem Cells

Cardiomyocyte were differentiated from αMHC-mCherry stable H9 human ES cells with Matrix Sandwich Method. In brief, undifferentiated H9 human ES cells were dissociated into single cell by Versene (Invitrogen), and 1×10$^6$ cells in mTeSR1 media were seeded into each well of a Matrigel coated 6-well plate. Cells were coated with Matrigel in mTesR1, when cells became ~80% confluent. RPMI/B27 containing Matrigel and activin A (StemRD) was used to initiate cardiac differentiation, when cells reached 100% confluence. Media were exchanged to RPMI/B27 containing Bmp4 and beta-fibroblast growth factor (βFGF) (R&D) on day 1 differentiation, and then exchanged to RPMI/B27 complete supplement on day 5 with medium changing every three days. Contracting mcherry⁺ ES cell-derived cardiomyocytes were observed from day 8, and sorted out at day 21 to day 28 by FACS Aria 2.

Molecular Cloning and Retroviral (RV) Infection

Retroviruses were generated as described (Kitamura et al., 2003; Takahashi and Yamanaka, 2006). Briefly, to construct pMXs retroviral vectors, the coding regions of candidate genes were amplified by polymerase chain reaction (PCR) and were subcloned into pMXs vector. The pMXs retroviral vectors were transfected into Plat-E cells with Fugene 6 (Roche) to generate viruses. Pool of virus-containing supernatants was used for transduction. After 24 h, the medium was replaced with DMEM/M199 medium and changed every 2-3 days. To improve the transduction efficiency of retroviruses, the purified fibroblasts were first transduced with lentivirus to express mouse receptor for retroviruses, Slc7a1 (Verrey et al., 2004). This strategy yielded a transduction efficiency of 50-70% in different batches of fibroblasts, which green fluorescent protein (GFP) was introduced by retrovirus.

For the tetracycline-inducible system, Retro-X Tet-ON Advanced Systems (Clontech) was used according to the manufacturer's recommendations. To construct pRetro-X-Tight-cDNA vectors, the coding regions of EGFP, ESRRG, GATA4, MEF2C, MESP1, and TBX5 were amplified by PCR and subcloned into pRetro-X-Tight-Puro$^R$ vector. The pRetro-X-Tet-On Advanced-Neo$^R$ or pRetro-X-tight-cDNA retroviral vectors and packaging constructs, pGag/Pol and pVSV-G, were transfected into HEK293FT cells with Lipofectamine 2000 (Invitrogen) to generate viruses, and virus-containing supernatants were collected after 48 hr. Cells were transduced with Retro-X-Tet ON and Retro-X-Tight-cDNA overnight supplemented with 5 μg/ml polybrene, and purified by positive selection of puromycin and neomycin. Doxycycline (100 ng/ml) was used for gene induction.

FACS Analyses and Sorting

For mCherry expression analyses, cells were digested into single cell from cultured dishes and analyzed on a FACS LSR-II (BD Biosciences) with FlowJo software. For αMHC-mCherry/cTnT expression, cells were fixed with 4% paraformaldehyde (PFA) for 15 min, permeabilized with Saponin, and stained with anti-dsRed and anti-cardiac troponin T (anti-cTnT) antibodies, followed by secondary antibodies conjugated with Alexa 585 and 647.

Cell Transplantation

Fibroblasts were harvested the next day after retroviral infection. A left thoracotomy was carried out in non-obese diabetic-severe combined immunodeficient (NOD-SCID) mice, and 10$^6$ cultured cells were injected into the left ventricle. After 2-8 weeks, the hearts were excised for immunohistochemistry, or dissociated for single cardiomyocyte isolation.

Immunocytochemistry

Cells were fixed in 4% paraformaldehyde for 15 min at room temperature, permeabilized with Saponin, blocked, and incubated with primary antibodies against sarcomeric α-actinin (Sigma Aldrich), vimentin (Progen), red fluorescent protein (RFP) (AbCam), cTnT (Thermo Scientific), or cardiac myosin heavy chain (MHC) (AbCam), then with secondary antibodies conjugated with Alexa 488 or 594 (Molecular Probes), and 4',6-diamidino-2-phenylindole (DAPI) (Invitrogen).

Histology

For immunohistochemical studies in cell-injected hearts, hearts were fixed in 0.4% paraformaldehyde overnight, embedded in OCT compound, and frozen in liquid nitrogen. (Ieda et al., 2010; Ieda et al., 2009) Hearts were cut vertically in 7-μm sections to show both ventricles. Sections were stained with primary antibodies against GFP or α-actinin, with secondary antibodies conjugated with Alexa 488 or 594, and DAPI.

Quantitative RT-PCR

Total RNA was isolated from cells, and quantitative reverse transcription-polymerase chain reaction (qRT-PCR) was performed on an ABI 7900HT (Applied Biosystems) with TaqMan probes (Applied Biosystems): ACTC1 (Hs01109515_m1), ACTN2 (Hs00153809_m1), NPPA (Hs00383230_g1), MYH6 (Hs00411908_m1), MYL7 (Hs00221909_m1), MYL2 (Hs00166405_m1), TNNT2 (Hs00165960_m1), ATP2A2 (Hs01566028_g1), PLN (Hs00160179_m1), RYR2 (Hs00892842_m1). The mRNA levels were normalized by comparison to GAPDH (Hs02758991_g1) mRNA.

Whole Transcriptome Shotgun Sequencing

Figure 4:
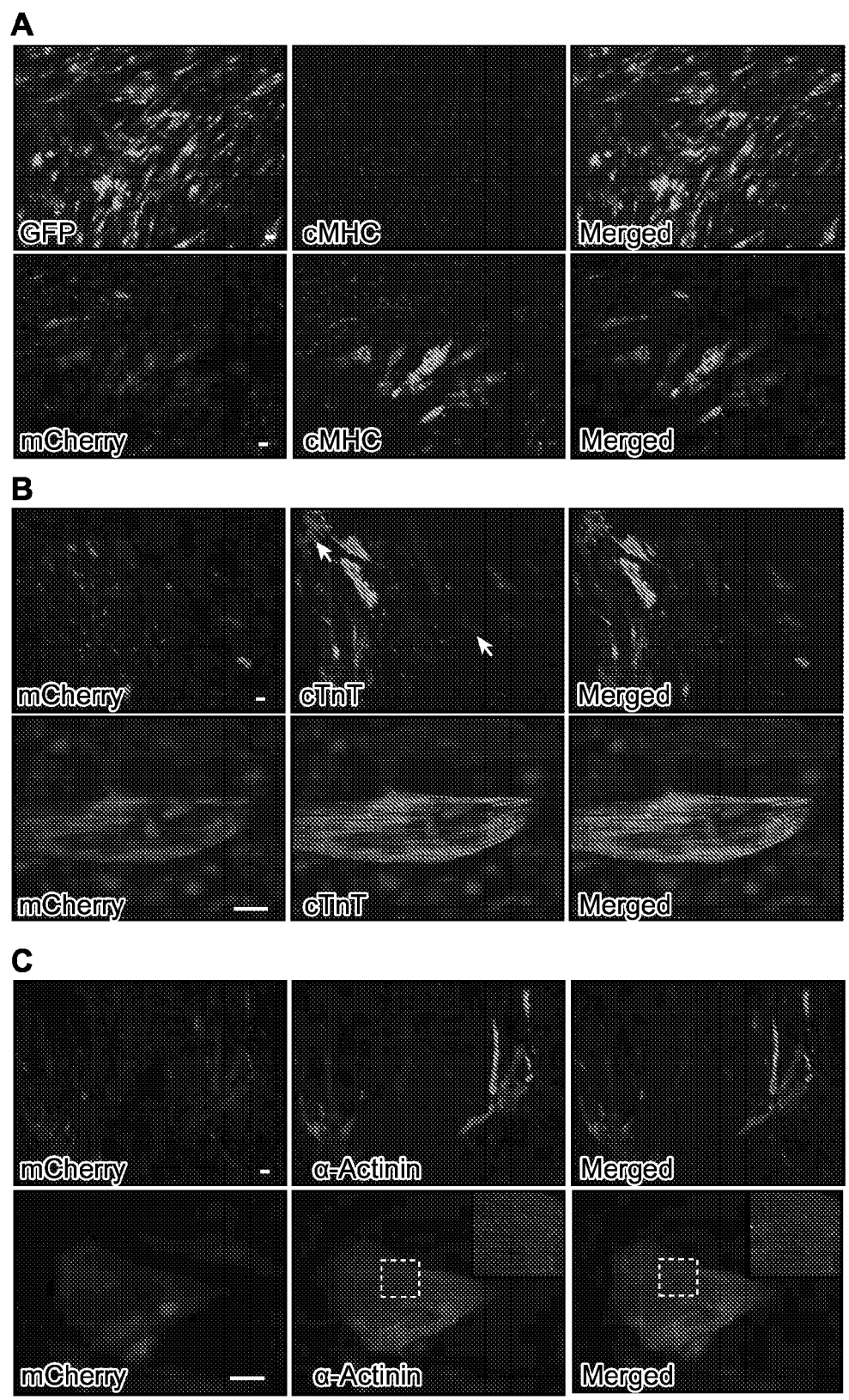
FIGS. 4A-G depict expression of cardiac proteins in mCherry$^+$ cells transduced with ESRRG, GATA4, MEF2C, MESP1, and TBX5.

Human genome-wide gene expression analyses were performed using Whole Transcriptome Shotgun Sequencing. αMHC-mCherry⁺ H9-derived cardiomyocytes (CMs) were collected by FACS. 5-factor transduced mCherry⁺ cells and mCherry⁻ cells were collected by FACS after 2 and 4 weeks of culture. RNA was extracted using PicoPure RNA Isolation (Arcturus). Microarray analyses were performed in triplicate from independent biologic samples, according to the standard Affymetrix Genechip protocol. Data were analyzed using the Affymetrix Power Tool (APT, version 1.8.5). Linear models were fitted for each gene on the sample group to derive estimated group effects and their associated significance with the limma package (Smyth, 2004) in R/Bioconductor. Moderated t-statistics and the associated p-values were calculated. P-values were adjusted for multiple testing by controlling for false-discovery rate by the Benjamini-Hochberg method. Gene annotations were retrieved from Affymetrix (version Nov. 12, 2007). Differential gene expression was defined using the statistics/threshold combination. Genes differentially expressed in at least one comparison (FDR-adj p<0.0001) are shown in FIG. 4F.

Chromatin Immunoprecipitation Assay

Chromatin immunoprecipitations were performed on human ES cell-derived fibroblasts, iCMs and human ES cell-differentiated CMs. Immunoprecipitations were carried out using the Imprint Chromatin Immunoprecipitation Kit (Sigma) following the manufacturer instructions. Antibodies against 3 mH3K27 and 3 mH3K4 were from Active motif, and normal rabbit IgG was from Cell Signaling Technology.

Bisulfite Genomic Sequencing

Bisulfite treatment was performed using the Epitect Bisulfite Kit (Qiagen) according to the manufacturer's recommendations. PCR primers are listed below: MYH6-sense: GGGAGGAATGTGTTTAAGGATTAAAAA (SEQ ID NO:31), MYH6-Antisense:TACAAAACATCCCAC-CCCAAACCTC (SEQ ID NO:32). MYH7-Sense: ATTG-GTTGTTTGTGGTTTTGGTGGT (SEQ ID NO:33), MYH7-Antisense: TAAAAACATTTCCCCCAAACTC-CCCC (SEQ ID NO:34). NPPA-Sense: AATTAGGGGAGT-TGGGTATTAGTTAAG (SEQ ID NO:35), NPPA-Antisense: CCCACTTCAAAAATATAAAAAAAATAAAAA (SEQ ID NO:36)). Amplified products were cloned into pCR2.1-TOPO (Invitrogen). Ten randomly selected clones were sequenced with the M13 forward and M13 reverse primers for each gene.

$Ca^{2+}$ Imaging $Ca^{2+}$ imaging was performed according to the standard protocol. Briefly, cells were labeled with Fluo-4-AM (Invitrogen) for 30 minutes at 37° C., washed, and incubated for an additional 30 minutes at room temperature to allow de-esterification of the dye. Fluo-4 labeled cells were analyzed by Axio Observer (Zeiss) with MiCAM02 (SciMedia) at 37° C.

Statistical Analyses

Differences between groups were examined for statistical significance using Student's t-test or ANOVA. P values of <0.05 were regarded as significant.

Results

GATA4, MEF2C and TBX5 are Insufficient to Reprogram Human Fibroblast into Cardiomyocytes or Cardiomyocyte-Like Cells To visualize the success of cardiac reprogramming in human cells, fibroblasts differentiated from transgenic H9 human ES cells, in which the red fluorescent protein (mCherry) is driven by mouse αMHC promoter (αMHC-mCherry) (Kita-Matsuo et al., 2009), were used. Consistent with previous results, mCherry was expressed only in beating cardiomyocytes, but not in other cell types including fibroblasts after human ES cell differentiation (FIG. 1A-1D). 96% of mCherry$^+$ cells, sorted by FACS, expressed cardiac troponin T (FIG. 1F). Therefore, the induction of cardiomyocytes from H9 human ES cell-derived fibroblasts (H9Fs) could be analyzed quantitatively by reporter-based fluorescence-activated cell sorting (FACS).

To avoid contamination of cardiomyocytes, human ES cell-derivatives were stained with antibody anti-Thy1, one marker of cardiac fibroblasts (Hudon-David et al., 2007), and Thy1$^+$/mCherry$^-$ fibroblasts were sorted out by FACS (FIG. 1G-1H). After FACS purification, all of Thy1$^+$/mCherry$^-$ cells expressed other fibroblast markers, Prolyl-4-Hydroxylase β and vimentin, but none of them expressed cardiac troponin T, a specific sarcomeric marker of differentiated cardiomyocytes (FIG. 1I-1J).

FIGS. 1A-J.

(A) Fibroblasts were differentiated from aMHC-mCherry H9 ES cells (B). mCherry was expressed only in beating CMs (C, D). 96% of mCherry$^+$ cells were cardiac troponin T (cTnT)$^+$ CMs (F), although only half of cTnT$^+$ CMs expressed mCherry (E). G), Scheme of the differentiation and reprogramming of H9 ES cell-derived fibroblasts (H9Fs). H-J) All of Thy1$^+$/mCherry$^-$ H9Fs, purified by cell sorter, were positive for fibroblast markers, Prolyl-4-Hydroxylase b and vimentin, but none of them expressed cTnT.

Figure 2:
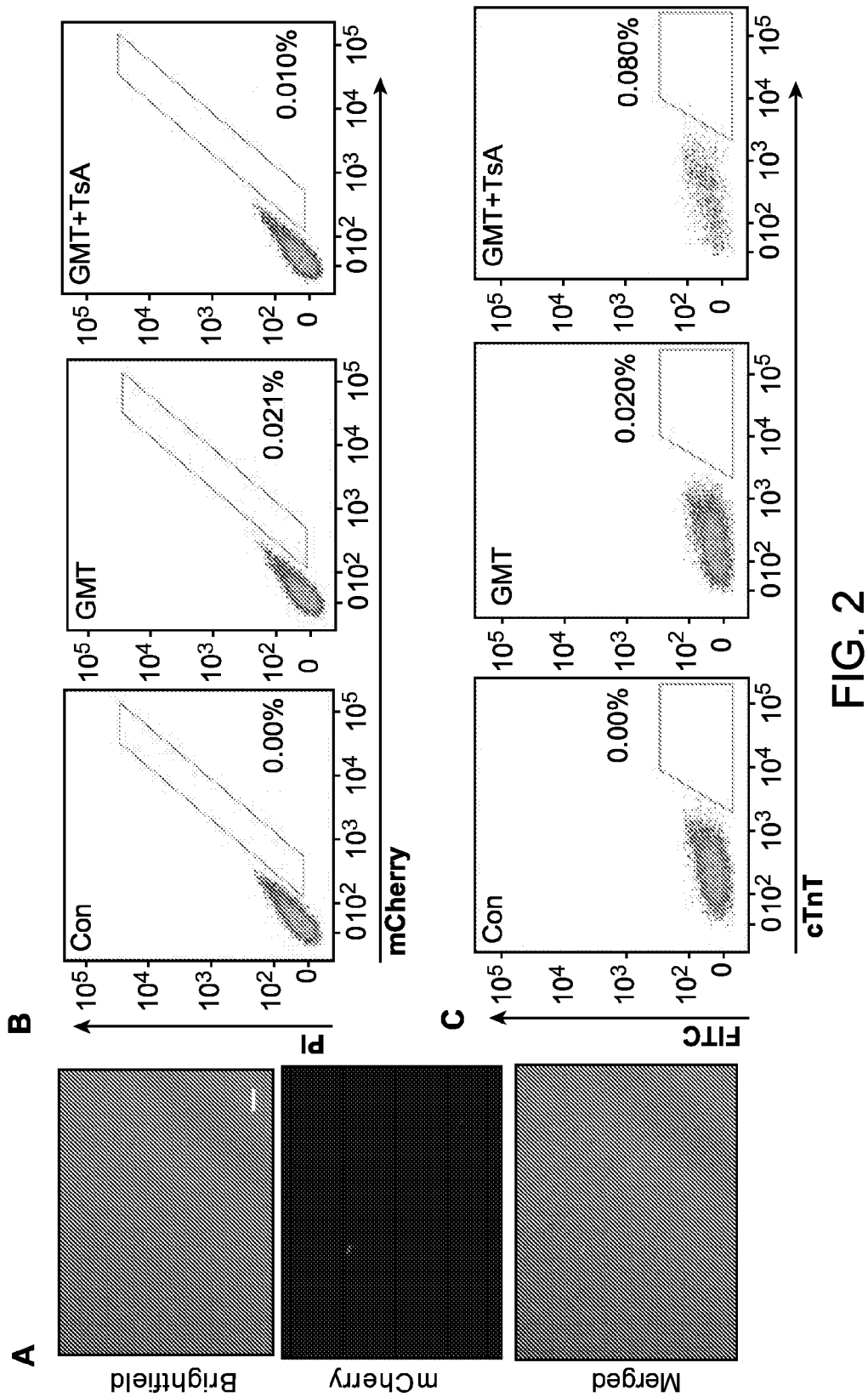
FIGS. 2A-F depict results of transducing H9-derived fibroblasts (H9Fs) with GATA4, MEF2C, and TBX5 (collectively referred to as "GMT").

It was tested whether three transcription factors (GATA4, MEF2C and TBX5) are sufficient to reprogram human fibroblasts into cardiomyocytes, as they did in mouse fibroblasts (Ieda et al., 2010). GATA4, MEF2C and TBX5 (collectively referred to as "GMT") were successfully introduced into H9Fs by retrovirus. Almost no mCherry$^+$ cells were observed in H9Fs even 4 weeks after 3-factor retrovirus infections. Only 2~5 mcherry$^+$ cells appeared among $10^5$ initiated cells (FIG. 2A). No mCherry$^+$ and cardiac troponin T (cTnT)$^+$ cells were detected by FACS at 2 weeks after the 3-factor transduction, even in the presence of trichostatin A (TSA), a histone deacetylase inhibitor (FIG. 2B-C). Inhibitors of epigenetic modifiers reported to improve iPSC reprogramming, including TSA, valproic acid, and the DNA methyltransferase inhibitor 5-aza-2'-deoxycytidine, were not sufficient to promote conversion of human CMs by GMT. The same negative results were consistently observed in human dermal fibroblasts. Cardiac myosin heavy chain (MHC) and troponin T were not expressed in dermal fibroblasts transduced with 3-factor retrovirus. These negative results indicated that GATA4, MEF2C and TBX5 are not sufficient to efficiently reprogram human fibroblast into cardiomyocytes.

Screening Cardiac Inducing Factors for Reprogramming Human Fibroblasts

To select potential cardiac reprogramming factors, the microarray data were re-analyzed to identify transcription factors and epigenetic remodeling factors with greater expression in mouse cardiomyocytes than in cardiac fibroblasts (Ieda et al., 2009). Among them, 16 transcription factors or co-activators, which exhibited severe developmental cardiac defects and embryonic lethality when mutated, were selected. Three growth factors were also included, to assess whether autocrine or paracrine growth factors can improve cardiac reprogramming. Each factor was subcloned separately into a retroviral vector (Takahasi et al., 2007) to enable the efficient expression of each gene, alone or in combination, in Thy1$^+$/mCherry$^-$ H9Fs.

Thy1$^+$/mCherry$^-$ H9Fs were transduced with a mixture of retroviruses expressing all 19 factors or with GFP retrovirus (negative control), as previously reported (Ieda et al., 2010). mCherry$^+$ cells were not observed in these H9Fs 2 weeks after GFP retrovirus infection or 2 weeks culture without any viral infection. In contrast, mCherry$^+$ cells were observed as early as 3-4 days after the 19-factor retroviral infection, the proportion of which dramatically increased 7-10 days postretroviral transduction (FIGS. 2D and 2E), indicating that 19 factors successfully activated the cardiac-enriched αMHC gene in some cells. These results also indicated that the cardiac reprogramming may require longer time in human fibroblasts than in mouse fibroblasts. Therefore, two weeks after retrovirus transduction was chosen as the time point at which to assay the reprogramming efficiency by FACS.

To determine which of the 19 factors were critical for activating cardiac gene expression, each individual factor was serially removed from the pool of 19. For example, compared with 19 factors, the 18-factor pools lacking FLI1 or SOX17 or WNT5A produced an increased number of mCherry$^+$ cells (FIG. 2D-2F), suggesting that FLI1, SOX17 and WNT5A inhibited cardiac reprogramming and should therefore be removed from the pool.

FIGS. 2A-F.

A), Rare mcherry$^+$ cells were observed in H9Fs transduced with GMT. Neither mCherry$^+$ cells (B), nor TnT$^+$ cells (C) were detected by FACS 2 weeks after GATA4, MEF2C and TBX5 transduction, even in the presence of a histone deacetylase inhibitor, trichostatin A (TsA). D-F) The screening of cardiac inducing factors was initiated from 19 factors (19Fs). D), Representative pictures of aMHC-mCherry$^+$ cells at day 10 after retrovirus transduction of 19Fs or 19Fs minus FLI1 or MYOCD. E), Summary of the number of mCherry$^+$ cells in H9Fs at Day 4, 7 or 10 after transduction with 19Fs or 19Fs minus one factor. F), Effect on aMHC-mCherry$^+$ cell induction of the removal of individual factor from the pool of 19 factors.

Figure 3:
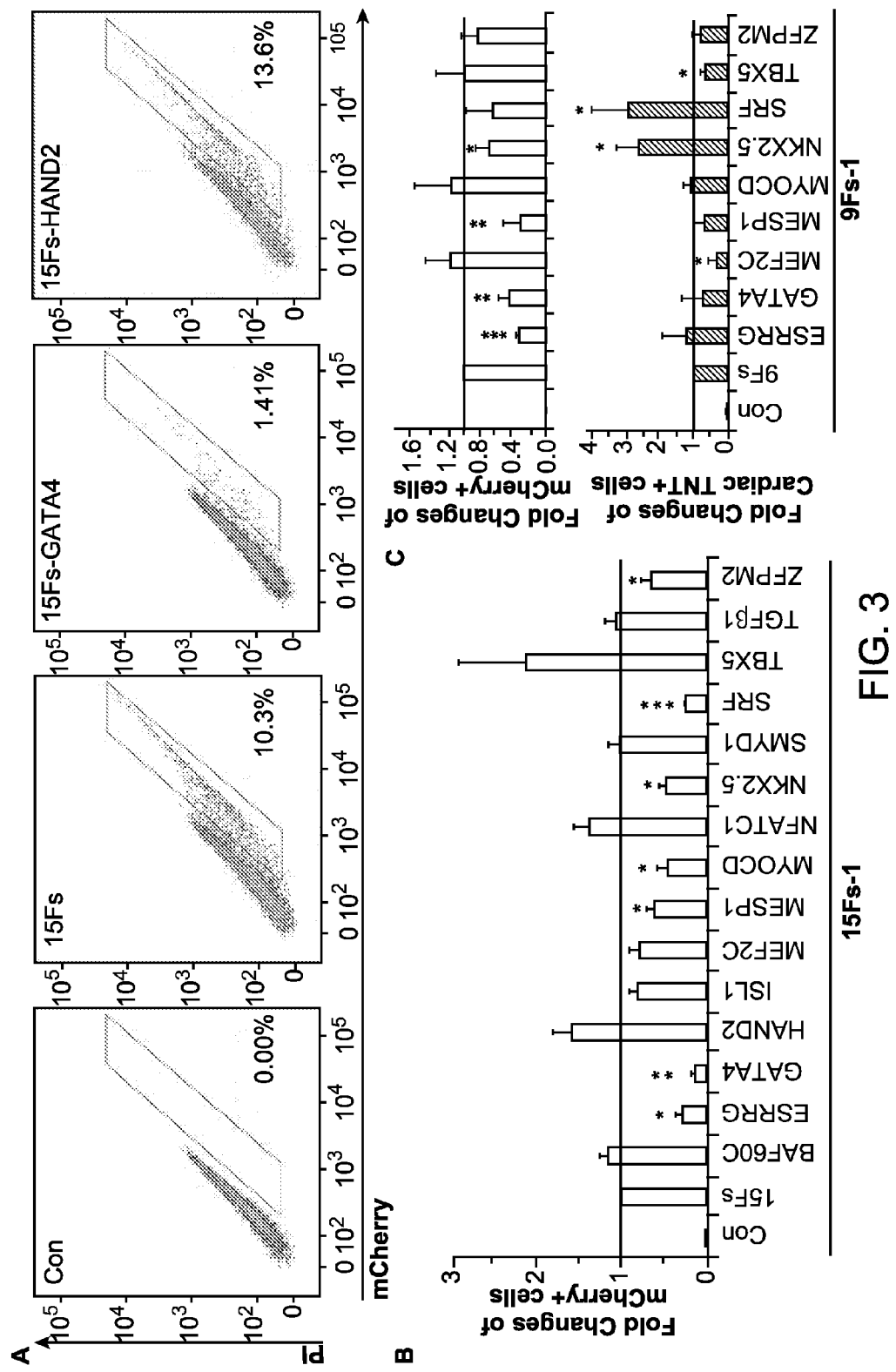
FIGS. 3A-G depict analysis of mCherry$^+$ cells 2 weeks after transduction with 15 factors (15Fs) minus one factor, 9 factors (9Fs) minus one factor, 7 factors (7Fs) minus one factor, or 5 factors (5Fs) minus one factor.
Figure 3:
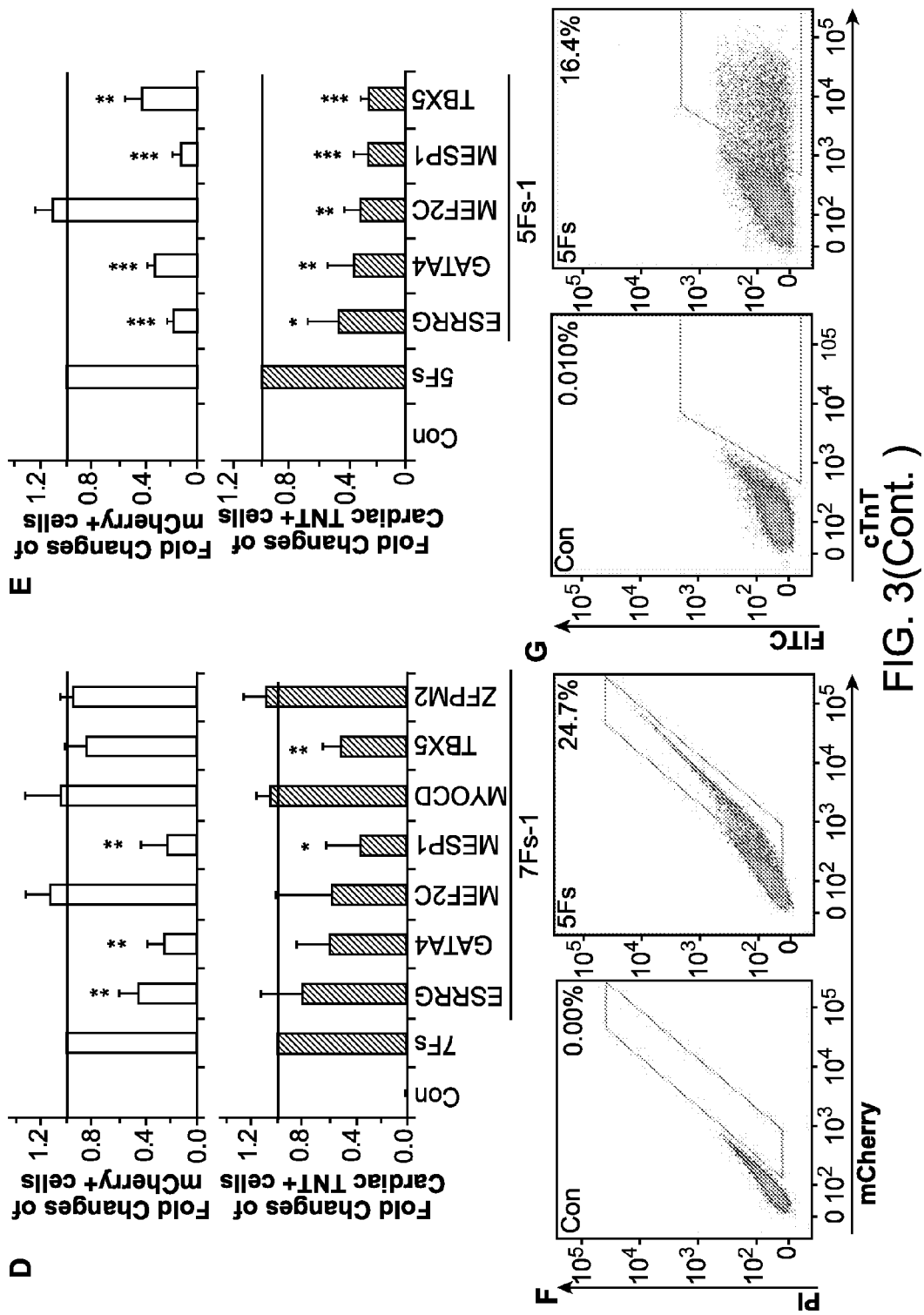

After removal of these three factors (FLI1, SOX17, and WNT5A) and IGF2, 15 factors resulted in a dramatic increase in the percentage of mCherry$^+$ cells up to 10.3% (FIG. 3A). Of note, those 14-factor pools lacking 7 factors (ESRRG, GATA4, MESP1, NKX2.5, SRF, MYOCD, and ZFPM2) significantly decreased the yield of mCherry$^+$ cells (FIG. 3A-B), while the non-significant change of mCherry$^+$ cells suggested that the other 8 factors are dispensable in this 15-factor setting. Six factors (BAF60C, HAND2, ISL1, NFATC1, SMYD1, and TGFβ1 were removed, but MEF2C and TBX5 were kept, to conduct the further 9-factor screening, because MEF2C and TBX5 are the key factors in mouse cardiomyocyte reprogramming.

ESRRG, GATA4, MEF2C, MESP1 and TBX5 are Sufficient to Efficiently Induce Cardiomyocytes from Human Fibroblasts In addition to mCherry fluorescence, the expression of cardiac troponin T (cTnT) was also examined by FACS from this round. Two further rounds of withdrawing single factors from nine- and seven-factor pools were conducted (FIGS. 3C and 3D), removing those that increased the efficiency or did not decrease the efficiency of reprogrammed mCherry$^+$ and cTnT$^+$ cells upon withdrawal. It was found that five factors (ESRRG, GATA4, MEF2C, MESP1, and TBX5) were sufficient to efficiently induce mCherry$^+$ and cTnT$^+$ cells from cardiac fibroblasts. Removing anyone of these five factors significantly decreased the induction efficiency of mCherry+ and/or cTnT+ cells (FIG. 3E). The combination of these five factors efficiently induced ~24.7% of fibroblasts to activate the aMHC-mCherry reporter (FIG. 3F), and ~16.4% of fibroblasts to become cTnT+ cells (FIG. 3G) 2 weeks after induction. These data demonstrated that the five factors are all required to efficiently induce cardiac gene expression in human fibroblasts. MYOCD and ZFPM2 were dispensable in 7-factor screening with removing only single factor (FIG. 3D), however, the 5-factor reprogramming efficiency was significantly lower than 7-factor efficiency. The combination of these 7 factors efficiently induced 17.1±10.8% of total fibroblasts to activate the aMHC-mCherry reporter (FIG. 3F), in which 57.5±11.0% cells expressed cTnT, and 12.2+8.9% of total fibroblasts to become cTnT$^+$ cells (FIG. 3G) 2 weeks after retroviral infection.

FIGS. 3A-G.

A), FACS plots for analyses of mCherry$^+$ cells 2 weeks after transduction of 15 factors (15Fs) or 15Fs minus GATA4 or HAND2. B), Effect on aMHC-mCherry$^+$ cell induction of the removal of individual factor from the pool of 15 factors. C-E), Effects on aMHC-mCherry$^+$ cell (upper) and TnT+ cell (lower) induction of the removal of individual factor from the pool of 9 factors (9Fs, C), 7 factors (7Fs, D), or 5 factors (5Fs, E). F-G), FACS Plots for analyses of mCherry$^+$ cells (F) and cTnT$^+$ cells (G) 2 weeks after transduction of 5 Factors.

Next, immunocytochemistry was used to determine if cardiac proteins were expressed in mCherry$^+$ cells. As expected, most mCherry$^+$ cells induced with the five factors expressed cardiac myosin heavy chain (cMHC) (FIG. 4A). In addition to cMHC, more than half of mCherry$^+$ cells expressed cTnT (FIG. 4B) and sarcomeric α-actinin (α-actinin), and had well defined sarcomeric structures (FIG. 4C), similar to H9-CMs, indicating mCherry$^+$ cells expressed several cardiomyocyte-specific markers. Four weeks after retroviral infection, enriched mitochondria and typical sarcomeres were observed in those 7-factor reprogrammed cells by using electron microscope (FIG. 4F). The average length of sarcomeres in reprogrammed cells was 1.08±0.32 μm (FIG. 4G). The same is also true for fetal human cardiac fibroblasts (HCFs) and neonatal human dermal fibroblasts (HDFs). The HCFs and HDFs transduced with the 5 factors and dsRed, expressed cMHC and cTnT 2 weeks after retrovirus infections (FIG. 4D-E). These data demonstrated that human induced CM-like cells (iCMs) can be rapidly and robustly generated directly from fibroblasts in vitro by 7 defined factors, ESRRG, GATA4, MEF2C, MESP1, MYOCD, TBX5 and ZFPM2.

FIGS. 4A-G.

A-C), αMHC-mCherry$^+$ induced cardiomyocytes (iCMs) expressed cardiac myosin heavy chain (cMHC), cardiac troponin T (cTnT), and α-actinin with clear sarcomeric organization 2 weeks after transduction. D-E) Human fetal cardiac fibroblast (HCF) (D), and human neonatal dermal fibroblast (HCF) (E), transduced with the 5 factors and dsRed, expressed cardiac MHC and TnT. (F), 4 weeks after retroviral infection, 7-factor reprogrammed cells were observed enriched mitochondria and typical sarcomeres by using electron microscope. Scale bars represent 1 μm. (G), Summary of the length of sarcomeres in reprogrammed iCMs.

Induced Cardiomyocytes Resemble Cardiomyocytes in Gene Expression

Figure 5:
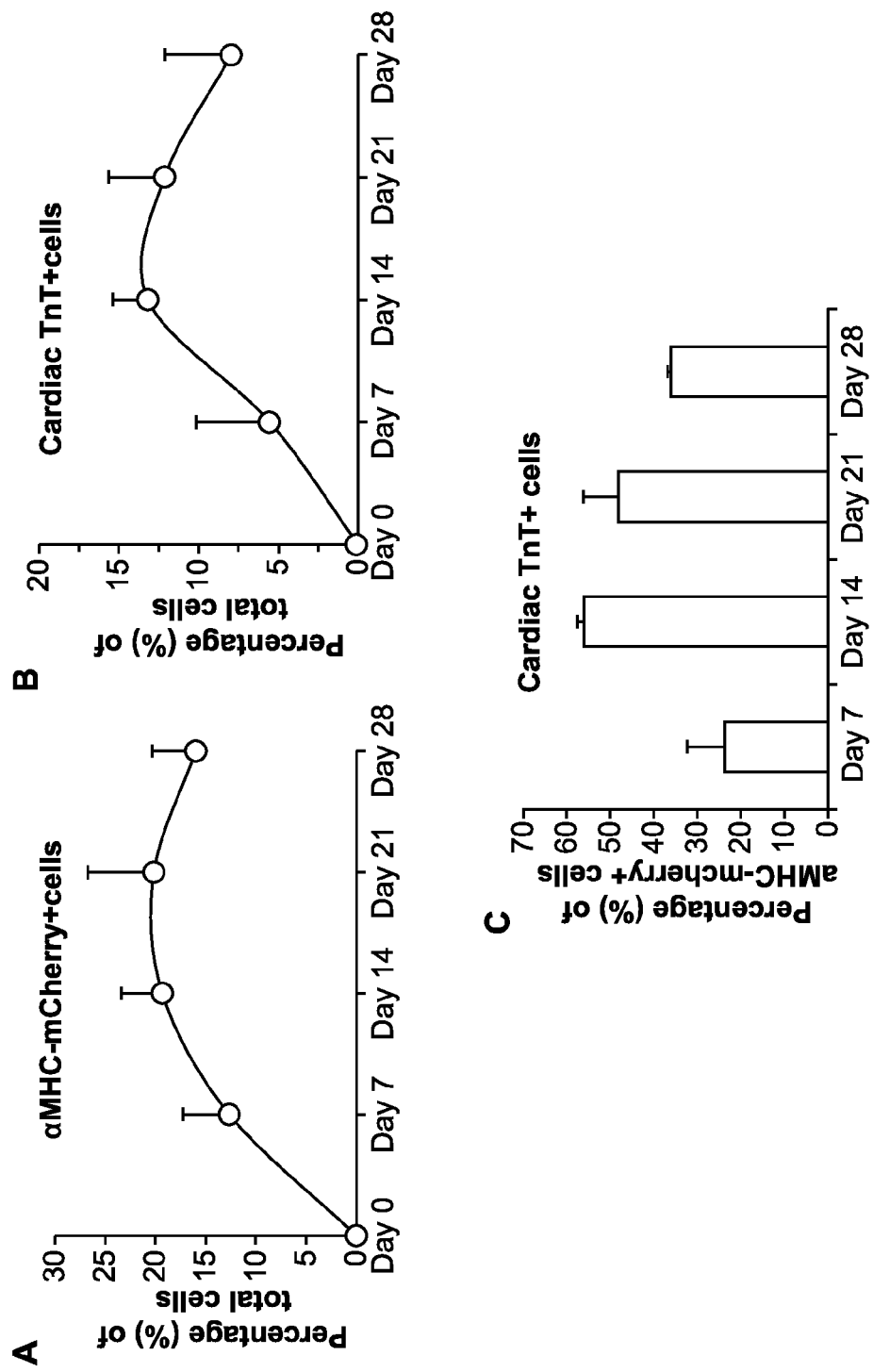
FIGS. 5A-E depict gene expression analysis of mCherry$^+$ cells transduced with ESRRG, GATA4, MEF2C, MESP1, and TBX5.

With quantitative assay by FACS, the time course of cardiomyocyte induction from H9Fs was analyzed. mCherry$^+$ cells were observed as early as 3 days after induction and gradually increased in number up to 10.9±2.3% at day 7, 19.3±4.1% at day 14 and reached the highest level between day 14 and 21 (FIG. 5A). It was observed that successfully reprogrammed cells were less proliferative than un-reprogrammed fibroblasts, and there were many dead mCherry$^+$ cells after 3-week culture in DMEM/M199 media; therefore, over time, mCherry$^+$ cells decreased in percentage relative to the total number of cells. Consistently, the percentage of cTnT$^+$ cells among the total cells and the α-MHC-mCherry$^+$ cells increased significantly in number up to 13.2±2.2% and 56.0±1.6%, respectively, at Day 14, and then decreased over time (FIGS. 5B and 5C).

To determine if other cardiac genes were enriched in mCherry$^+$ induced cardiomyocytes (iCMs), mCherry$^+$ iCMs were sorted at 2, 3 and 4 weeks after transduction with 5 factors and compared gene expression of cardiomyocyte-specific genes with H9-derived fibroblasts (H9Fs) and cardiomyocytes (H9-CMs) by quantitative RT-PCR (qPCR). The cardiomyocyte-specific genes, including ACTC1 (cardiac α-actin), ACTN2 (actinin a2), MYH6 (α-myosin heavy chain), MYL2 (myosin regulatory light chain 2, ventricular isoform), MYL7 (myosin regulatory light chain 2, atrial isoform), TNNT2 (troponin T type 2, cardiac), NPPA (natriuretic peptide precursor type A), PLN (phospholamban), and RYR2 (ryanodine receptor 2), were significantly upregulated in a time-dependent manner in mCherry$^+$ cells, but were not detected in H9Fs by qPCR (FIG. 5D). Especially, ACTC1, MYH6, TNNT2, NPPA and ATP2A2 were highly expressed in the mCherry$^+$ cells at the same level as in cardiomyocytes. These data indicated that the five factors can rapidly and efficiently induce the conversion of fibroblasts to cardiomyocytes, but the maturation was a slow process that occurred over several weeks. It is important to note that the total gene expression of the five reprogramming factors were upregulated ~100 fold higher in iCMs than in H9-CMs, especially MESP1, which was undetectable in H9-CMs.

FIGS. 5A-E.

A), FACS analyses of the percent of αMHC-mCherry$^+$ cells among total cells after the 5-factor transduction (n=3) at different time points. B), FACS analyses of the percent of cTnT$^+$ cells among total cells after the 5-factor transduction (n=3) at different time points. C), FACS analyses of the percent of cTnT$^+$ cells among αMHC-mCherry$^+$ cells after the 5-factor transduction (n=3) at different time points. D-E), Expression levels of cardiac specific genes, including ACTC1, ACTN2, MYH6, MYL2, MYL7, TNNT2, NPPA, ATP2A2, PLN, and RYR2, and fibroblasts enriched genes, COL1A1, COL5A2 and FN1, in H9Fs, induced cardiomyocytes (iCMs) (2 weeks (W), 3W, 4W after transduction), and H9-CMs. *p<0.05, **p<0.01 versus relevant control.

The progressive global gene expression pattern of mCherry$^+$ iCMs, H9-CMs, and H9Fs was compared by Whole Transcriptome Shotgun Sequencing, also called RNA-Seq.

Figure 6:
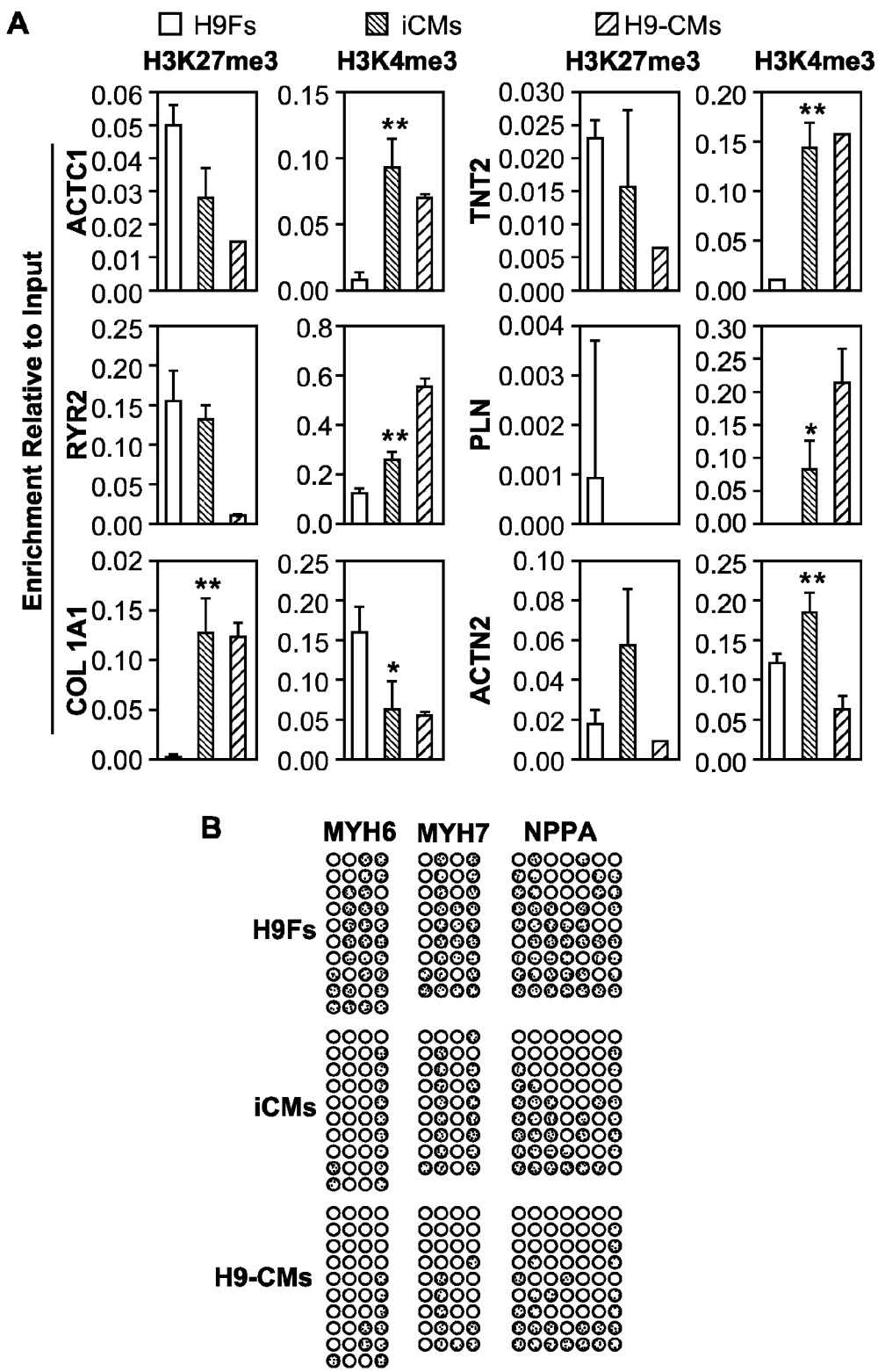
FIGS. 6A-F depicts methylation status analysis of cardiac promoters in mCherry$^+$ cells transduced with ESRRG, GATA4, MEF2C, MESP1, and TBX5.
Figure 6:
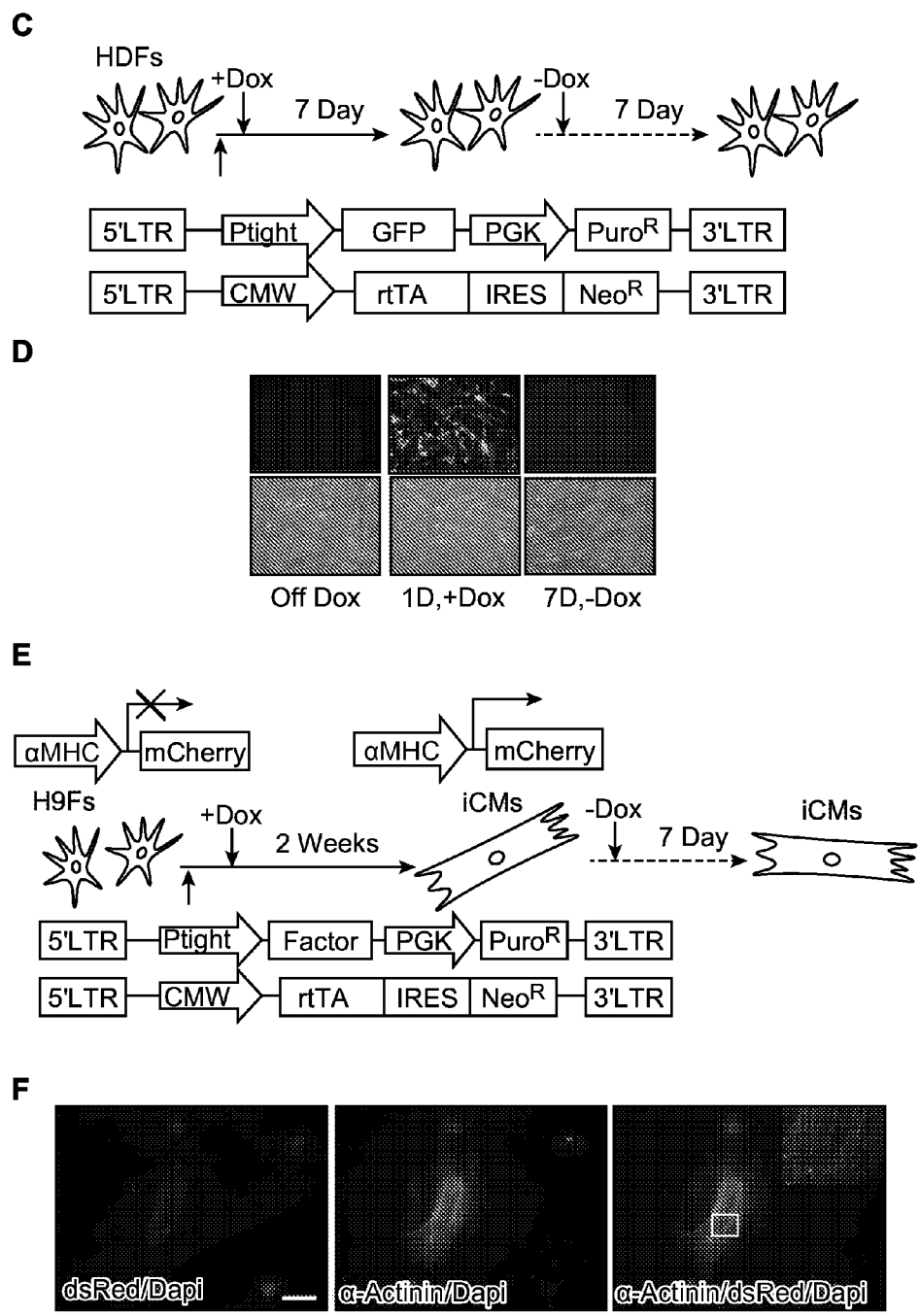

Fibroblasts are Epigenetically Reprogrammed to a Cardiomyocyte-Like State by Defined Transcription Factors To determine if iCMs have gained a cardiomyocyte-like chromatin state, we analyzed the enrichment of histone modifications in the promoter regions of the cardiac-specific genes, including ACTC1, ACTN2, TNNT2, RYR2 and PLN, and a fibroblast enriched gene, COL1A1. The enrichment of trimethylated histone H3 of lysine 27 (H3K27me3) and lysine 4 (H3K4me3), which mark transcriptionally inactive or active chromatin respectively, were analyzed in H9Fs, 2-week mCherry$^+$ iCMs and H9-derived CMs by chromatin immunoprecipitation, followed by qPCR (FIG. 6A). After reprogramming, H3K4me3 was significantly enriched at the promoters of all cardiac-specific genes analyzed in iCMs, and depleted at the promoter of COL1A1. The levels of H3K4me3 enrichment on the promoter region of ACTC1, TNT2 and COL1A1 in iCMs were comparable to those in H9-derived CMs, while H3K27me3 at the promoter of COL1A1 in iCMs increased to the level in CMs, as compared with H9Fs. These results suggested that H9F-derived iCMs gained a chromatin status similar to cardiomyocytes at least in some cardiac specific and fibroblast-enriched genes.

The DNA methylation status of specific loci also reflects the stability of the reprogramming from cardiac fibroblasts to iCMs. Therefore, bisulfite genomic sequencing was performed in the promoter regions of MYH6, MYH7 and NPPA in H9Fs, 2-week mCherry$^+$ iCMs, and mCherry$^+$ H9-CMs. The regions of the three cardiac promoters were hypermethylated in H9Fs, as expected from the cardiomyocyte-specific expression of these genes, but were comparatively demethylated in iCMs, similar to H9-CMs (FIG. 6B). These results indicated that reprogramming by ESRRG, GATA4, MEF2C, MESP1 and TBX5 induced epigenetic resetting of the fibroblast genome to a cardiomyocyte-like state.

To further assess the stability of the reprogramming event, a doxycycline-inducible retroviral system was generated, in which transgene expression of these reprogramming factors was controlled by the presence of doxycycline. H9Fs were transduced with a mixture of retroviruses containing RVX-tetOn-GFP and RVX-rtTA; puromycin and geneticin were used to purify these double-transduced cells, which was used to determine the expression kinetics of this system (FIG. 6C). It was confirmed that GFP was rapidly and robustly expressed within 1 day after doxycycline induction, and instantly diminished and disappeared within 7 days upon withdrawal of doxycycline (FIG. 6D). H9Fs were transduced with a pool of retroviruses containing inducible RVX-ESRRG, GATA4, MEF2C, MESP1, MYOCD, TBX5 and ZFPM2, along with RVX-rtTA, and subsequently treated with doxycycline (FIG. 6E). It was found that αMHC-mCherry was induced in H9Fs as early as 3 days after doxycycline administration while no mCherry$^+$ cells were observed in H9Fs in absence of doxycycline. Doxycycline was withdrawn after 2 weeks of culture, and cells were subsequently cultured without doxycycline for 1 week to fully remove exogenous expression of the reprogramming factors. The reprogrammed iCMs maintained αMHC-mCherry expression and had sarcomeric structures after doxycycline withdrawal (FIG. 6F), suggesting that the fibroblasts were stably reprogrammed into iCMs after 2-week exposure to the reprogramming factors.

FIGS. 6A-F.

A) The promoters of MYH6, MYH7 and NPPA were analyzed with bisulfite genomic sequencing for DNA methylation status in H9Fs, αMHC-mCherry$^+$ iCMs 2-week post-induction, and mCherry$^+$ H9-CMs. Open circles indicate unmethylated CpG dinucleotides; closed circles indicate methylated CpGs. B) The promoters of ACTC1, ACTN2, RYR2, TNNT2, PLN, and COL1A1 were analyzed by ChIP for trimethylation status of histone H3 of lysine 27 or 4 (H3K27me3 or H3K4me3) in H9Fs, iCMs and H9-CMs. *p<0.05, **p<0.01 versus relevant control. C), Scheme representation of the strategy to test expression kinetics of the doxycycline (Dox)-inducible retroviral system. D), Images of H9Fs infected with LVX-tetOn-GFP and LVX-rtTA before (off Dox), 1 day after Dox addition (+Dox) and 7 days after Dox withdrawal (−Dox). E), Scheme of the strategy to determine temporal requirement of reprogramming factors for human cardiac reprogramming. F), Immunofluorescent staining for mCherry, α-actinin and DAPI in human iCMs 1-week after Dox withdrawal. iCMs maintained αMHC-mCherry expression and had a-actinin positive sarcomeric structures. Scale bars represent 20 µm.

Induced Cardiomyocytes Exhibit Cardiac Physiological Functions

Figure 7:
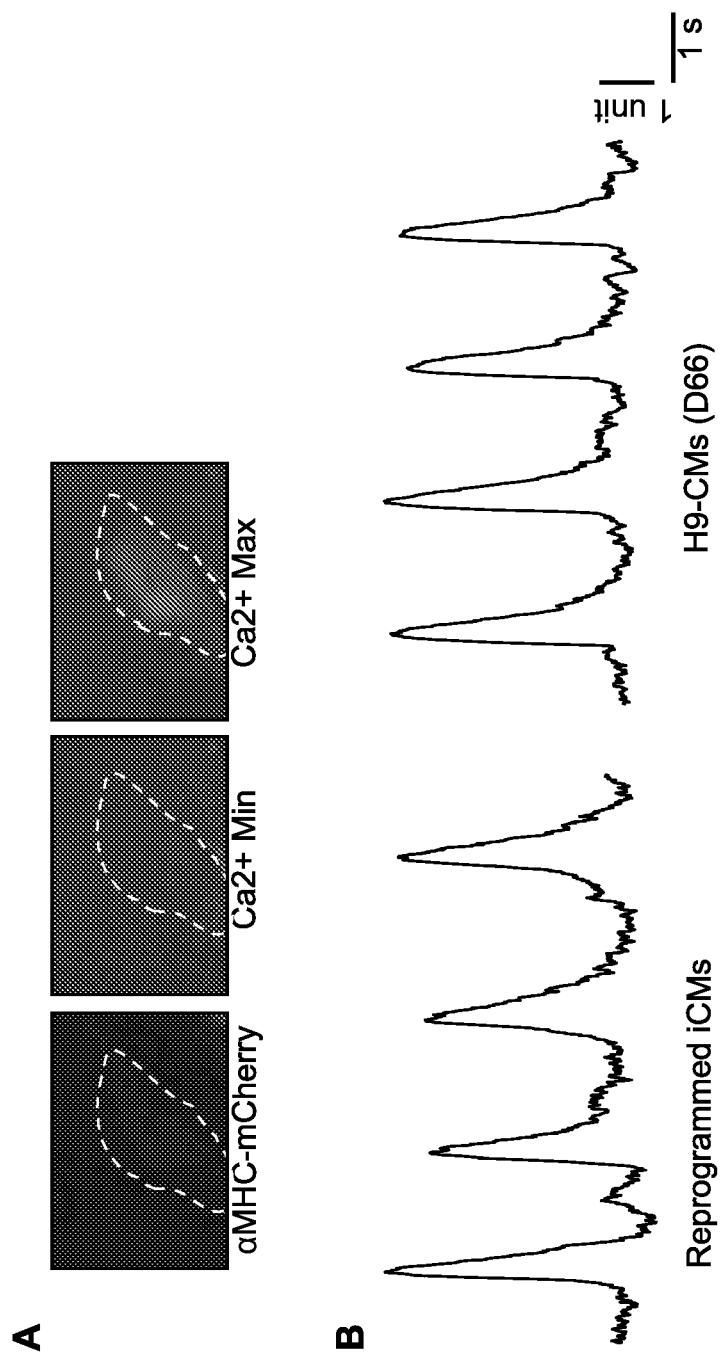
FIGS. 7A-D depict Ca$^{2+}$ transients in mCherry$^+$ cells transduced with ESRRG, GATA4, MEF2C, MESP1, and TBX5.
Figure 7:
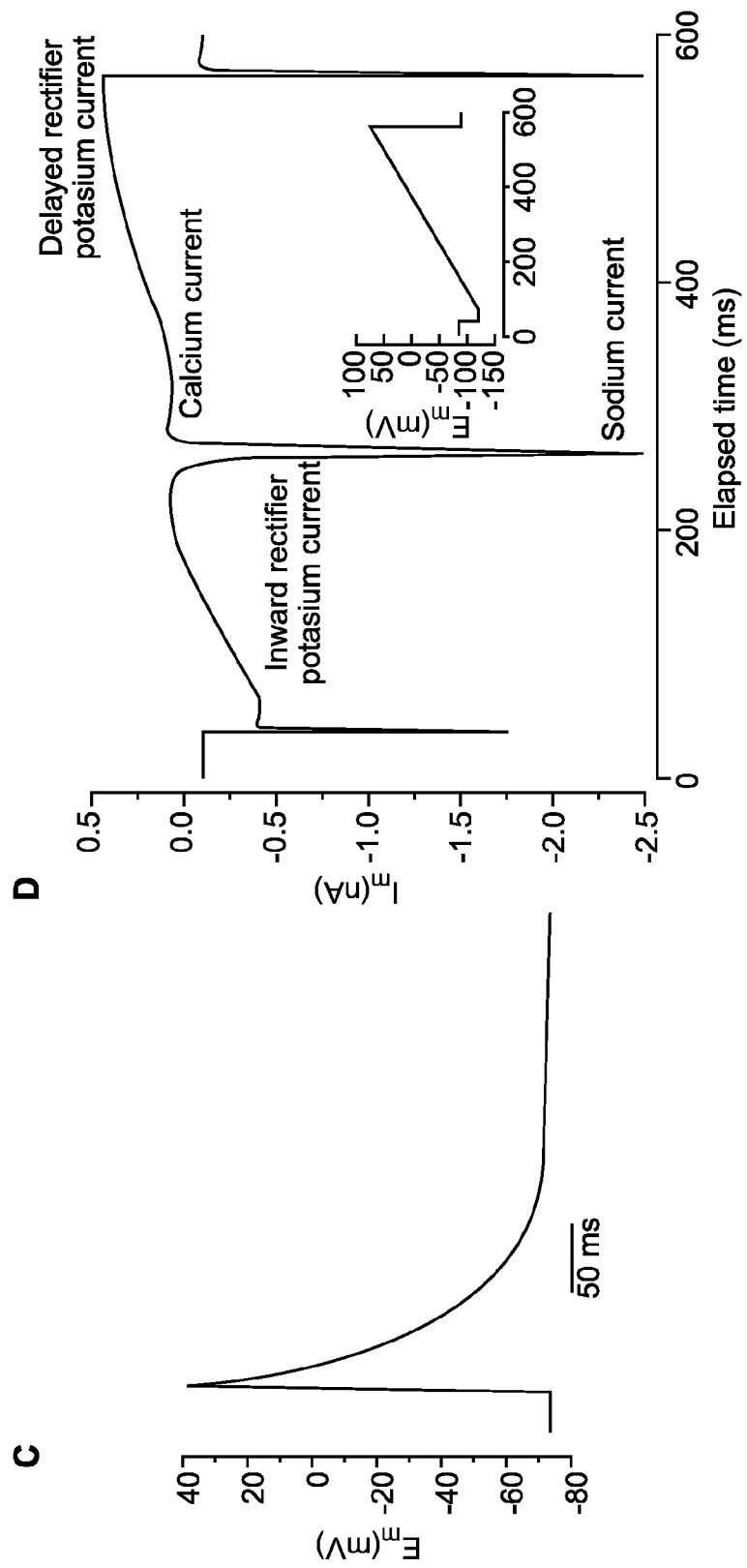

To determine if iCMs possessed the functional properties characteristic of cardiomyocytes, intracellular $Ca^{2+}$ transients were analyzed in iCMs after 2-4 weeks of culture. Spontaneous $Ca^{2+}$ oscillations in these mCherry$^+$ iCMs and mCherry$^-$ cells were not observed. With field electric stimulations, however, around 20% of H9F-derived mCherry$^+$ iCMs 4 weeks after induction generated regular $Ca^{2+}$ transients, which are similar to the $Ca^{2+}$ transients in H9-CMs (FIGS. 7A and 7B).

The electrophysiological properties were characterized with intracellular single-cell recoding by patch-clamp. No action potential was recorded in 4-week reprogrammed aMHC-mCherry$^+$ iCMs, in which calcium current was still missed, although sodium current was measured in iCMs. 10 weeks after retroviral induction, the resting membrane potential of αMHC-mCherry$^+$ iCMs was hyperpolarized to −73.4±8.4 mV (n=6), which is similar to the level of adult CMs. The typical atrial action potentials were successfully elicited in cMHC-mCherry$^+$ iCMs (FIG. 7C), in which sodium current, calcium current, inward rectifier and delayed rectifier potassium currents were measured (FIG. 7D). Therefore, the reprogramming of human fibroblasts to iCMs was associated with changes in gene expression, epigenetic reprogramming and the functional properties characteristic of cardiomyocytes.

FIGS. 7A-D.

A), With Electric field stimulations, $Ca^{2+}$ transients, shown at $Ca^{2+}$ minimal (Min) and Maximal (Max) level, were observed in H9Fs-derived aMHC-mCherry$^+$ iCMs with Fluo-4. B). The typical trace of $Ca^{2+}$ transients recorded from reprogrammed iCMS are similar to the trace recorded from cardiomyocytes differentiated from H9 ES cells (H9-CMs, D66). C), Typical atrial action potential was recorded in αMHC-mCherry$^+$ iCMs 10 weeks after induction. D) Sodium current, calcium current, inward rectifier and delayed rectifier potassium currents were measured in αMHC-mCherry$^+$ iCMs 10 weeks after induction.

Transplanted Fibroblasts Transduced with the 5 Factors Reprogram In Vivo

Figure 8:
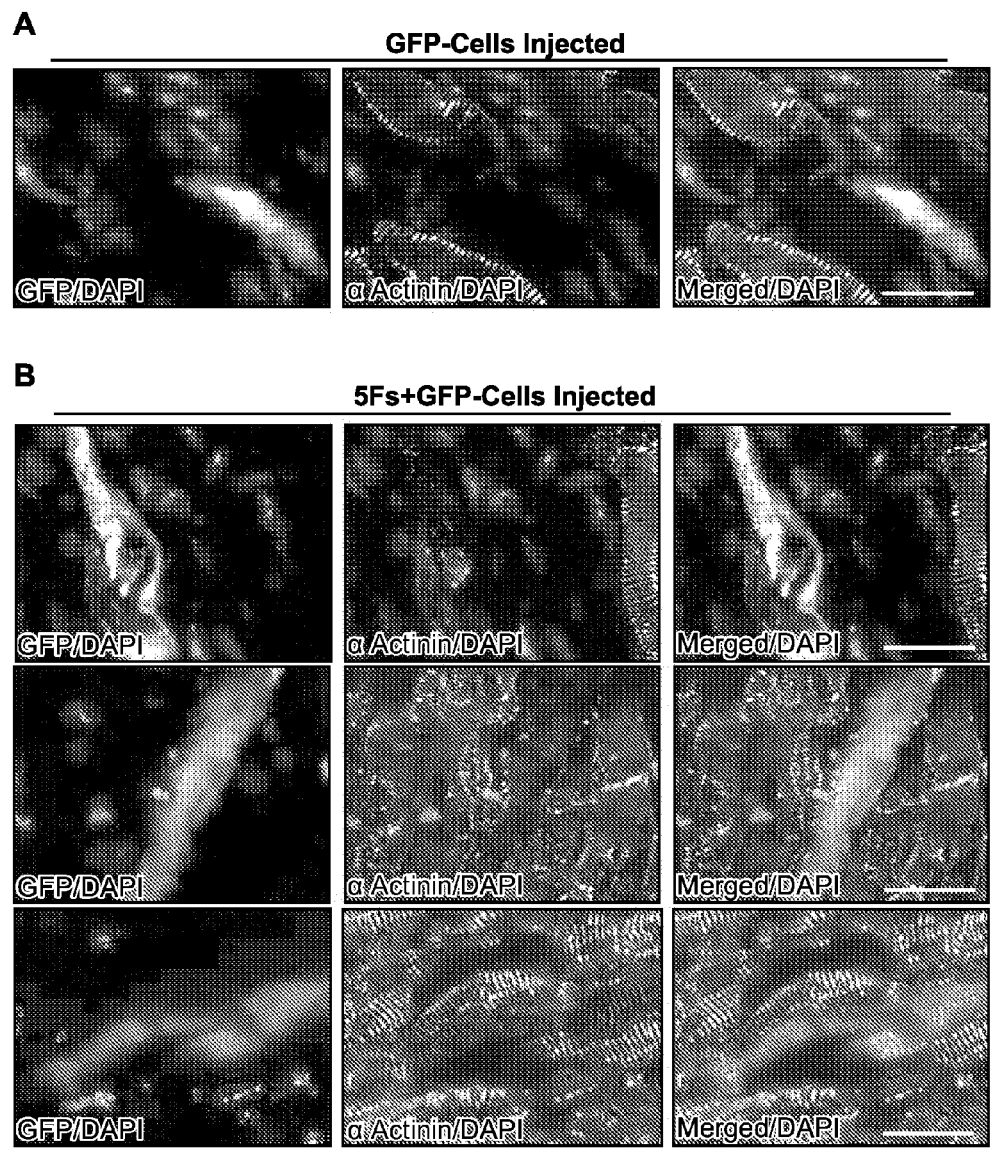
FIGS. 8A and 8B depict in vivo reprogramming of transplanted fibroblasts transduced with ESRRG, GATA4, MEF2C, MESP1, and TBX5.

It was investigated whether fibroblasts transduced with the 5 factors can be reprogrammed to express cardiomyocyte-specific genes in the heart native environment in vivo. H9Fs were harvested 1 day after viral transduction and injected into immunosuppressed NOD-SCID mouse hearts. Cardiac fibroblasts were infected with either the mixture of the 5 factors and GFP retroviruses or only GFP retrovirus (negative control) to be readily identified by fluorescence. Cardiac fibroblasts infected with GFP did not express α-actinin, confirming cardiomyocyte conversion did not occur in the negative control (FIG. 8A). Despite being injected into the heart only 1 day after viral infection, a subset of H9Fs transduced with the 5 factors and GFP expressed α-actinin in the mouse heart 2 weeks after the transplantation, and had sarcomeric structures (FIG. 8B). The reprogrammed human iCMs were further confirmed by human nuclei positive staining. These results suggested that fibroblasts transduced with ESRRG, GATA4, MEF2C, MESP1 and TBX5 can be reprogrammed into cardiomyocytes within 2 weeks upon transplantation in vivo.

FIGS. 8A and 8B.

Transplanted Cardiac Fibroblasts Transduced with the 5 Factors Can Be Reprogrammed to Cardiomyocytes In Vivo. H9Fs infected with GFP (A) or the 5 factor with GFP (B) were transplanted into NOD-SCID mouse hearts 1 day after infection and visualized by histologic section. Note that a subset of induced GFP$^+$ iCMs expressed α-actinin (red) and had sarcomeric structures.

REFERENCES

Baudino, T. A., Carver, W., Giles, W., and Borg, T. K. (2006). Cardiac fibroblasts: friend or foe? Am J Physiol Heart Circ Physiol 291, H1015-1026.

Hudon-David, F., Bouzeghrane, F., Couture, P., and Thibault, G. (2007). Thy-1 expression by cardiac fibroblasts: lack of association with myofibroblast contractile markers. J Mol Cell Cardiol 42, 991-1000.

Ieda, M., Fu, J. D., Delgado-Olguin, P., Vedantham, V., Hayashi, Y., Bruneau, B. G., and Srivastava, D. (2010). Direct reprogramming of fibroblasts into functional cardiomyocytes by defined factors. Cell 142, 375-386.

Ieda, M., Tsuchihashi, T., Ivey, K. N., Ross, R. S., Hong, T. T., Shaw, R. M., and Srivastava, D. (2009). Cardiac fibroblasts regulate myocardial proliferation through beta1 integrin signaling. Dev Cell 16, 233-244.

Kita-Matsuo, H., Barcova, M., Prigozhina, N., Salomonis, N., Wei, K., Jacot, J. G., Nelson, B., Spiering, S., Haverslag, R., Kim, C., et al. (2009). Lentiviral vectors and protocols for creation of stable hESC lines for fluorescent tracking and drug resistance selection of cardiomyocytes. PLoS One 4, e5046.

Kitamura, T., Koshino, Y., Shibata, F., Old, T., Nakajima, H., Nosaka, T., and Kumagai, H. (2003). Retrovirus-mediated gene transfer and expression cloning: powerful tools in functional genomics. Exp Hematol 31, 1007-1014.

Laflamme, M. A., Chen, K. Y., Naumova, A. V., Muskheli, V., Fugate, J. A., Dupras, S. K., Reinecke, H., Xu, C., Hassanipour, M., Police, S., et al. (2007). Cardiomyocytes derived from human embryonic stem cells in pro-survival factors enhance function of infarcted rat hearts. Nat Biotechnol 25, 1015-1024.

Smyth, G. K. (2004). Linear models and empirical bayes methods for assessing differential expression in microarray experiments. Stat Appl Genet Mol Biol 3, Article3.

Snider, P., Standley, K. N., Wang, J., Azhar, M., Doetschman, T., and Conway, S. J. (2009). Origin of cardiac fibroblasts and the role of periostin. Circ Res 105, 934-947.

Takahashi, K., and Yamanaka, S. (2006). Induction of pluripotent stem cells from mouse embryonic and adult fibroblast cultures by defined factors. Cell 126, 663-676.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

van Laake, L. W., Passier, R., Doevendans, P. A., and Mummery, C. L. (2008). Human embryonic stem cell-derived cardiomyocytes and cardiac repair in rodents. Circ Res 102, 1008-1010.

Verrey, F., Closs, E. I., Wagner, C. A., Palacin, M., Endou, H., and Kanai, Y. (2004). CATs and HATs: the SLC7 family of amino acid transporters. Pflugers Arch 447, 532-542.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science 318, 1917-1920.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of generating an induced cardiomyocyte, the method comprising: introducing into a human post-natal fibroblast reprogramming factors comprising Gata4, Mef2c, Tbx5, Mesp1, and Esrrg, wherein said introducing results in direct reprogramming of the post-natal fibroblast into a cardiomyocyte, thereby generating an induced cardiomyocyte.

2. The method of claim 1, wherein said introducing comprises genetically modifying the post-natal fibroblast with one or more nucleic acids comprising nucleotide sequences encoding the reprogramming factor polypeptides.

3. The method of claim 2, wherein said nucleic acid is a recombinant vector.

4. The method of claim 2, wherein the nucleotide sequences are operably linked to a transcription regulatory element.

5. The method of claim 1, wherein said reprogramming factors are exogenous, and where said introducing comprises introducing the exogenous reprogramming factor polypeptides into the post-natal fibroblast.

6. The method of claim 1, wherein said introducing is carried out in vitro.

7. The method of claim 1, wherein said introducing is carried out in vivo.

8. The method of claim 1, wherein the Esrrg factor comprises an amino acid sequence having at least 80% amino acid identity to SEQ ID NO:1.

9. The method of claim 1, wherein the Gata4 factor comprises an amino acid sequence having at least 80% amino acid identity to SEQ ID NO:8.

10. The method of claim 1, wherein the Mef2c factor comprises an amino acid sequence having at least 80% amino acid identity to SEQ ID NO:10 or SEQ ID NO:12.

11. The method of claim 1, wherein the Tbx5 factor comprises an amino acid sequence having at least 80% amino acid identity to SEQ ID NO:14 or SEQ ID NO:16.

12. The method of claim 1, wherein the Mesp1 factor comprises an amino acid sequence having at least 80% amino acid identity to SEQ ID NO:18.

13. The method of claim 1, wherein the method does not comprise introducing into the human post-natal fibroblast an exogenous Sox2 polypeptide or a nucleic acid encoding the exogenous Sox2 polypeptide.

* * * * *